(12) United States Patent
Turner et al.

(10) Patent No.: US 9,551,023 B2
(45) Date of Patent: Jan. 24, 2017

(54) SAMPLE PREPARATION METHOD

(71) Applicant: OXFORD NANOPORE TECHNOLOGIES LIMITED, Oxford Oxfordshire (GB)

(72) Inventors: Daniel John Turner, Oxford (GB); Clive Gavin Brown, Oxford (GB); Stuart William Reid, Oxford (GB); James Anthony Clarke, Oxford (GB); James White, Oxford (GB); David Jackson Stoddart, Oxford (GB)

(73) Assignee: Oxford Nanopore Technologies Ltd., Oxford (GB)

(*) Notice: Subject to any disclaimer, the term of this patent is extended or adjusted under 35 U.S.C. 154(b) by 0 days.

(21) Appl. No.: 14/427,554

(22) PCT Filed: Sep. 6, 2013

(86) PCT No.: PCT/GB2013/052337
§ 371 (c)(1),
(2) Date: Mar. 11, 2015

(87) PCT Pub. No.: WO2014/041337
PCT Pub. Date: Mar. 20, 2014

(65) Prior Publication Data
US 2015/0247183 A1  Sep. 3, 2015

Related U.S. Application Data

(60) Provisional application No. 61/701,238, filed on Sep. 14, 2012.

(51) Int. Cl.
| | | |
|---|---|---|
| C12P 19/34 | (2006.01) |
| C07H 21/00 | (2006.01) |
| C07H 21/04 | (2006.01) |
| C12Q 1/68 | (2006.01) |

(52) U.S. Cl.
CPC ............. *C12Q 1/6806* (2013.01); *C07H 21/04* (2013.01); *C12Q 1/6869* (2013.01)

(58) Field of Classification Search
None
See application file for complete search history.

(56) References Cited

U.S. PATENT DOCUMENTS

| | | |
|---|---|---|
| 6,426,231 B1 | 7/2002 | Bayley et al. |
| 8,105,846 B2 | 1/2012 | Bayley et al. |
| 8,828,208 B2 | 9/2014 | Canas et al. |
| 2002/0197618 A1 | 12/2002 | Sampson |
| 2005/0014162 A1 | 1/2005 | Barth et al. |
| 2010/0196203 A1 | 8/2010 | Sanghera et al. |
| 2011/0120871 A1 | 5/2011 | Reid et al. |
| 2011/0121840 A1 | 5/2011 | Sanghera et al. |
| 2011/0177498 A1 | 7/2011 | Clarke et al. |
| 2011/0229877 A1 | 9/2011 | Jayasinghe et al. |
| 2012/0058468 A1 | 3/2012 | McKeown |
| 2012/0100530 A1 | 4/2012 | Moysey et al. |
| 2012/0107802 A1 | 5/2012 | Stoddart et al. |
| 2012/0322679 A1 | 12/2012 | Brown et al. |
| 2014/0051069 A1 | 2/2014 | Jayasinghe et al. |
| 2014/0186823 A1 | 7/2014 | Clarke et al. |
| 2014/0296083 A1 | 10/2014 | Brown et al. |
| 2015/0008126 A1 | 1/2015 | Maglia et al. |
| 2015/0031020 A1 | 1/2015 | Jayasinghe et al. |
| 2015/0152492 A1 | 6/2015 | Brown et al. |
| 2015/0177237 A1 | 6/2015 | Turner et al. |
| 2015/0301015 A1 | 10/2015 | Fordham et al. |
| 2016/0010147 A1 | 1/2016 | Heron et al. |

FOREIGN PATENT DOCUMENTS

| | | |
|---|---|---|
| WO | WO 00/28312 | 5/2000 |
| WO | WO 2005/124888 | 12/2005 |
| WO | 2006/100484 A2 | 9/2006 |
| WO | 2008010212 A2 | 1/2008 |
| WO | 2008102120 A1 | 8/2008 |
| WO | WO 2008/102121 | 8/2008 |
| WO | WO 2008/124107 | 10/2008 |
| WO | 2009/035647 A1 | 3/2009 |
| WO | 2009046149 A1 | 4/2009 |
| WO | 2009/077734 A2 | 6/2009 |
| WO | 2010/004265 A1 | 1/2010 |
| WO | 2010/004273 A1 | 1/2010 |
| WO | 2010/086603 A1 | 8/2010 |
| WO | WO 2010/122293 | 10/2010 |
| WO | WO 2011/067559 | 6/2011 |
| WO | WO 2011/103424 | 8/2011 |
| WO | WO 2012/009578 | 1/2012 |
| WO | 2012088339 A2 | 6/2012 |
| WO | 2012129242 A2 | 9/2012 |

(Continued)

OTHER PUBLICATIONS

U.S. Appl. No. 13/147,159, filed Nov. 15, 2011, Brian McKeown.
U.S. Appl. No. 14/234,698, filed Apr. 25, 2014, Clive Gavin Brown.
U.S. Appl. No. 14/334,285, filed Jul. 17, 2014, Giovanni Maglia.
U.S. Appl. No. 13/984,628, filed Feb. 27, 2014, James Clarke.
U.S. Appl. No. 13/002,717, filed Mar. 30, 2011, James Clarke.
U.S. Appl. No. 14/455,394, filed Aug. 8, 2014, Lakmal Jayasinghe.
U.S. Appl. No. 13/968,778, filed Aug. 16, 2013, Lakmal Jayasinghe.
U.S. Appl. No. 12/093,610, filed Jul. 28, 2008, Hagan Bayley.
Altschul S. F. (1993) J Mol Evol 36:290-300.
Altschul, S.F et al (1990) J Mol Biol 215:403-10.
Braha et al, Chem Biol. Jul. 1997;4(7):497-505.

(Continued)

*Primary Examiner* — James Martinell
(74) *Attorney, Agent, or Firm* — Wolf, Greenfield & Sacks, P.C.

(57) ABSTRACT

The invention relates to a method for modifying a template polynucleotide for characterization, especially for nanopore sequencing. The method produces a modified polynucleotide which is complementary to the template polynucleotide at some positions and which contains universal or abasic nucleotides at the other, and in some instances predicable, positions. The resulting modified polynucleotide can then be characterized.

27 Claims, 14 Drawing Sheets

(56) References Cited

FOREIGN PATENT DOCUMENTS

| WO | WO 2012/164270 | 12/2012 |
|----|----------------|---------|
| WO | 2013014451 A1 | 1/2013 |
| WO | WO 2013/057495 | 4/2013 |
| WO | WO 2013/098561 | 7/2013 |
| WO | WO 2013/098562 | 7/2013 |
| WO | WO 2013/121201 | 8/2013 |
| WO | WO 2013/153359 | 10/2013 |
| WO | WO 2014/013259 | 1/2014 |
| WO | WO 2014/013260 | 1/2014 |
| WO | WO 2014/013262 | 1/2014 |
| WO | 2014041337 A1 | 3/2014 |
| WO | WO 2014/072703 | 5/2014 |
| WO | WO 2014/135838 | 9/2014 |
| WO | WO 2015/055981 | 4/2015 |
| WO | WO 2015/056028 | 4/2015 |
| WO | WO 2015/110777 | 7/2015 |
| WO | WO 2015/150786 | 10/2015 |

OTHER PUBLICATIONS

Dahl et al; Direct Observation of Translocation in Individual DNA Polymerase Complexes; J. Bio. Chem., vol. 287, Nr:16, pp. 13407-13421; 2012.

Devereux et al (1984) Nucleic Acids Research 12, p. 387-395.

Gonzalez-Perez et al., Langmuir, 2009, 25, 10447-10450.

Grant, G. P. and P. Z. Qin (2007). "A facile method for attaching nitroxide spin labels at the 5' terminus of nucleic acids." Nucleic Acids Res 35(10): e77.

Holden et al., J Am Chem Soc. Jul. 11, 2007; 129(27):8650-5.

International Preliminary Report on Patentability, PCT/GB2013/052337, dated Mar. 17, 2015, 1-8.

International Search Report and Written Opinion, PCT/GB2013/052337, dated Nov. 13, 2013, 1-12.

Ivanov AP et al., Nano Lett. Jan. 12, 2011;11(1):279-85).

Kumar, A., P. Tchen, et al. (1988). "Nonradioactive labeling of synthetic oligonucleotide probes with terminal deoxynucleotidyl transferase." Anal Biochem 169(2): 376-82.

Lieberman KR et al, J Am Chem Soc. 2010;132(50):17961-72.

M.A. Holden, H. Bayley. J. Am. Chem. Soc. 2005, 127, 6502-6503.

Manrao et al; Reading DNA at single-nucleotide resolution with a mutant MspA nanopore and phi29 DNA polymerase; Nature Biotechnology, vol. 30, Nr:4, pp. 349-353; 2012.

Montal and Mueller (Proc. Natl. Acad. Sci. USA., 1972; 69: 3561-3566.

Nikolov, V., R. Lipowsky, et al. (2007). "Behavior of giant vesicles with anchored DNA molecules." Biophys J 92(12): 4356-68.

Pfeiffer, I. and F. Hook (2004). "Bivalent cholesterol-based coupling of oligonucletides to lipid membrane assemblies." J Am Chem Soc 126(33): 10224-5.

Soni GV et al., Rev Sci Instrum. Jan. 2010;81(1):014301.

Stoddart D et al., Proc Natl Acad Sci, 12;106(19):7702-7.

Troutt, A. B., M. G. McHeyzer-Williams, et al. (1992). "Ligation-anchored PCR: a simple amplification technique with single-sided specificity." Proc Natl Acad Sci U S A 89(20): 9823-5.

Van Lengerich, B., R. J. Rawle, et al. "Covalent attachment of lipid vesicles to a fluid-supported bilayer allows observation of DNA-mediated vesicle interactions." Langmuir 26(11): 8666-72.

Yoshina-Ishii, C. and S. G. Boxer (2003). "Arrays of mobile tethered vesicles on supported lipid bilayers." J Am Chem Soc 125(13): 3696-7.

Actis et al., Reversible thrombin detection by aptamer functionalized STING sensors. Biosens Bioelectron. Jul. 15, 2011;26(11):4503-7. doi: 10.1016/j.bios.2011.05.010. Epub May 12, 2011.

Anderson, The clinical plasma proteome: a survey of clinical assays for proteins in plasma and serum. Clin Chem. Feb. 2010;56(2):177-85. doi:10.1373/clinchem.2009.126706. Epub Nov. 2, 2009.

Ayub et al., Individual RNA base recognition in immobilized oligonucleotides using a protein nanopore. Nano Lett. Nov. 14, 2012;12(11):5637-43. doi: 10.1021/nl3027873. Epub Oct. 19, 2012.

Barshack et al., Differential diagnosis of hepatocellular carcinoma from metastatic tumors in the liver using microRNA expression. Int J Biochem Cell Biol. Aug. 2010;42(8):1355-62. doi:10.1016/j.biocel.2009.02.021. Epub Mar. 6, 2009.

Berezovski et al., Non-SELEX selection of aptamers. J Am Chem Soc. Feb. 8, 2006;128(5):1410-1.

Bock et al., Selection of single-stranded DNA molecules that bind and inhibit human thrombin. Nature. Feb. 6, 1992;355(6360):564-6.

Branton et al., The potential and challenges of nanopore sequencing. Nat Biotechnol. Oct. 2008;26(10):1146-53. doi:10.1038/nbt.1495.

Chandler et al., Membrane surface dynamics of DNA-threaded nanopores revealed by simultaneous single-molecule optical and ensemble electrical recording. Langmuir. Feb. 3, 2004;20(3):898-905.

Chen et al., Highly sensitive and specific microRNA expression profiling using BeadArray technology. Nucleic Acids Res. Aug. 2008;36(14):e87. doi:10.1093/nar/gkn387. Epub Jun. 25, 2008.

Chen et al., Real-time quantification of microRNAs by stem-loop RT-PCR. Nucleic Acids Res. Nov. 27, 2005;33(20):e179.

Cissell et al., Bioluminescence-based detection of microRNA, miR21 in breast cancer cells. Anal Chem. Apr. 1, 2008;80(7):2319-25. doi: 10.1021/ac702577a. Epub Feb. 27, 2008.

Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.

Deamer, Nanopore analysis of nucleic acids bound to exonucleases and polymerases. Annu Rev Biophys. 2010;39:79-90. doi:10.1146/annurev.biophys.093008.131250.

Edwards et al., The role of proteomics in clinical cardiovascular biomarker discovery. Mol Cell Proteomics. Oct. 2008;7(10):1824-37. doi: 10.1074/mcp.R800007-MCP200. Epub Jul. 30, 2008.

Eliseev et al., Molecular Recognition of Nucleotides, Nucleosides, and Sugars by Aminocyclodextrins. J. Am. Chem. Soc., vol. 116:6081-6088 (1994).

Esquela-Kerscher et al., Oncomirs—microRNAs with a role in cancer. Nat Rev Cancer. Apr. 2006;6(4):259-69.

Gilad et al., Serum microRNAs are promising novel biomarkers. PLoS One. Sep. 5, 2008;3(9):e3148. doi:10.1371/journal.pone.0003148.

Gu et al., Detection of miRNAs with a nanopore single-molecule counter. Expert Rev Mol Diagn. Jul. 2012;12(6):573-84. doi: 10.1586/erm.12.58.

Gu et al., Single molecule sensing by nanopores and nanopore devices. Analyst. Mar. 2010;135(3):441-51. doi: 10.1039/b907735a. Epub Dec. 22, 2009.

Hall et al., Hybrid pore formation by directed insertion of α-haemolysin into solid-state nanopores. Nat Nanotechnol. Dec. 2010;5(12):874-7. doi: 10.1038/nnano.2010.237. Epub Nov. 28, 2010.

Hornblower et al., Single-molecule analysis of DNA-protein complexes using nanopores. Nat Methods. Apr. 2007;4(4):315-7. Epub Mar. 4, 2007.

Jacquet et al., Identification of cardiac myosin-binding protein C as a candidate biomarker of myocardial infarction by proteomics analysis. Mol Cell Proteomics. Dec. 2009;8(12):2687-99. doi: 10.1074/mcp.M900176-MCP200. Epub Aug. 31, 2009.

Jiang et al., miR2Disease: a manually curated database for microRNA deregulation in human disease. Nucleic Acids Res. Jan. 2009;37(Database issue):D98-104. doi:10.1093/nar/gkn714. Epub Oct. 15, 2008.

Kankia et al., Folding of the thrombin aptamer into a G-quadruplex with Sr(2+): stability, heat, and hydration. J Am Chem Soc. Nov. 7, 2001;123(44):10799-804.

Keller et al., Toward the blood-borne miRNome of human diseases. Nat Methods. Sep. 4, 2011;8(10):841-3. doi: 10.1038/nmeth.1682.

(56) References Cited

OTHER PUBLICATIONS

Khan et al., Quantitative analysis of microRNA in blood serum with protein-facilitated affinity capillary electrophoresis. Anal Chem. Aug. 15, 2011;83(16):6196-201. doi: 10.1021/ac2016213. Epub Jul. 18, 2011.

Kirschner et al., Haemolysis during sample preparation alters microRNA content of plasma. PLoS One. 2011;6(9):e24145. doi: 10.1371/journal.pone.0024145. Epub Sep. 1, 2011.

Kozarewa et al., 96-plea molecular barcoding for the Illumina Genome Analyzer. Methods Mol Biol. 2011;733:279-98. doi: 10.1007/978-1-61779-089-8_20.

Krichevsky et al., A microRNA array reveals extensive regulation of microRNAs during brain development. Rna. Oct. 2003;9(10):1274-81. Erratum in: RNA. Mar. 2004;10(3):551.

Lee et al., The C. elegans heterochronic gene lin-4 encodes small RNAs with antisense complementarity to lin-14. Cell. Dec. 3, 1993;75(5):843-54.

Lewis et al., Conserved seed pairing, often flanked by adenosines, indicates that thousands of human genes are microRNA targets. Cell. Jan. 14, 2005;120(1):15-20.

Loakes, Survey and summary: The applications of universal DNA base analogues. Nucleic Acids Res. Jun. 15, 2001;29(12):2437-47.

Lu et al., MicroRNA expression profiles classify human cancers. Nature. Jun. 9, 2005;435(7043):834-8.

Marathias et al., Structures of the potassium-saturated, 2:1, and intermediate, 1:1, forms of a quadruplex DNA. Nucleic Acids Res. May 1, 2000;28(9):1969-77.

Marusic et al., Solution-state structure of an intramolecular G-quadruplex with propeller, diagonal and edgewise loops . (2012) Nucleic Acids Research, 1-11.

Movileanu, Interrogating single proteins through nanopores: challenges and opportunities. Trends Biotechnol. Jun. 2009;27(6):333-41. doi:10.1016/j.tibtech.2009.02.008. Epub Apr. 23, 2009.

Murphy et al., Reliability of real-time reverse-transcription PCR in clinical diagnostics: gold standard or substandard? Expert Rev Mol Diagn. Mar. 2009;9(2):187-97. doi: 10.1586/14737159.9.2.187.

Nasheri et al., An enzyme-linked assay for the rapid quantification of microRNAs based on the viral suppressor of RNA silencing protein p19. Anal Biochem. May 15, 2011;412(2):165-72. doi: 10.1016/j.ab.2011.01.030. Epub Feb. 1, 2011.

Reinhart et al., MicroRNAs in plants. Genes Dev. Jul. 1, 2002;16(13):1616-26. Erratum in: Genes Dev Sep. 1, 2002;16(17):2313.

Rosenfeld et al., MicroRNAs accurately identify cancer tissue origin. Nat Biotechnol. Apr. 2008;26(4):462-9. doi:10.1038/nbt1392. Epub Mar. 23, 2008.

Rotem et al., Protein detection by nanopores equipped with aptamers. J Am Chem Soc. Feb. 8, 2012;134(5):2781-7. doi:10.1021/ja2105653. Epub Jan. 26, 2012.

Shim et al., Single-molecule detection of folding and unfolding of the G-quadruplex aptamer in a nanopore nanocavity. Nucleic Acids Res. Feb. 2009;37(3):972-82. doi: 10.1093/nar/gkn968. Epub Dec. 26, 2008.

Stoltenburg et al., SELEX—a (r)evolutionary method to generate high-affinity nucleic acid ligands. Biomol Eng. Oct. 2007;24(4):381-403. Epub Jun. 16, 2007.

Tazi et al., Alternative splicing and disease. Biochim Biophys Acta. Jan. 2009;1792(1):14-26. doi: 10.1016/j.bbadis.2008.09.017. Epub Oct. 17, 2008.

Tian et al., Designing a polycationic probe for simultaneous enrichment and detection of microRNAs in a nanopore. ACS Nano. May 28, 2013;7(5):3962-9. doi: 10.1021/nn305789z. Epub Apr. 10, 2013.

Tuerk et al., Systematic evolution of ligands by exponential enrichment: Rna ligands to bacteriophage T4 Dna polymerase. Science. Aug. 3, 1990;249(4968):505-10.

Venkatesan et al., Nanopore sensors for nucleic acid analysis. Nat Nanotechnol. Sep. 18, 2011;6(10):615-24. doi: 10.1038/nnano.2011.129.

Wang et al., Nanopore-based detection of circulating microRNAs in lung cancer patients. Nat Nanotechnol. Sep. 4, 2011;6(10):668-74. doi: 10.1038/nnano.2011.147.

Wang et al., Serum miR-146a and miR-223 as potential new biomarkers for sepsis. Biochem Biophys Res Commun Mar. 26, 2010;394(1):184-8. doi: 10.1016/j.bbrc.2010.02.145. Epub Feb. 24, 2010.

Wanunu et al., Rapid electronic detection of probe-specific microRNAs using thin nanopore sensors. Nat Nanotechnol. Nov. 2010;5(11):807-14. doi: 10.1038/nnano.2010.202. Epub Oct. 24, 2010.

White et al., Generation of species cross-reactive aptamers using "toggle" SELEX. Mol Ther. Dec. 2001;4(6):567-73.

Wightman et al., Posttranscriptional regulation of the heterochronic gene lin-14 by lin-4 mediates temporal pattern formation in C. elegans. Cell. Dec. 3, 1993;75(5):855-62.

SAMPLE PREPARATION METHOD

CROSS REFERENCE TO RELATED APPLICATIONS

This application is a 35 U.S.C. 371 national stage filing of International Application No. PCT/GB2013/052337, filed on Sep. 6, 2013, which claims priority to, and the benefit of, U.S. Application No. 61/701,238, filed on Sep. 14, 2012. The contents of the aforementioned applications are hereby incorporated by reference in their entireties.

FIELD OF THE INVENTION

The invention relates to a method for modifying a template polynucleotide for characterisation, especially for nanopore sequencing. The method produces a modified polynucleotide which is complementary to the template polynucleotide at some positions and which contains universal or abasic nucleotides at the other, and in some instances predicable, positions. The resulting modified polynucleotide can then be characterised.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identity of the nucleotides are derived. Strand sequencing can involve the use of a polynucleotide binding protein to control the movement of the polynucleotide through the pore.

SUMMARY OF THE INVENTION

The inventors have surprisingly demonstrated that it is possible to modify a template polynucleotide to produce a one or more modified polynucleotides that are each easier to characterise, such as by strand sequencing, than the original template polynucleotide. Subsequent characterisation of the modified polynucleotide(s) allows the character of the template polynucleotide to be more easily determined.

The modification method uses a population of nucleotide oligomers which are capable of hybridizing to the template polynucleotide. All of the oligomers in the population have the same general pattern of (a) one or more universal nucleotides or abasic nucleotides (herein called Z) and (b) one or more nucleotides which are complementary to those in the template polynucleotide (herein called N or complementary nucleotides), such as A, T, U, G or C. The population comprises every possible combination of the complementary nucleotides. This combination of (a) nucleotides that will pair with all nucleotides (i.e. universal nucleotides or abasic nucleotides) and (b) every combination of complementary nucleotides in the population will allow the oligomers to hybridise to most of, if not all of, the template polynucleotide.

Ligation of the hybridised oligomers results in a modified polynucleotide which is complementary to the template polynucleotide at some positions and which contains universal or abasic nucleotides at other, and in some instances predicable, positions. By beginning ligation at different positions, it is possible to produce a plurality of modified polynucleotides which are each complementary to the template polynucleotide at different positions. If the plurality of modified polynucleotides as a whole contains nucleotides that are complementary to all of the nucleotides in the template polynucleotide, it is possible to reconstruct the sequence of the template polynucleotide from the sequences of the plurality of modified polynucleotides.

Accordingly, the invention provides a method for modifying a template polynucleotide for characterisation, comprising:

(a) contacting the template polynucleotide with a population of nucleotide oligomers under conditions in which the oligomers can hybridise to the polynucleotide, wherein all of the oligomers in the population (i) have from 2 to 16 nucleotides and (ii) comprise or consist of the same pattern of one or more instances of $Z_XN_Y$ and/or $N_YZ_X$ where Z is a universal nucleotide and/or an abasic nucleotide, N is a nucleotide which is complementary to one of the nucleotides in the template polynucleotide, X is 1, 2, 3 or 4 and Y is 1, 2, 3 or 4 and wherein the population comprises every possible combination of nucleotides N which are complementary to all of the nucleotides in the template polynucleotide; and (b) ligating together those oligomers that hybridise to the polynucleotide and thereby providing a modified polynucleotide for characterisation.

The invention also provides:
a polynucleotide modified using the method of the invention;
a plurality of polynucleotides modified using the method of the invention;
a population of nucleotide oligomers as defined above;
a method of characterising a polynucleotide modified using the method of the invention, comprising a) contacting the modified polynucleotide with a transmembrane pore such that the polynucleotide moves through the pore and b) taking one or more measurements as the polynucleotide moves with respect to the pore wherein the measurements are indicative of one or more characteristics of the polynucleotide and thereby characterising the modified polynucleotide;
a method of characterising a template polynucleotide, comprising a) modifying the template polynucleotide using the method of the invention to produce a plurality of different modified polynucleotides; b) contacting each modified polynucleotide with a transmembrane pore such that each polynucleotide moves through the pore; and c) taking one or more measurements as each polynucleotide moves with respect to the pore wherein the measurements are indicative of one or more characteristics of the polynucleotide and thereby characterising the template polynucleotide; and
a kit for characterising a template polynucleotide comprising (a) a population of nucleotide oligomers as defined above and (b) a ligase enzyme.

DESCRIPTION OF THE SEQUENCE LISTING

Figure 1:
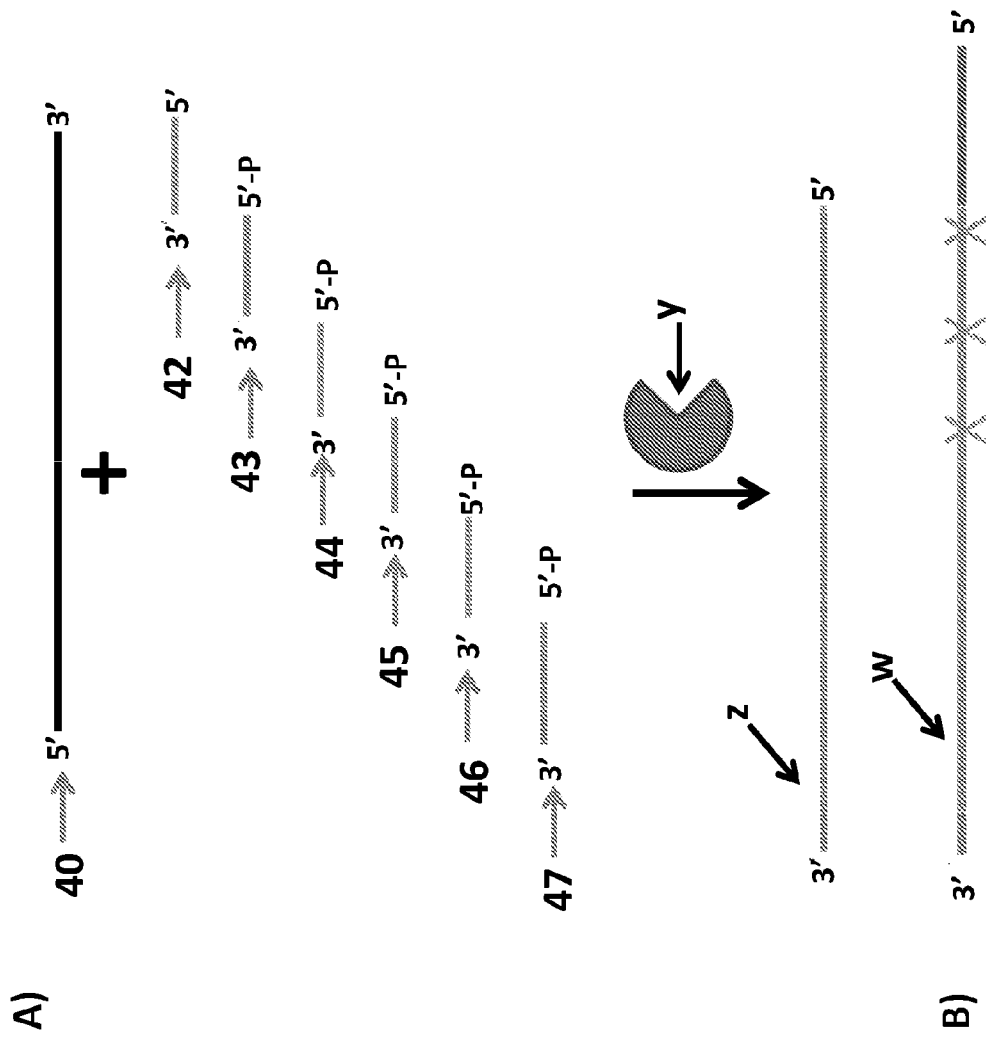
FIG. 1 A) shows how the various nucleotide oligomers (SEQ ID NOs: 42-47, SEQ ID NOs are indicated on one side of the corresponding strand by an arrow) can hybridise to the sense template polynucleotide strand (SEQ ID NO: 40) and then be ligated together by a DNA ligase (labelled as y) to form the ligated antisense strand (SEQ ID NO: 42-47 labelled z) and B) shows the chemically synthesised antisense (labelled w) which contains three abasic residues (shown as X's) and a polyT extension (SEQ ID NO: 48).

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the polynucleotide sequence encoding the Phi29 DNA polymerase.

SEQ ID NO: 9 shows the amino acid sequence of the Phi29 DNA polymerase.

SEQ ID NO: 10 shows the codon optimised polynucleotide sequence derived from the sbcB gene from *E. coli*. It encodes the exonuclease I enzyme (EcoExo I) from *E. coli*.

SEQ ID NO: 11 shows the amino acid sequence of exonuclease I enzyme (EcoExo I) from *E. coli*.

SEQ ID NO: 12 shows the codon optimised polynucleotide sequence derived from the xthA gene from *E. coli*. It encodes the exonuclease III enzyme from *E. coli*.

SEQ ID NO: 13 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 14 shows the codon optimised polynucleotide sequence derived from the recJ gene from *T. thermophilus*. It encodes the RecJ enzyme from *T. thermophilus* (TthRecJ-cd).

SEQ ID NO: 15 shows the amino acid sequence of the RecJ enzyme from *T thermophilus* (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 16 shows the codon optimised polynucleotide sequence derived from the bacteriophage lambda exo (redX) gene. It encodes the bacteriophage lambda exonuclease.

SEQ ID NO: 17 shows the amino acid sequence of the bacteriophage lambda exonuclease. The sequence is one of three identical subunits that assemble into a trimer. The enzyme performs highly processive digestion of nucleotides from one strand of dsDNA, in a 5'-3' direction (http://www.neb.com/nebecomm/products/productMO262.asp).

Enzyme initiation on a strand preferentially requires a 5' overhang of approximately 4 nucleotides with a 5' phosphate.

SEQ ID NO: 18 shows the amino acid sequence of Hel308 Mbu.

SEQ ID NO: 19 shows the amino acid sequence of Hel308 Csy.

SEQ ID NO: 20 shows the amino acid sequence of Hel308 Tga.

SEQ ID NO: 21 shows the amino acid sequence of Hel308 Mhu.

SEQ ID NO: 22 shows the amino acid sequence of TraI Eco.

SEQ ID NO: 23 shows the amino acid sequence of XPD Mbu.

SEQ ID NOs: 24 to 39 are shown below in Representations A to D. In the sequence listing, Z is shown as inosine because this is the only universal nucleotide which appears in Annex C, Appendix 2, Table 2 of WIPO's Standard ST.25 for the presentation of nucleotide and amino acid sequence listings in patent applications.

SEQ ID NO: 40 shows a polynucleotide sequence used in Example 1.

SEQ ID NO: 41 shows a polynucleotide sequence used in Example 1. This sequence has four 2' O-methyl uracils and a thymine at the 3' end of the strand.

SEQ ID NO: 42 shows a polynucleotide sequence used in Example 1.

SEQ ID NO: 43 shows a polynucleotide sequence used in Example 1. This sequence has a phosphate attached to its 5' end.

SEQ ID NO: 44 shows a polynucleotide sequence used in Example 1. This sequence has a phosphate attached to its 5' end.

SEQ ID NO: 45 shows a polynucleotide sequence used in Example 1. This sequence has a phosphate attached to its 5' end.

SEQ ID NO: 46 shows a polynucleotide sequence used in Example 1. This sequence has a phosphate attached to its 5' end.

SEQ ID NO: 47 shows a polynucleotide sequence used in Example 1. This sequence has a phosphate attached to its 5' end and has four 2' O-methyl uracils and a thymine at the 3' end of the strand.

SEQ ID NO: 48 shows a polynucleotide sequence used in Example 1: TTTTTTTTTTTTTTTTTTTTTTTTTTTTTTTTTTTT TTTTTTTTTTTACAXAAACGTXA TTGCCXGGCG-TACGGGGAAGGACGTCAATA. This sequence has has four 2' O-methyl uracils and a thymine at the 3' end of the strand and 3 abasic residues indicated in the sequence by an X. This sequence does not appear in the sequence listing because it includes abasic nucleotides, i.e. nucleotides which do not appear in Annex C, Appendix 2, Table 2 of WIPO's Standard ST.25.

SEQ ID NO: 49 shows a polynucleotide sequence used in Example 2.

SEQ ID NO: 50 shows a polynucleotide sequence used in Example 2: TTTTTTTTTTTTTTTTTTTTTTTTTTTTTTTTTTTT TTTTTTTTTTACAXAAA. This polynucleotide sequence has an abasic residue at position 54 indicated in the sequence by an X. This sequence does not appear in the sequence listing because it includes an abasic nucleotide.

SEQ ID NO: 51 shows a polynucleotide sequence used in Example 2: CGTXATT. This sequence has a phosphate attached to its 5' end and an abasic residue at position 4 indicated in the sequence by an X. This sequence does not appear in the sequence listing because it includes an abasic nucleotide.

SEQ ID NO: 52 shows a polynucleotide sequence used in Example 2: GCCXGGC. This sequence has a phosphate attached to its 5' end and an abasic residue at position 4 indicated in the sequence by an X. This sequence does not appear in the sequence listing because it includes an abasic nucleotide.

SEQ ID NO: 53 shows a polynucleotide sequence used in Example 2: GTAXGGG. This sequence has a phosphate attached to its 5' end and an abasic residue at position 4 indicated in the sequence by an X. This sequence does not appear in the sequence listing because it includes an abasic nucleotide.

SEQ ID NO: 54 shows a polynucleotide sequence used in Example 2. This sequence has a phosphate attached to its 5' end and a 3' cholesterol TEG.

SEQ ID NO: 55 shows a polynucleotide sequence used in Examples 3 and 4.

SEQ ID NO: 56 shows a polynucleotide sequence used in Examples 3 and 4. This sequence has an amino modifier attached to its 5' end.

SEQ ID NO: 57 shows a polynucleotide sequence used in Examples 3 and 4. This sequence has a phosphate attached to its 5' end and has four 2' O-methyl uracils and a thymine at the 3' end of the strand.

SEQ ID NO: 58 shows a polynucleotide sequence used in Examples 3 and 4.

SEQ ID NO: 59 shows a polynucleotide sequence used in Examples 3 and 4. This sequence has an amino modifier attached to its 5' end and two deoxyinosines at positions 36 and 38 indicated in the sequence by an I.

SEQ ID NO: 60 shows a polynucleotide sequence used in Examples 3 and 4. This sequence has a phosphate attached to its 5' end, two deoxyinosines at positions 1 and 3 (indicated in the sequence by an I) and has four 2' O-methyl uracils and a thymine at the 3' end of the strand.

SEQ ID NO: 61 shows a polynucleotide sequence used in Examples 3 and 4.

SEQ ID NO: 62 shows a polynucleotide sequence used in Examples 3 and 4.

SEQ ID NO: 63 shows a polynucleotide sequence used in Examples 3 and 4.

SEQ ID NO: 64 shows a polynucleotide sequence used in Examples 3 and 4.

SEQ ID NO: 65 shows a polynucleotide sequence used in Examples 3 and 4. This sequence has an amino modifier attached to its 5' end and two deoxyinosines at positions 37 and 38 indicated in the sequence by an I.

SEQ ID NO: 66 shows a polynucleotide sequence used in Examples 3 and 4. This sequence has a phosphate attached to its 5' end, two deoxyinosines at positions 2 and 3 (indicated in the sequence by an I) and has four 2' O-methyl uracils and a thymine at the 3' end of the strand.

SEQ ID NO: 67 shows a polynucleotide sequence used in Examples 3 and 4.

SEQ ID NO: 68 shows a polynucleotide sequence used in Examples 3 and 4.

SEQ ID NO: 69 shows a polynucleotide sequence used in Examples 3 and 4.

SEQ ID NO: 70 shows a polynucleotide sequence used in Examples 3 and 4.

SEQ ID NO: 71 shows a polynucleotide sequence used in Examples 3 and 4. This sequence has an amino modifier attached to its 5' end and three deoxyinosines at positions 36, 37 and 38 indicated in the sequence by an I.

SEQ ID NO: 72 shows a polynucleotide sequence used in Examples 3 and 4. This sequence has a phosphate attached to its 5' end, three deoxyinosines at positions 2, 3 and 4 (indicated in the sequence by an I) and has four 2' O-methyl uracils and a thymine at the 3' end of the strand.

SEQ ID NO: 73 shows a polynucleotide sequence used in Examples 3 and 4.

SEQ ID NO: 74 shows a polynucleotide sequence used in Examples 3 and 4.

SEQ ID NO: 75 shows a polynucleotide sequence used in Examples 3 and 4.

SEQ ID NO: 76 shows a polynucleotide sequence used in Examples 3 and 4.

SEQ ID NO: 77 shows a polynucleotide sequence used in Examples 3 and 4. This sequence has an amino modifier attached to its 5' end and two deoxyinosines at positions 36 and 37 indicated in the sequence by an I.

SEQ ID NO: 78 shows a polynucleotide sequence used in Examples 3 and 4. This sequence has a phosphate attached to its 5' end, two deoxyinosines at positions 3 and 4 (indicated in the sequence by an I) and has four 2' O-methyl uracils and a thymine at the 3' end of the strand.

SEQ ID NO: 79 shows a polynucleotide sequence used in Examples 3 and 4.

SEQ ID NO: 80 shows a polynucleotide sequence used in Examples 3 and 4.

SEQ ID NO: 81 shows a polynucleotide sequence used in Examples 3 and 4.

SEQ ID NO: 82 shows a typical polynucleotide sequence intermediate generated in Example 4.

SEQ ID NO: 83 shows a typical polynucleotide sequence generated in Example 4 (where X is an abasic residue): AACATCACCTAGCCTGCGAACGACAACGGAGT-GACXXTCCTXXTGAGTGACCTGTCT ACTGTAAGAT-GCAGTCTCTCGTGG. This sequence does not appear in the sequence listing because it includes abasic nucleotides.

SEQ ID NO: 84 shows a typical hairpin polynucleotide sequence used in Example 5. This sequence has a phosphate attached to its 5' end and a biotin group attached to the thymine at position 37.

SEQ ID NO: 85 shows a typical polynucleotide target sequence used in Example 5.

SEQ ID NO: 86 shows a polynucleotide sequence used in Example 5 This sequence has a phosphate attached to its 5' end.

SEQ ID NO: 87 shows a polynucleotide sequence used in Example 5. This sequence has a phosphate attached to its 5' end.

SEQ ID NO: 88 shows a polynucleotide sequence used in Example 5. This sequence has a phosphate attached to its 5' end.

SEQ ID NO: 89 shows a polynucleotide sequence used in Example 5. This sequence has a phosphate attached to its 5' end.

SEQ ID NO: 90 shows a typical polynucleotide sequence intermediate generated in Example 5. This sequence has a biotin group attached to the thymine at position 85.

SEQ ID NO: 91 shows a typical polynucleotide sequence generated in Example 5:

```
AAXXAATTXXGGGTXXGCATXXAAAGXXATATXXGCACXXACAGXXA

CAAXXCGTTCTGTTTATGTTTCTTGTTTGTTAGCCTT[(Bio)T]TT
```

-continued

GGCTAACAAACAAGAAACATAAACAGAACGGGTTGTTTCTGTTGGTG

CTGATATTGCTTTTGATGCCGACCCTAAATTTTTT

This sequence has a biotin group attached to the thymine at position 85. This sequence does not appear in the sequence listing because it includes abasic nucleotides.

SEQ ID NO: 92 shows a typical hairpin sequence used in Example 6. This sequence has a phosphate attached to its 5' end.

SEQ ID NO: 93 shows a typical hairpin sequence used in Example 6. This sequence has a phosphate attached to its 5' end.

SEQ ID NO: 94 shows a typical sense target sequence used in Example 6.

SEQ ID NO: 95 shows a typical antisense target sequence used in Example 6.

SEQ ID NO: 96 shows a typical primer sequence used in Example 6.

SEQ ID NO: 97 shows a typical oligonucleotide sequence used in Example 6. This sequence has a phosphate attached to its 5' end.

SEQ ID NO: 98 shows a typical oligonucleotide sequence used in Example 6. This sequence has a phosphate attached to its 5' end.

SEQ ID NO: 99 shows a typical oligonucleotide sequence used in Example 6. This sequence has a phosphate attached to its 5' end.

SEQ ID NO: 100 shows a typical oligonucleotide sequence used in Example 6. This sequence has a phosphate attached to its 5' end.

SEQ ID NO: 101 shows a typical oligonucleotide sequence used in Example 6. This sequence has a phosphate attached to its 5' end.

SEQ ID NO: 102 shows a typical oligonucleotide sequence used in Example 6. This sequence has a phosphate attached to its 5' end.

SEQ ID NO: 103 shows a typical oligonucleotide sequence used in Example 6. This sequence has a phosphate attached to its 5' end.

SEQ ID NO: 104 shows a typical oligonucleotide sequence used in Example 6. This sequence has a phosphate attached to its 5' end.

SEQ ID NO: 105 shows a typical oligonucleotide sequence used in Example 6. This sequence has a phosphate attached to its 5' end.

SEQ ID NO: 106 shows a typical oligonucleotide sequence used in Example 6. This sequence has a phosphate attached to its 5' end.

SEQ ID NO: 107 shows a typical oligonucleotide sequence used in Example 6. This sequence has a phosphate attached to its 5' end.

SEQ ID NO: 108 shows a typical hairpin sequence used in Example 6.

SEQ ID NOs: 109 to 138 show the sequences shown in claims 8 and 10. In these sequences, Z is shown as inosine because this is the only universal nucleotide which appears in Annex C, Appendix 2, Table 2 of WIPO's Standard ST.25.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polynucleotide" includes "polynucleotides", reference to "an oligomer" includes two or more such oligomers, reference to "a transmembrane protein pore" includes two or more such pores, and the like.

All publications, patents and patent applications cited herein, whether supra or infra, are hereby incorporated by reference in their entirety.

Modification Method of the Invention

The present invention provides a method of modifying a template polynucleotide for characterisation, such as for sequencing. The template polynucleotide is the polynucleotide that will ultimately be characterised, or sequenced, in accordance with the invention. This is discussed in more detail below.

The method involves the formation of one or more modified polynucleotides. The one or more modified polynucleotides are easier to characterise than the template polynucleotide, especially using strand sequencing. The one or more modified polynucleotide may themselves be characterised in order to facilitate the characterisation of the template polynucleotide.

An essential component of sequencing polynucleotides using strand sequencing is the discrimination of nucleotides as the polynucleotide polymer is moved through the pore. In the past, to achieve nucleotide discrimination the polynucleotide has been passed through a mutant of hemolysin. This has provided current signatures that have been shown to be sequence dependent. It has also been shown that a large number of nucleotides contribute to the observed current, making a direct relationship between observed current and polynucleotide sequence challenging. In addition, it has been observed that when polynucleotides are moved through a pore, some current states show high variance. It has also been shown that some mutant hemolysin pores exhibit higher variance than others.

Pores produced from mutated MspA monomers display an increased current range, which makes it easier to discriminate between different nucleotides, and a reduced variance of states, which increases the signal-to-noise ratio. In addition, the number of nucleotides contributing to the current as the polynucleotide moves through pores constructed from the MspA mutants is decreased. This makes it easier to identify a direct relationship between the observed current as the polynucleotide moves through the pore and the polynucleotide sequence. The signals generated using such pores may still be quite complex and so it remains challenging to sequence certain polynucleotides.

The method of the invention is particularly advantageous for strand sequencing because it simplifies the signal received from the pore. The template strand is not sequenced directly using strand sequencing, but is instead converted into one or more modified polynucleotides. As discussed above, the method of the invention may produce a plurality of modified polynucleotides which are complementary to the template polynucleotide at differing positions and which contain universal or abasic nucleotides at other positions. The modified polynucleotides that are characterized, such as sequenced, preferably contain abasic nucleotides at the other positions either because the oligomers used in the invention contain such nucleotides or because the oligomers contain universal nucleotides and the nucleobases are selectively removed from the universal bases after ligation of the modified polynucleotide. As discussed in more detail below, the positions of the universal or abasic nucleotides in the modified polynucleotide(s) may be predicted.

It is easier to sequence the modified polynucleotide(s) than it is to sequence the template polynucleotide using strand sequencing for various reasons. For instance, the separation of the complementary nucleotides by abasic nucleotides will mean that fewer complementary nucleotides contribute to the observed current. This will make the signal received from the pore less complex.

The introduction of universal or abasic nucleotides also improves the ability of the pore to read homopolymer regions during strand sequencing. For instance, if the read head of the pore gives a signal from three nucleotides, then that limits your ability to read homopolymers sections longer than 3 nucleotides. However, longer homopolymers, such as six nucleotides, can be made to look like three nucleotides using the invention (by inserting three inosine or abasic nucleotides) and then the six nucleotide homopolymer region can be sequenced with more confidence.

In addition, the abasic nucleotoides will produce a much reduced signal compared with the complementary nucleotides because of their lack of nucleobases. For instance, in strand sequencing, abasics will allow more current to flow through the pore because of their lack of nucleobases. Hence, it will be easier to identify the complementary nucleotides. It is easier to sequence the modified polynucleotide(s) than it is to sequence the template polynucleotide using strand sequencing even if the modified polynucleotide(s) contain universal nucleotides. For instance, if only one universal nucleotide is used in the oligomers, the universal nucleotide will give a known and substantially constant signal when it passes through the pore. This will make it easier to identify the complementary nucleotides in the modified polynucleotide(s) because their signals will differ from the universal nucleotide background signal.

In some instances, the pattern of abasic and complementary nucleotides may be predicted, for instance by using oligomers that are all the same length and all have the same repeating pattern of abasic nucleotide to complementary nucleotide ($Z_X N_Y$ and/or $N_Y Z_X$ as defined below). This further facilitates the identification of the complementary nucleotides using strand sequencing because it can be predicted when they will be largely responsible for the signal coming from the pore. For instance, the use of a population of ZZN oligomers, it can be predicted that the complementary nucleotides will be at positions 3, 6, 9, 12, 15, 17 etc. The strand sequencing method can therefore be designed to focus on the signals obtained at each of these positions.

The presence of abasic residues in the modified polynucleotide(s) (because either the oligomers contain abasic nucleotides or the nucleobases have been selectively removed from the universal nucleotides) may also facilitate their handling during characterisation, particularly using strand sequencing. If the modified polynucleotide is double stranded, the presence of abasic nucleotides in one strand will mean that the two strands dehybridise more easily. Such dehybridisation facilitates characterisation because current strand sequencing methods prefer single stranded polynucleotides. Similarly, if the modified polynucleotide is single stranded, the presence of abasic nucleotides will reduce the potential of the polynucleotide to form secondary structure. In strand sequencing, it is preferred if the single stranded polynucleotide is substantially linear.

The method of the invention also has other advantages. For instance, it is a straightforward method that requires the components to be mixed and incubated at a constant temperature for a suitable length of time.

Template Polynucleotide

The method of the invention modifies a template polynucleotide for characterisation. The template polynucleotide is the polynucleotide that will ultimately be characterised, or sequenced, in accordance with the invention. It may also be called the target polynucleotide or the polynucleotide of interest.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the template polynucleotide can be oxidized or methylated. One or more nucleotides in the template polynucleotide may be damaged. For instance, the polynucleotide may comprise a pyrimidine dimer. Such dimers are typically associated with damage by ultraviolet light and are the primary cause of skin melanomas. One or more nucleotides in the template polynucleotide may be modified, for instance with a label or a tag. Suitable labels are described below. The template polynucleotide may comprise one or more spacers.

A nucleotide typically contains a nucleobase, a sugar and at least one phosphate group. The nucleobase is typically heterocyclic. Nucleobases include, but are not limited to, purines and pyrimidines and more specifically adenine (A), guanine (G), thymine (T), uracil (U) and cytosine (C). The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the template polynucleotide may be attached to each other in any manner. The nucleotides are typically attached by their sugar and phosphate groups as in nucleic acids. The nucleotides may be connected via their nucleobases as in pyrimidine dimers.

The template polynucleotide may be single stranded or double stranded. At least a portion of the polynucleotide is preferably double stranded.

The template polynucleotide can be a nucleic acid, such as deoxyribonucleic acid (DNA) or ribonucleic acid (RNA). The template polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

The template polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The template polynucleotide is typically present in any suitable sample. The invention is typically carried out on a sample that is known to contain or suspected to contain the template polynucleotide. Alternatively, the invention may be carried out on a sample to confirm the identity of one or more template polynucleotides whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being used in the invention, for example by centrifugation or by passage through a membrane that filters out unwanted molecules or cells, such as red blood cells. The sample may be measured immediately upon being taken. The sample may also be typically stored prior to assay, preferably below −70° C.

Hybridisation Conditions

The template polynucleotide is contacted with a population of nucleotide oligomers under conditions in which the oligomers can hybridise to the polynucleotide. The oligomers are defined below.

Conditions that permit the hybridisation are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-lnterscience, New York (1995)). Hybridisation can be carried out under low stringency conditions, for example in the presence of a buffered solution of 30 to 35% formamide, 1 M NaCl and 1% SDS (sodium dodecyl sulfate) at 37° C. followed by a wash in from 1× (0.1650 M Na+) to 2× (0.33 M Na+) SSC (standard sodium citrate) at 50° C. Hybridisation can be carried out under moderate stringency conditions, for example in the presence of a buffer solution of 40 to 45% formamide, 1 M NaCl, and 1% SDS at 37° C., followed by a wash in from 0.5× (0.0825 M Na+) to 1× (0.1650 M Na+) SSC at 55° C. Hybridisation can be carried out under high stringency conditions, for example in the presence of a buffered solution of 50% formamide, 1 M NaCl, 1% SDS at 37° C., followed by a wash in 0.1× (0.0165 M Na+) SSC at 60° C.

Preferred conditions are those described in the Example. In particular, the conditions are preferably 10 uM oligomers in 10 mM Tris-HCl, 50 mM NaCl, pH 7 and heat to 98° C. before cooling to 18° C. at 2° C. per minute.

Population of Oligomers

All of the oligomers in the population have from 2 to 16 nucleotides. All of the oligomers in the population have 2, 3, 4, 5, 6, 7, 8, 9, 10, 11, 12, 13, 14, 15 or 16 nucleotides. The oligomers in the population may have different lengths. All of the oligomers in the population preferably have the same length. By using a population of oligomers all having the same length, the pattern of abasic and complementary nucleotides in the modified polynucleotide(s) may be predicted.

All of the oligomers in the population comprise, or preferably consist of, the same pattern of one or more instances of $Z_X N_Y$ and/or $N_Y Z_X$. The pattern may be regular or irregular as discussed in more detail below. All of the oligomers in the population may comprise, or preferably consist of, one or more instances of $Z_X N_Y$. All of the oligomers in the population may comprise, or preferably consist of, one or more instances of $N_Y Z_X$. All of the oligomers in the population may comprise, or preferably consist of, one or more instances of $Z_X N_Y$ and $N_Y Z_X$. All of the oligomers preferably comprise, or more preferably consist of, 2, 3, 4, 5, 6, 7 or 8 instances of $Z_X N_Y$ and/or $N_Y Z_X$.

Z is a universal nucleotide and/or an abasic nucleotide. If there are two or more instances of Z in the oligomers, the oligomers may comprise one or more universal nucleotides and one or more abasic nucleotides. More preferably, all of the instances of Z in the oligomers are universal nucleotides or all of instances of Z in the oligomers are abasic nucleotides. Even more preferably, all of the instances of Z in the oligomers are the same universal nucleotide or the same abasic nucleotide.

A universal nucleotide is one which will hybridise to some degree to all of the nucleotides in the template polynucleotide. A universal nucleotide is preferably one which will hybridise to some degree to nucleotides comprising the nucleosides adenosine (A), thymine (T), uracil (U), guanine (G) and cytosine (C). The universal nucleotide may hybridise more strongly to some nucleotides than to others. For instance, a universal nucleotide (I) comprising the nucleoside, 2'-deoxyinosine, will show a preferential order of pairing of I-C>I-A>I-G approximately=I-T. For the purposes of the invention, it is only necessary that the universal nucleotide used in the oligomers hybridises to all of the nucleotides in the template polynucleotide.

The universal nucleotide preferably comprises one of the following nucleobases: hypoxanthine, 4-nitroindole, 5-nitroindole, 6-nitroindole, 3-nitropyrrole, nitroimidazole, 4-nitropyrazole, 4-nitrobenzimidazole, 5-nitroindazole, 4-aminobenzimidazole or phenyl (C6-aromatic ring The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside or phenyl C-2'-deoxyribosyl nucleoside. The universal nucleotide is most preferably comprises 2'-deoxyinosine.

If there are two or more universal nucleotides in each oligomer, the universal nucleotides may be different from one another. If there are two or more universal nucleotides in each oligomer, the universal nucleotides are preferably the same. All of the instances of Z in the population of oligomers are preferably the same universal nucleotide.

An abasic nucleotide is a nucleotide that lacks a nucleobase. The abasic nucleotide typically contains a sugar and at least one phosphate group. The sugar is typically a pentose sugar, such as ribose and deoxyribose. The abasic nucleotide is typically an abasic ribonucleotide or an abasic deoxyribonucleotide. The abasic nucleotide typically contains a monophosphate, diphosphate or triphosphate. Phosphates may be attached on the 5' or 3' side of an abasic nucleotide.

Abasic nucleotides will not hybridise to the nucleotides in the template polynucleotide because they lack a nucleobase. If such nucleotides are used in the oligomers, it will be the N (or complementary) nucleotides in the oligomers that are responsible for the hybridisation of the oligomers to the template polynucleotide. To ensure that the oligomers effectively hybridise to the template polynucleotide, if Z is an abasic nucleotide, then the ratio of X to Y is at least 1:2, more preferably at least 1:3 and even more preferably at least 1:4. If Z is an abasic nucleotide, then X is preferably 1, 2 or 3. If Z is an abasic nucleotide, then X is preferably not 4 or more.

If there are two or more abasic nucleotides in each oligomer, the abasic nucleotides may be different from one another. If there are two or more abasic nucleotides in each oligomer, the abasic nucleotides are preferably the same. All of the instances of Z in the population of oligomers are preferably the same abasic nucleotide.

The use of (a) universal nucleotides or (b) abasic nucleotides in accordance with the invention each has its advantages. Universal nucleotides hybridise to the nucleotides in the template polynucleotide and thereby ensure that oligomers in the population effectively hybridise to the template polynucleotide. However, the universal nucleotides comprise nucleobases which makes it more difficult to distinguish them from the complementary nucleotides when characterising the modified polynucleotide(s), especially when using strand sequencing. In contrast, abasic nucleotides will not hybridise to the nucleotides in the template polynucleotide, but can be more easily distinguished from the complementary nucleotides in the modified polynucleotide(s) because (in both instances) they lack a nucleobase.

If Z is a universal nucleotide, the method preferably further comprises (c) selectively removing the nucleobases from the universal nucleotides in the ligated polynucleotide and thereby providing a modified polynucleotide for characterisation. This combines the advantages of each type of nucleotide; the presence of universal nucleotides in the oligomers means that the oligomers effectively hybridise to the template polynucleotide and the selective removal of nucleobases from the universal nucleotides in the ligated polynucleotide(s) effectively replaces them with abasic nucleotides which can be more easily distinguished from the complementary nucleotides in the modified polynucleotide(s).

Selective removal of the nucleobases from the universal nucleotides means that the nucleobases are removed from the universal nucleotides in the ligated polynucleotide (i.e. the Zs), but not from the complementary nucleotides in the ligated polynucleotide (i.e. not from the Ns). The nucleobases may be selectively removed using any method known in the art. For instance, certain DNA repair proteins, such as human alkyladenine DNA glycosylase (hAAG), are capable of selectively removing 3-methyl adenine, 7-methyl guanine, 1, N6-ethenoadenine and hypoxanthine from nucleotides.

N is a nucleotide which is complementary to one of the nucleotides in the template polynucleotide. The nucleotides in the template polynucleotide are discussed above. It is straightforward for a person skilled in the art to identify nucleotides that are complementary to those nucleotides. A nucleotide is complementary to another nucleotide if it hybridises through base pairing, preferably Watson and Crick base pairing, to the nucleotide. A complementary nucleotide may hybridise to other nucleotides with which it is not complementary, but to a smaller degree than it hybridises to the nucleotide with which it is complementary. N preferably comprises the nucleobases adenine (A), uracil (U), guanine (G) or cytosine (C). Alternatively, N preferably comprises the nucleobases A, thymine (T), G or C. A is complementary to T or U and vice versa. G is complementary to C and vice versa.

For $Z_XN_Y$ and/or $N_YZ_X$, X is 1, 2, 3 or 4 and Y is 1, 2, 3 or 4. The pattern of $Z_XN_Y$ and/or $N_YZ_X$ is preferably regular. This allows the position of the universal nucleotides or abasic nucleotides in the modified polynucleotide(s) to be predicted. In particular, X and/or Y are preferably the same in different instances of $Z_XN_Y$ and/or $N_YZ_X$. X and Y are more preferably the same in different instances of $Z_XN_Y$ and/or $N_YZ_Y$. Preferably, in at least one instance of $Z_XN_Y$ and/or $N_YZ_X$, X is 1 and Y is 1; X is 2 and Y is 2; X is 3 and Y is 3; or X is 4 and Y is 4.

All of the oligomers preferably have a regular pattern because they comprise, or more preferably consist of, one or more instances of $Z_XN_Y$ or one or more instances of $N_YZ_X$ and each of the one or more instances of $Z_XN_Y$ or each of the one or more instances of $N_YZ_X$ are identical in terms of X and Y. All of the oligomers in the population preferably comprise, or more preferably consist of:

(a) ZN-ZN-ZN-ZN-ZN-ZN;
(b) NZ NZ NZ NZ NZ NZ;
(c) ZZNN-ZZNN-ZZNN;
(d) NNZZ-NNZZ-NNZZ;
(e) ZZZNNN-ZZZNNN;
(f) NNNZZZ-NNNZZZ;
(g) ZZZZNNNN-ZZZZNNNN;
(h) NNNNZZZZ-NNNNZZZZ;
(i) ZN-ZN-ZN-ZN;
(j) NZ-NZ-NZ-NZ;
(k) ZZNN-ZZNN;
(l) NNZZ-NNZZ;
(m) ZZZZNNNN;
(n) NNNNZZZZ;
(o) ZZN-ZZN-ZZN;
(p) NNZ-NNZ-NNZ;
(q) ZZZN-ZZZN-ZZZN-ZZZN;
(r) NNNZ-NNNZ-NNNZ-NNNZ;
(s) ZZZN-ZZZN-ZZZN; or
(t) NNNZ-NNNZ-NNNZ.

In the above, "-" is being used to separate the repeating units of $Z_XN_Y$ or $N_YZ_X$. The same applied below.

The pattern of $Z_XN_Y$ and/or $N_YZ_X$ may be irregular. In particular, X and/or Y are preferably different in different instances of $Z_XN_Y$ and/or $N_YZ_X$. X and Y are more preferably different in different instances of $Z_XN_Y$ and/or $N_YZ_X$. Preferably, in at least one instance of $Z_XN_Y$ and/or $N_YZ_X$, X is 2 and Y is 1; X is 1 and Y is 2; X is 3 and Y is 1; or X is 1 and Y is 3. All of the oligomers preferably have an irregular pattern because they comprise, or more preferably consist of, one or more instances of $Z_XN_Y$ and one or more instances of $N_YZ_X$ and each of the one or more instances of $Z_XN_Y$ and/or each of the one or more instances of $N_YZ_X$ are different in terms of X and Y. All of the oligomers in the population preferably comprise, or more preferably consist of:

(u) NZ-ZNN-ZZNN-ZZN;
(v) ZN-NZZ-NNZZ-NNZ;
(w) NNZZ-ZZNN-NNNZZZ-ZNN;
(x) ZZNN-NNZZ-ZZZNNN-NZZ;
(y) NNZZ-ZZNN;
(z) ZZNN-NNZZ;
(aa) NZZ-NNZ-ZNN-ZZN;
(bb) ZNN-ZZN-NZZ-NNZ;
(cc) NZZ-NNZ-ZN; or
(dd) ZNN-ZZN-NZ.

The population comprises every possible combination of nucleotides N which are complementary to all of the nucleotides in the template polynucleotide. This means that the oligomers will hybridise to the most, if not all, of the template polynucleotide whatever its sequence. For instance, if N comprises the nucleobases adenine (A), uracil (U), guanine (G) or cytosine (C), the population comprises every possible combination of A, U, G and C. Similarly, if N comprises the nucleobases A, thymine (T), G or C, the population comprises every possible combination of A, T, G and C.

It is straightforward to design and obtain a population of oligomers having the requisite combination. For instance, if all of the oligomers in the population comprise or consist of ZN and N is A, T, G or C, then the populations comprises ZA, ZT, ZG and ZC. Similarly, if all of the oligomers in the population comprise or consist of ZNZN and N is A, T, G or C, then the population comprises ZAZA, ZAZT, ZAZG, ZAZC, ZTZA, ZTZT, ZTZG, ZTZC, ZGZA, ZGZT, ZGZG, ZGZC, ZCZA, ZCZT, ZCZG and ZCZC. Once the generic formula, such as ZN or ZNZN, has been designed, populations comprising all of the possible combinations of N are commercially available, for instance from Intergrated DNA Technologies (IDT), Sigma and Invitrogen.

The oligomers are capable of being ligated together in accordance with the invention. All of the oligomers in the population preferably have a phosphate group or an adenylate group at the 5' end.

Ligating the Oligomers

The hybridised oligomers may be ligated together using any method known in the art. The oligomers are preferably ligated using a ligase, such as T4 DNA ligase, E. coli DNA ligase, Taq DNA ligase, Tma DNA ligase and 9° N DNA ligase.

The oligomers may also be chemically ligated if reactive groups are present on the ends of the oligomers. In such embodiments, steps need to be taken to prevent the oligomers from ligating to each other in solution.

The ligation reaction is typically initiated using a primer. This is discussed in more detail below.

Single Stranded Template Polynucleotide

The template polynucleotide may be single stranded. If the template polynucleotide is single stranded, the method preferably further comprises before step (a) ligating a hairpin adaptor to one end of the template polynucleotide such that the ligated hairpin adaptor provides a degenerate overhang and wherein step (b) comprises ligating together the oligomers that hybridise to the polynucleotide using the degenerate overhang as a primer. The degenerate overhang typically hybridises with the end of template polynucleotide over which it hangs to form a short region of double stranded polynucleotide. A ligase may then bind to this double stranded region and begin to ligate the hybridised oligomers.

Suitable hairpin adaptors can be designed using methods known in the art. The hairpin loop may be any length. The hairpin loop is typically 50 or fewer bases, such as 40 or fewer bases, 30 or fewer bases, 20 or fewer bases or 10 or fewer bases, in length. The hairpin loop is preferably from about 1 to 50, from 2 to 40 or from 6 to 30 bases in length. Longer lengths of the hairpin loop, such as from 15 to 50 bases, are preferred if the loop is involved in the differential selectability of the adaptor. Similarly, shorter lengths of the hairpin loop, such as from 1 to 5 bases, are preferred if the loop is not involved in the selectable binding as discussed below.

The degenerate overhang may comprise Z and/or N as defined above. The degenerate overhang preferably comprises universal nucleotides. Since universal nucleotides hybridise with any nucleotide, this will allow the degenerate overhang to hybridise with the sequence at the relevant end of the template polynucleotide. The degenerate overhang may comprise N, but the extent of hybridisation will depend on the sequence of the overhang and the sequence at the relevant end of the template polynucleotide.

The degenerate overhang can be any length as long as it acts as a primer for ligation. The overhang is preferably from about 3 to about 6 nucleotides in length, such as 3, 4, 5 or 6 nucleotides in length. The overhang may be longer if it is made up of only universal nucleotides.

The hairpin adaptor may be ligated to either end of the template polynucleotide, i.e. the 5' or the 3' end. The hairpin adaptor may be ligated to the template polynucleotide as discussed above.

The hairpin adaptor preferably comprises a selectable binding moiety. This allows the template polynucleotide and the modified polynucleotide to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a nucleic acid sequence, antibodies, antibody fragments, such as Fab and ScSv, antigens, nucleic acid binding proteins, poly histidine tails and GST tags. The most preferred selective binding moieties are biotin and a selectable nucleic acid sequence. Biotin specifically binds to a surface coated with avidins. Selectable nucleic acid sequences specifically bind (i.e. hybridize) to a surface coated with homologus sequences. Alternatively, selectable nucleic acid sequences specifically bind to a surface coated with nucleic acid binding proteins.

The hairpin adaptor and/or the selectable binding moiety may comprise a region that can be cut, nicked, cleaved or hydrolysed. Such a region can be designed to allow the modified polynucleotide and temple polynucletide (which may be attached together via the hairpin adaptor) to be removed from the surface to which it is bound following purification or isolation. It can also be designed to allow the modified polynucleotide to be separated from the template polynucleotide. Suitable regions are known in the art. Suitable regions include, but are not limited to, an RNA region, a region comprising desthiobiotin and streptavidin, a disulphide bond and a photocleavable region.

If the template polynucleotide is single stranded, the method may comprise (i) ligating a first hairpin adaptor to one end of the template polynucleotide such that the ligated first hairpin adaptor provides a first degenerate overhang, (ii) carrying out step (a) as defined above, (iii) carrying out step (b) as defined above wherein the ligation uses the first degenerate overhang as a primer, (iv) separating the ligated polynucleotide from the template polynucleotide, (v) ligating a second hairpin adaptor to the other end of the template polynucleotide such that the second ligated hairpin adaptor provides a second degenerate overhang, (vi) repeating step (a) as defined above, (vii) repeating step (b) as defined above wherein the ligation proceeds in the opposite direction along the template polynucleotide and uses the second degenerate overhang as a primer and thereby providing a modified polynucleotide for characterisation. The resulting polynucleotide comprises two modified polynucleotides, one of which is attached to one end of the template polynucleotide by the first hairpin adaptor and the other of which is attached to the other end of the template polynucleotide by the second hairpin adaptor. The modified polynucleotide that is ligated second may remain hybridised to the template polynucleotide or may be separated from it.

The first and second hairpin adaptors may be any of those described above. They may be the same or different.

The first and second degenerate overhangs may be any of those described above. They may be the same or different.

The modified polynucleotide(s) and the template polynucleotide may be separated using any method known in the art. For instance, they may be separated by a polynucleotide binding protein or using conditions which favour dehybridsation (examples of conditions which favour dehybridisation include, but are not limited to, high temperature, high pH and the addition of agents that can disrupt hydrogen bonding or base pairing, such as formamide and urea). Modified polynucleotides that contain abasic nucleotides will separate more easily from the template polynucleotide.

Double Stranded Template Polynucleotide

The template polynucleotide may be double stranded. If the template polynucleotide is double stranded, the method preferably further comprises before step (a) ligating a first hairpin adaptor to one end of the template polynucleotide and ligating a second hairpin adaptor to the other end of the template polynucleotide to form a circular polynucleotide construct.

Suitable hairpins can be designed as described above. The hairpin loops may be any length as described above. The first hairpin adaptor may be ligated to either end of the template polynucleotide, i.e. the 5' or the 3' end, and the second hairpin adaptor is ligated to the other end. The hairpin adaptors may be ligated to the template polynucleotide as discussed above.

The second hairpin adaptor preferably comprises a primer hybridisation region and an abasic region comprising one or more abasic nucleotides and step (b) preferably comprises ligating together the oligomers that hybridise to the circular polynucleotide construct using the second hairpin adaptor as the prime for ligation and thereby producing a polynucleotide circular construct that is substantially double stranded. The primer hybridisation may be any length and may comprise any sequence of N as defined above. The second hairpin adaptor may be used as the prime for ligation by hybridising a complementary primer to the primer hybridisation region and thereby producing a short region of double stranded polynucleotide to which the ligase can bind and initiate ligation. The abasic region may comprise any number of abasic nucleotides, but typically comprise more than 4, such as 5, 6, 7, 8, 9, 10 or more. This region typically terminates ligation. Since the oligomers will have hybridised to both strands of the double stranded template polynucleotide, the result of ligation will be a polynucleotide construct that is itself substantially double stranded.

The second hairpin adaptor further comprises a region at which the hairpin can be cut, nicked, cleaved or hydrolysed and the method further comprises before step (c) cutting the second hairpin adaptor to open the circular polynucleotide construct and produce a double stranded polynucleotide. Suitable regions are discussed above.

The first or second hairpin adaptor prefereably comprises a selectable binding moiety as discussed above.

Repetitive Method

As discussed above, the method of the invention preferably facilitates characterisation of the template polynucleotide by converting it into a plurality of modified polynucleotides which are complementary to the template polynucleotide at differing positions and which contain universal or abasic nucleotides at other positions. It is easier to characterise the modified polynucleotides than it is to sequence the template polynucleotide using strand sequencing for the reasons discussed above. It is preferred that the position of the universal or abasic nucleotides may be predicted.

The method of the invention preferably further comprises as step (d) repeating steps (a) to (c) at least once such that the ligation in each repetition begins at a different nucleotide on the template polynucleotide and thereby producing a plurality of different modified polynucleotides. Steps (a) and (b) are typically repeated sufficient times that the plurality of different modified polynucleotides as a whole comprises a complementary nucleotide at every position of the template polynucleotide. This allows the sequence of the template polynucleotide to be reconstructed from characterisation of the plurality of different modified polynucleotides. Analysis of each complementary nucleotide in the plurality of modified nucleotides reveals a sequence that is complementary to the template polynucleotide. The number of repetitions required will depend on the ratio of Z to N (i.e. the ratio of X to Y) in the population of oligomers. If X (i.e. the number Z nucleotides) in each oligomer is the same, the number of repetitions required typically corresponds to the value of X.

Two representations of the repetitive method are given below.

Representation A

Template polynucleotide 1 (SEQ ID NO: 24) is shown in bold. The oligomers each contain ZN and are alternately underlined in 2 and 3 (SEQ ID NOs: 25 and 26). These oligomers are ligated to form modified polynucleotides 2 and 3 where the ligation has started at different positions. Sequences 2a and 3a (SEQ ID NOs: 27 and 28) correspond to 2 and 3 respectively with the nucleobases removed from all Zs. Sequencing of both 2 and 3 (or 2a and 3a) reveals sequence 4 (SEQ ID NO: 29) which is complementary 1.

| | |
|---|---|
| 1 | ATGCCATGATACTTACCATTAGGCCACACG |
| 2 | ZAZGZTZCZAZGZAZGZTZAZCZGZTZTZC |
| 2a | A G T C A G A G T A C G T T C |
| 1 | ATGCCATGATACTTACCATTAGGCCACACG |

```
    3          ZTZCZGZAZTZTZAZTZGZAZTZCZGZGZG

3a         T C G A T T A T G A T C G G

4          TACGGTACTATGAATGGTAATCCGGTGTGC
```

Hence, in this representation, only one repetition (two modified polynucleotides) is needed to reconstruct the sequence of the template polynucleotide.

Representation B

The (same) template polynucleotide 1 (SEQ ID NO: 24) is shown in bold. The oligomers each contain ZZN and are alternately underlined. These oligomers are ligated to form the modified polynucleotides 5, 6 and 7 (SEQ ID NOs: 30, 31 and 32) where the ligation has started at different positions. Sequencing of 5 to 7 reveals sequence 4 (SEQ ID NO: 29) which is complementary to 1.

```
    1          ATGCCATGATACTTACCATTAGGCCACACG

5          ZZCZZTZZTZZGZZTZZTZZTZZGZZGZZC

6          ZZAZZGZZCZZTZZAZZGZZAZZCZZTZZG

7          ZZTZZGZZAZZAZZAZZGZZAZZCZZGZZT

4          TACGGTACTATGAATGGTAATCCGGTGTGC
```

Hence, in this representation, two repetitions (three modified polynucleotides) are needed to reconstruct the sequence of the template polynucleotide.

It is straightforward using methods known in the art to design the method such that ligation starts at a different position in each repetition. If the template polynucleotide is single stranded, the method preferably further comprises before step (a) in each repetition ligating a hairpin adaptor to one end of the template polynucleotide such that the ligated hairpin adaptor provides a degenerate overhang, step (b) preferably comprises ligating together the oligomers that hybridise to the polynucleotide using the degenerate overhang as a primer and the degenerate overhang is preferably a different length in each repetition. For instance, representation A could be repeated as follows.

Representation C

The (same) template polynucleotide 1 (SEQ ID NO: 24) is shown in bold. The oligomers (not bold) each contain ZN and are alternately underlined. A hairpin adaptor having a degenerate overhang of three Zs (in bold for polynucleotide 8) or two Zs (for polynucleotide 9) ensures that ligation starts at different positions for polynucleotides 8 and 9 (SEQ ID NOs: 33 and 34). Since the first three nucleotides of polynucleotide 1 is the start codon (ATG), the overhangs for 8 and 9 (Zs in bold) could be TAC and TA respectively. Sequencing of 8 and 9 reveals polynucleotide 10 (SEQ ID NO: 35) which is complementary to 1 without the start codon.

```
    1          ATGCCATGATACTTACCATTAGGCCACACG

8          ZZZZGZAZTZTZAZTZGZAZTZCZGZGZGZC

9          ZZZGZTZCZAZGZAZGZTZAZCZGZTZTZC

10         GGTACTATGAATGGTAATCCGGTGTGC
```

If the template polynucleotide is double stranded, the method preferably further comprises before step (a) ligating a first hairpin adaptor to one end of the template polynucleotide and ligating a second hairpin adaptor to the other end of the template polynucleotide to form a circular polynucleotide construct, step (b) preferably comprises ligating together the oligomers that hybridise to the circular polynucleotide construct using the second hairpin adaptor as the prime for ligation and the length of the first hairpin adaptor is preferably different in each repetition. Since each first hairpin is a different length in each repetition, ligation of the hybridised oligomers after the first hairpin will start at different positions. This is represented below.

Representation D

The (same) template polynucleotide 1 (SEQ ID NO: 24) is shown in bold. It is one strand of a double stranded polynucleotide. X=nucleotides of the hairpin adaptor. The adaptor in 1a (SEQ ID NO: 36) is one nucleotide longer than the adaptor in 1b (SEQ ID NO: 37). The oligomers each contain ZN and are alternately underlined in 11 and 12 (SEQ ID NOs: 38 and 39). These oligomers are ligated to form modified polynucleotides 11 and 12 where the ligation has started at different positions. Sequencing of both 11 and 12 reveals sequence 4 (SEQ ID NO: 29) which is complementary 1.

```
    1a         XXXATGCCATGATACTTACCATTAGGCCACACG

11         ZNZTZCZGZAZTZTZAZTZGZAZTZCZGZGZCZA

1b         XXATGCCATGATACTTACCATTAGGCCACACG

12         ZNZAZGZTZCZAZGZAZGZTZAZCZGZTZTZC

4          TACGGTACTATGAATGGTAATCCGGTGTGC
```

An alternative method is to contact the template polynucleotide with a population of di- or tri-nucleotide oligomers as defined above (i.e. $Z_XN_Y$ and/or $N_YZ_X$ where X is 1 or 2 and Y is 1 or 2) and a polymerase such that the polymerase generates a polynucleotide which is complementary to the template polynucleotide and which contains universal and/or abasic nucleotides.

Products of the Invention

The invention also provides a polynucleotide modified using a method of the invention. The modified polynucleotide of the invention comprises nucleotides complementary to the template polynucleotide at some positions and universal or abasic nucleotides at the other positions. The pattern of complementary nucleotides and universal or abasic nucleotides will of course depend on the oligomers used in the method of the invention.

The modified polynucleotide may come in a variety of forms depending on which method of the invention is used. Possible forms, include, but are not limited to, the following:
  a modified polynucleotide hybridised to the template polynucleotide;
  a modified polynucleotide separated from the template polynucleotide;
  a modified polynucleotide hybridised to the template polynucleotide and attached to the template polynucleotide using a hairpin adaptor at one or both ends;
  a modified polynucleotide separated from the template polynucleotide and attached to the template polynucleotide using a hairpin adaptor;
  a modified polynucleotide in isolation (i.e. separated from the template polynucleotide) and attached to the whole or part of a hairpin adaptor;
  two modified polynucleotides each hybridised to one strand of a double stranded polynucleotide; and two modified polynucleotides separated from the double stranded template polynucleotide;

a modified polynucleotide hybridised to a double stranded polynucleotide whose strands are attached together using a hairpin adaptor at one or both ends.

The invention also provides a plurality of polynucleotides modified using the repetitive method of the invention. The plurality of polynucleotides may be in any of the forms discussed above. The plurality of polynucleotides as a whole preferably includes at least one nucleotide that is complementary to each of the nucleotides in the template polynucleotide.

The modified polynucleotide(s) may be isolated, substantially isolated, purified or substantially purified. A modified polynucleotide is isolated or purified if it is completely free of any other components, such as the template polynucleotide, lipids or pores. A modified polynucleotide is substantially isolated if it is mixed with carriers or diluents which will not interfere with its intended use. For instance, a modified polynucleotide is substantially isolated or substantially purified if it is present in a form that comprises less than 10%, less than 5%, less than 2% or less than 1% of other components, such as lipids or pores.

The invention also provides a population of nucleotide oligomers, wherein all of the oligomers in the population (i) have from 2 to 16 nucleotides and (ii) comprise or consist of the same pattern of one or more instances of $Z_X N_Y$ and/or $N_Y Z_X$ where Z is a universal nucleotide and/or an abasic nucleotide, N is a nucleotide which is complementary to one of the nucleotides in the template polynucleotide, X is 1, 2, 3 or 4 and Y is 1, 2, 3 or 4 and wherein the population comprises every possible combination of nucleotides N which are complementary to all of the nucleotides in the template polynucleotide. Any of the embodiments discussed above with reference to the method of the invention equally applies to the population of the invention.

Characterisation Method of the Invention

The invention also provides a method of characterising a polynucleotide modified using a method of the invention. The method comprises (a) contacting the modified polynucleotide with a transmembrane pore such that the polynucleotide moves through the pore. The method also comprises (b) taking one or more measurements as the polynucleotide moves with respect to the pore wherein the measurements are indicative of one or more characteristics of the polynucleotide and thereby characterising the modified polynucleotide.

This method is preferably carried out with a potential applied across the pore. The applied potential may be a voltage potential. Alternatively, the applied potential may be a chemical potential. An example of this is using a salt gradient across an amphiphilic layer. A salt gradient is disclosed in Holden et at, J Am Chem Soc. 2007 Jul. 11; 129(27):8650-5. In some instances, the current passing through the pore as the polynucleotide moves with respect to the pore is used to determine the sequence of the modified polynucleotide. This is strand sequencing.

The invention also provides a method of characterising a template polynucleotide. The method comprises modifying the template polynucleotide using a method of the invention to produce a plurality of different modified polynucleotides. Any of the embodiments discussed above may be used. The plurality of modified polynucleotides as a whole preferably includes at least one nucleotide that is complementary to each of the nucleotides in the template polynucleotide.

The method also comprises b) contacting each modified polynucleotide with a transmembrane pore such that the polynucleotide moves through the pore. The method also comprises c) taking one or more measurements as each polynucleotide moves with respect to the pore wherein the measurements are indicative of one or more characteristics of the polynucleotide and thereby characterising the template polynucleotide.

Steps (b) and (c) are preferably carried out with a potential applied across the pore as described above. In some instances, the current passing through the pore as each polynucleotide moves with respect to the pore is used to determine the sequence of each modified polynucleotide. This is strand sequencing. The sequence of the template polynucleotide may then be reconstructed as discussed above. In particular, the method preferably further comprises d) aligning the sequences of the plurality of polynucleotides to produce a sequence which is complementary to the template polynucleotide and thereby sequencing the template polynucleotide.

The whole or only part of the modified or template polynucleotide may be characterized, for instance sequenced, using this method. The length of the template polynucleotide is discussed above. The modified polynucleotide(s) will be substantially the same length.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well in the membrane along which or into which hydrated ions may flow.

Any transmembrane pore may be used in the invention. The pore may be biological or artificial. Suitable pores include, but are not limited to, protein pores, polynucleotide pores and solid state pores.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic layer may be a monolayer or a bilayer. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer.

The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734). In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro. The polynucleotide may be coupled to the membrane. This may be done using any known method. If the membrane is an amphiphilic layer, such as a lipid bilayer (as discussed in detail above), the polynucleotide is preferably coupled to the membrane via a polypeptide present in the membrane or a hydrophobic anchor present in the membrane. The hydrophobic anchor is preferably a lipid, fatty acid, sterol, carbon nanotube or amino acid.

The polynucleotide may be coupled directly to the membrane. The polynucleotide is preferably coupled to the membrane via a linker. Preferred linkers include, but are not limited to, polymers, such as polynucleotides, polyethylene glycols (PEGS) and polypeptides. If a polynucleotide is coupled directly to the membrane, then some data will be lost as the characterising run cannot continue to the end of the polynucleotide due to the distance between the membrane and the pore. If a linker is used, then the polynucleotide can be processed to completion. If a linker is used, the linker may be attached to the polynucleotide at any position. The linker is preferably attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the bilayer and the pore. If the coupling is transient, then when the coupled end randomly becomes free of the bilayer, then the polynucleotide can be processed to completion. Chemical groups that form stable or transient links with the membrane are discussed in more detail below. The polynucleotide may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

In preferred embodiments, the polynucleotide is coupled to an amphiphilic layer. Coupling of polynucleotides to synthetic lipid bilayers has been carried out previously with various different tethering strategies. These are summarised in Table 1 below.

TABLE 1

| Attachment group | Type of coupling | Reference |
| --- | --- | --- |
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholestrol | Transient | Pfeiffer, I. and F. Hook (2004). "Bivalent cholesterol-based coupling of oligonucleotides to lipid membrane assemblies." *J Am Chem Soc* 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the bilayer. The advantages of transient coupling are discussed above.

Coupling of polynucleotides can also be achieved by a number of other means provided that a reactive group can be added to the polynucleotide. The addition of reactive groups to either end of the DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82).

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer with a reactive group attached to it.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the amplified target DNA will contain a reactive group for coupling.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide, such as DNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA MspB, MspC or MspD, outer membrane porin F (OmpF), outer membrane porin G (OmpG), outer membrane phospholipase A and *Neisseria autotransporter* lipoprotein (NalP). α-helix bundle pores comprise a barrel or channel that is formed from α-helices. Suitable α-helix bundle pores include, but are not limited to, inner membrane proteins and α outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-B1 and is called MS-(B2)8. The pore used in the invention is preferably MS-(B2)8. A variant of SEQ ID NO: 2 has the mutations G75S/G77S/L88N/Q126R in addition to all the mutations of MS-B1 and is called MS-B2C. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

Chemical properties of amino acids

| | |
|---|---|
| Ala | aliphatic, hydrophobic, neutral |
| Cys | polar, hydrophobic, neutral |
| Asp | polar, hydrophilic, charged (−) |
| Glu | polar, hydrophilic, charged (−) |
| Phe | aromatic, hydrophobic, neutral |

TABLE 2-continued

Chemical properties of amino acids

| | |
|---|---|
| Gly | aliphatic, neutral |
| His | aromatic, polar, hydrophilic, charged (+) |
| Ile | aliphatic, hydrophobic, neutral |
| Lys | polar, hydrophilic, charged(+) |
| Leu | aliphatic, hydrophobic, neutral |
| Met | hydrophobic, neutral |
| Asn | polar, hydrophilic, neutral |
| Pro | hydrophobic, neutral |
| Gln | polar, hydrophilic, neutral |
| Arg | polar, hydrophilic, charged (+) |
| Ser | polar, hydrophilic, neutral |
| Thr | polar, hydrophilic, neutral |
| Val | aliphatic, hydrophobic, neutral |
| Trp | aromatic, hydrophobic, neutral |
| Tyr | aromatic, polar, hydrophobic |

TABLE 3

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO:

2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels are described below.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with NaBH$_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homo-heptamer) or different (hetero-heptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with the construct. The variant preferably comprises one or more reactive cysteine residues that facilitate attachment to the construct. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (ABC, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a Staphylococcus bacterium. Alternatively, the variant may be expressed in vitro or recombinantly by a bacterium such as Escherichia coli. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135, 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive S$^-$ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

Any of the proteins described herein, such as the transmembrane protein pores, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or construct. An example of this would be to react a gel-shift reagent to a cysteine engineered on the outside of the pore. This has been demonstrated as a method for separating hemolysin hetero-oligomers (Chem Biol. 1997 July; 4(7):497-505).

The pore may be labelled with a revealing label. The revealing label may be any suitable label which allows the pore to be detected. Suitable labels include, but are not limited to, fluorescent molecules, radioisotopes, e.g. $^{125}$I, $^{35}$S, enzymes, antibodies, antigens, polynucleotides and ligands such as biotin.

Any of the proteins described herein, such as the transmembrane protein pores, may be made synthetically or by recombinant means. For example, the pore may be synthesized by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

The pore may also be produced using D-amino acids. For instance, the pore or construct may comprise a mixture of L-amino acids and D-amino acids. This is conventional in the art for producing such proteins or peptides.

The pore may also contain other non-specific modifications as long as they do not interfere with pore formation or construct function. A number of non-specific side chain modifications are known in the art and may be made to the side chains of the protein(s). Such modifications include, for example, reductive alkylation of amino acids by reaction with an aldehyde followed by reduction with NaBH$_4$, amidination with methylacetimidate or acylation with acetic anhydride.

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

The method of the invention involves measuring one or more characteristics of the modified polynucleotide(s) or template polynucleotide. The method may involve measuring two, three, four or five or more characteristics of the polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing through the pore during its interation with each nucleotide.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

In a preferred embodiment, the method comprises:

(a) contacting the/each modified polynucleotide with a transmembrane pore such that the polynucleotide moves through the pore; and (b) measuring the current passing through the pore as the/each polynucleotide moves with respect to the pore wherein the current is indicative of one or more characteristics of the polynucleotide and thereby characterising the modified/template polynucleotide.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Step (a) prefereably further comprises contacting the/each modified polynucleotide with a polynucleotide binding protein such that the protein controls the movement of the polynucleotide through the pore. More preferably, the method comprises (a) contacting the/each modified polynucleotide with a transmembrane pore and a polynucleotide binding protein such that the/each polynucleotide moves through the pore and the protein controls the movement of the/each polynucleotide through the pore and (b) measuring the current passing through the pore as the/each polynucleotide moves with respect to the pore wherein the current is indicative of one or more characteristics of the/each polynucleotide and thereby characterising the modified/template polynucleotide.

The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 11), exonuclease III enzyme from *E. coli* (SEQ ID NO: 13), RecJ from *T. thermophilus* (SEQ ID NO: 15) and bacteriophage lambda exonuclease (SEQ ID NO: 17) and variants thereof. Three subunits comprising the sequence shown in SEQ ID NO: 15 or a variant thereof interact to form a trimer exonuclease. The enzyme is preferably Phi29 DNA polymerase (SEQ ID NO: 9) or a variant thereof. The topoisomerase is preferably a member of any of the Moiety Classification (EC) groups 5.99.1.2 and 5.99.1.3.

The enzyme is most preferably derived from a helicase, such as Hel308 Mbu (SEQ ID NO: 18), Hel308 Csy (SEQ ID NO: 19), Hel308 Mhu (SEQ ID NO: 20), TraI Eco (SEQ ID NO: 21), XPD Mbu (SEQ ID NO: 22) or a variant thereof.

A variant of SEQ ID NOs: 9, 11, 13, 15, 17, 18, 19, 20, 21, 22 or 23 is an enzyme that has an amino acid sequence which varies from that of SEQ ID NO: 9, 11, 13, 15, 17, 18, 19, 20, 21, 22 or 23 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature.

Over the entire length of the amino acid sequence of SEQ ID NO: 9, 11, 13, 15, 17, 18, 19, 20, 21, 22 or 23, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 9, 11, 13, 15, 17, 18, 19, 20, 21, 22 or 23 over the entire sequence. There may be at least 80%, for example at least 85%, 90% or 95%, amino acid identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 and 4 above. The enzyme may be covalently attached to the pore. Any method may be used to covalently attach the enzyme to the pore.

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

The method of characterising a modified or a template polynucleotide preferably involves contacting the polynucleotide with a pore and a polynucleotide binding protein derived from a helicase. Any helicase may be used in the method. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the bilayer. Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the bilayer.

The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide through the pore.

The method is typically carried out in the presence of free nucleotides or free nucleotide analogues and an enzyme cofactor that facilitates the action of the polynucleotide binding protein. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Kits

The present invention also provides a kit for characterising a template polynucleotide. The kit comprises (a) a population of nucleotide oligomers of the invention and (b) a ligase enzyme. Any of the embodiments discussed above with reference to the method of the invention equally apply to the kits.

The kit may further comprise the components of a membrane, such as the components of an amphiphilic layer or a lipid bilayer.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

The following Example illustrates the invention.

EXAMPLE

Example 1

This example describes the hybridisation of nucleotide oligomers to a sense template polynucleotide strand (SEQ ID NO: 40) and subsequent ligation of the nucleotide oligomers together (FIG. 1).

Materials and Methods 1.1—Ligation Experiments

For the ligation reactions the sense template strand (SEQ ID NO: 40, 100 pmol) was incubated with the appropriate nucleotide oligomers (all nucleotide oligomers were at 100 pmol) in a 1:1 ratio. Into PCR tubes (0.2 mL) was added the following ligation reaction mixtures, detailed in Table 4 below, and the mixtures were incubated at 16° C. for 18 hours. The experimental samples were then tested for successful ligation by exonuclease digestion and PAGE analysis.

Experiment 1—Sense template (SEQ ID NO: 40)+nucleotide oligomers (SEQ ID NO: 42-47)+No DNA ligase Experiment 2—Sense template (SEQ ID NO: 40)+nucleotide oligomers (SEQ ID NO: 42-47)

Experiment 3—Sense template (SEQ ID NO: 40)+nucleotide oligomers (SEQ ID NO: 42-46)

Experiment 4—Sense template (SEQ ID NO: 40)+nucleotide oligomers (SEQ ID NO: 45 and 46)

Experiment 5—Sense template (SEQ ID NO: 40)+nucleotide oligomers (SEQ ID NO: 44-46)

Experiment 6—Sense template (SEQ ID NO: 40)+nucleotide oligomers (SEQ ID NO: 43-46)

Experiment 7—Sense template (SEQ ID NO: 40)+nucleotide oligomers (SEQ ID NO: 42-46)

TABLE 4

|  | Experiment No. | | | | | | | |
| --- | --- | --- | --- | --- | --- | --- | --- | --- |
|  | 1 | 2 | 3 | 4 | 5 | 6 | 7 | Final |
| Water (μL) | 8.55 | 6.55 | 7.55 | 10.55 | 9.55 | 8.55 | 8.55 | To 20 μL |
| SEQ ID NO: 40 (100 uM) | 1 | 1 | 1 | 1 | 1 | 1 | 1 | 5 μM/100 pmol |
| SEQ ID NO: 42 (100 uM) | 1 | 1 | 1 |  |  |  | 1 | 1 |
| SEQ ID NO: 43 (100 uM) | 1 | 1 | 1 |  |  | 1 | 1 | 1 |
| SEQ ID NO: 44 (100 uM) | 1 | 1 | 1 |  | 1 | 1 | 1 | 1 |
| SEQ ID NO: 45 (100 uM) | 1 | 1 | 1 | 1 | 1 | 1 | 1 | 1 |
| 3SEQ ID NO: 46 (100 uM) | 1 | 1 | 1 | 1 | 1 | 1 | 1 | 1 |
| SEQ ID NO: 47 (100 uM) | 1 | 1 |  |  |  |  |  |  |
| 10x DNA Ligase Buffer | 0 | 2 | 2 | 2 | 2 | 2 | 2 | 1x |
| rATP (100 mM) | 0.2 | 0.2 | 0.2 | 0.2 | 0.2 | 0.2 | 0.2 | 1 mM |
| T4 DNA Ligase (2000 U/μL) | 0.25 | 0.25 | 0.25 | 0.25 | 0.25 | 0.25 | 0.25 | 500 U |
| DMSO | 4 | 4 | 4 | 4 | 4 | 4 | 4 | 20% |
| Total | 20 | 20 | 20 | 20 | 20 | 20 | 20 |  |

1.2—Tm Experiments

In order to determine the Tm of a DNA strand then the DNA sample (5 μM, 4 μL) was diluted in water (26 μL) giving a final DNA concentration of 0.67 μM. This sample was split into two duplicates and pipette onto a 96-well plate. 4× SYBR green dye (5 μL) was then added to the DNA ligation sample (final DNA concentration of 0.5 μM). The Tm was determined using RT-PCR machine (Agilent Technologies, Stratgene Mx3005P) by heating the sample from 25° C. to 95° C., at a rate of 1° C. every 30 seconds.

1.3—Exonuclease III Digestion of Ligation Experiments

Experiment 2 (described above) and another experiment which contained the chemically synthesised antisense strand (SEQ ID NO: 41) and the sense template (SEQ ID NO: 40) hybridized together, were both subjected to exonuclease III digestion. The following exonuclease reaction mixtures, detailed in Table 5 below, were added to eppendorfs (1.5 mL). The reaction mixtures were then incubated for 1 hour at 37° C. These samples were then heat inactivated by heating at 70° C. for 20 mins.

TABLE 5

| Reagent | Volume (μL) |
| --- | --- |
| DNA Sample (5 μM) | 8 |
| NEB Buffer 1 (10x) | 2 |
| Water | 9 |
| ExoIII (100 U/μL) | 1 |
| Total | 20 |

Results

FIG. 1A shows how the various nucleotide oligomers (SEQ ID NOs: 42-47) can hybridise to the sense template polynucleotide strand (SEQ ID NO: 40) and then be ligated together to form the ligated antisense strand (SEQ ID NO: 42-47). In order to determine the success of the hybridisation and ligation steps a number of analysis techniques can be carried out on the DNA strands. For example, Tm values provide a high throughput means of assessing cooperative ligation of small known sequence adapters and Exo III digestion of the sense template strand, (SEQ ID NO: 40), and subsequent PAGE analysis can provide information regarding the length of the ligated antisense strand.

Figure 2:
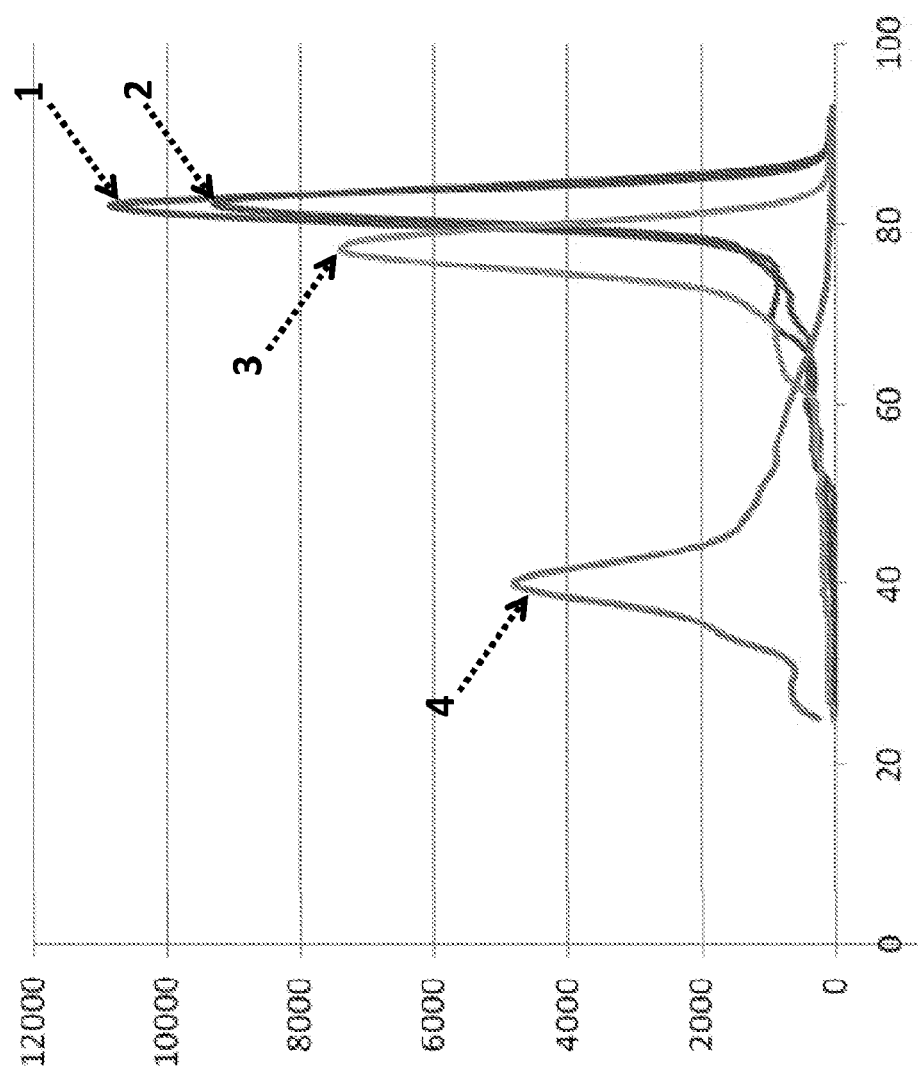
FIG. 2 shows the measured Tm values for a number of different double-stranded DNA oligomers (y-axis label=d (F)/d(T), x-axis label=Temperature in ° C.). 1 corresponds to the sense template polynucleotide (SEQ ID NO: 40) hybridised to the chemically synthesised antisense strand (SEQ ID NO: 41). 2 corresponds to the sense template polynucleotide (SEQ ID NO: 40) hybridised to the antisense strand which was made by ligation of SEQ ID NOs: 42-47. 3 corresponds to the sense template polynucleotide (SEQ ID NO: 40) hybridised to the chemically synthesised antisense strand which contains 3 abasic residues (SEQ ID NO: 48). 4 corresponds to the sense template polynucleotide (SEQ ID NO: 40) hybridised to the nucleotide oligomers (SEQ ID NOs: 42-47) in the absence of ligase enzyme.
Figure 3:
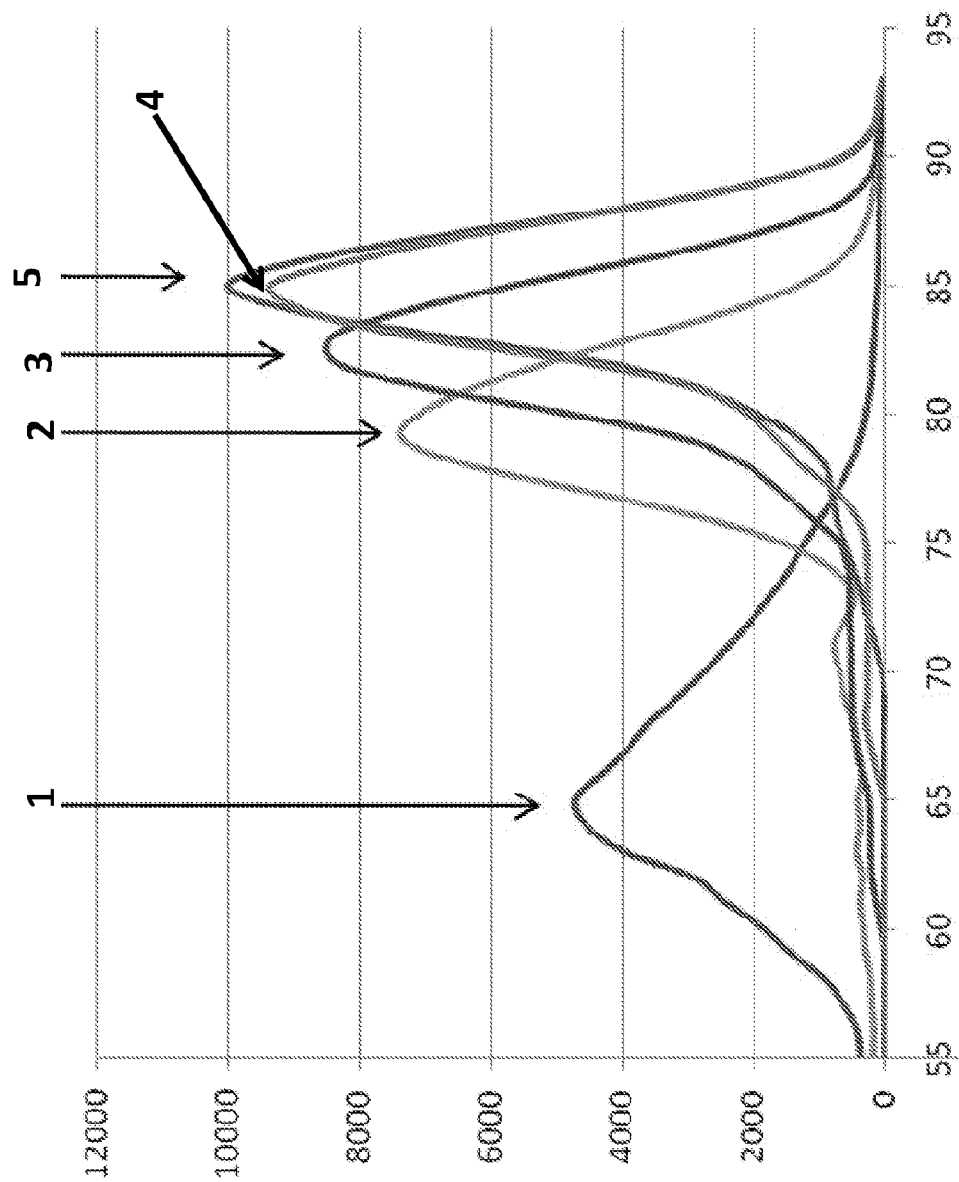
FIG. 3 shows the measured Tm values for a number of nucleotide oligomers to the DNA sense template polynucleotide (SEQ ID NO: 40) (y-axis label=d(F)/d(T), x-axis label=Temperature in ° C.). 1 corresponds to the sense template polynucleotide (SEQ ID NO: 40) added to SEQ ID NO: 45 and SEQ ID NO: 46 in the presence of a ligase (2mer). 2 corresponds to the sense template polynucleotide (SEQ ID NO: 40) hybridised to the ligated SEQ ID NOs: 44-46. 3 corresponds to the sense template polynucleotide (SEQ ID NO: 40) hybridised to the ligated SEQ ID NOs: 43-46. 4 corresponds to the sense template polynucleotide (SEQ ID NO: 40) hybridised to the ligated SEQ ID NOs: 42-46. 5 corresponds to the sense template polynucleotide (SEQ ID NO: 40) hybridised to the ligated SEQ ID NOs: 42-47. It is possible to sequentially ligate 2, 3, 4, 5 and 6 nucleotide oligomers together and distinguish between the 2, 3, 4 and 5 nucleotide oligomers by virtue of their different Tm values. It was not possible to distinguish between 5 and 6 nucleotide oligomers as similar Tm's were measured.

The Tm values were investigated for a number of different double-stranded DNA polynucleotides (FIG. 2). The Tm for 2 (where the antisense strand was made from ligated SEQ ID NOs: 42-47) was similar to that of 1 (where the antisense strand was chemically synthesised) which indicates that the complete antisense strand was formed during the ligation step. A significantly lower Tm was measured when SEQ ID NOs: 42-47 were incubated with the sense template strand in the absence of ligase enzyme (see 4 in FIG. 2). This is likely due to the fact that a stable ds-DNA complex was not formed as SEQ ID NOs; 42-47 were not ligated together. FIG. 3 shows that it was also possible to determine the number of oligomers which had been successfully ligated together by measuring their Tm values. Differences in Tm values were such that it was possible to distinguish between two (labelled 1 in FIG. 3), three (labelled 2 in FIG. 3), four (labelled 3 in FIG. 3) and five nucleotide oligomers (labelled 4 in FIG. 3) by virtue of their different Tm values. However, the ligated five (labelled 4 in FIG. 4) and six nucleotide oligomers (labelled 5 in FIG. 4) were not distinguishable from each other by Tm analysis.

Figure 4:
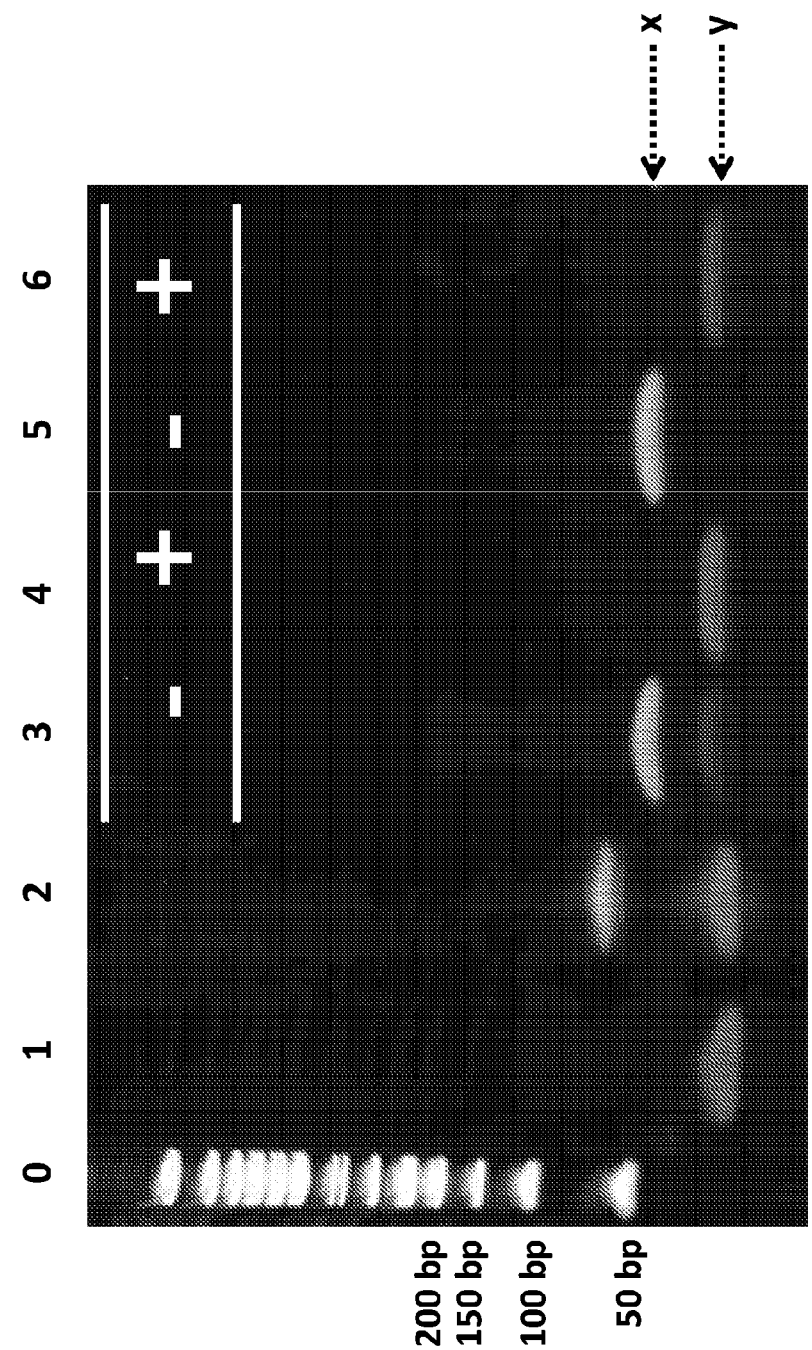
FIG. 4 shows a PAGE of a number of different samples, some of which have been exposed to exonuclease III digestion. The bands labelled x correspond to dsDNA and the bands labelled y correspond to ssDNA and the – and + symbols correspond to whether that lane (3-6) was exposed to Exo III (+ means the DNA was exposed and – means the DNA was not exposed). Lane 0 corresponds to a DNA ladder. Lane 1 corresponds to the sense template polynucleotide (SEQ ID NO: 40). Lane 2 corresponds to the chemically synthesised antisense strand (lower band, SEQ ID NO: 41). Lane 3 corresponds to the duplex formed between SEQ ID NOs: 40 and 41 which has not been exposed to exonuclease III digestion. Lane 4 corresponds to the duplex formed between SEQ ID NOs: 40 and 41 which has been exposed to exonuclease III digestion. Lane 5 corresponds to the duplex formed between SEQ ID NOs: 40 and the ligated strands SEQ ID NOs: 42-47 which has not been exposed to exonuclease III digestion. Lane 6 corresponds to the duplex formed between SEQ ID NOs: 40 and the ligated strands SEQ ID NOs: 42-47 which has been exposed to exonuclease III digestion. This shows that the ligated antisense strand (SEQ ID NOs: 42-47) forms a stable complex with the sense template strand (SEQ ID NO: 40) that runs at the same point in a PAGE as the duplex formed from the chemically synthesised antisense strand (SEQ ID NO: 41). The digestion of the sense template strand (SEQ ID NO: 40) hybridised to SEQ ID NOs: 42-47 also produces a band which corresponds the chemically synthesised antisense strand (SEQ ID NO: 41).

Exo III digestion, of various different double-stranded DNA polynucleotides which did not contain any abasic residues, was investigated. In FIG. 4, Lanes 1 and 2 correspond to the sense template polynucleotide (SEQ ID NO: 40) and the chemically synthesised antisense strand (lower band, SEQ ID NO: 41) respectively. Lane 3 shows that in the absence of ExoIII the sense template and chemically synthesised antisense strand hybridise together to form dsDNA. However in the presence of ExoIII, the sense template strand (SEQ ID NO: 40) is digested and the chemically synthesised antisense strand (which contains an RNA blocker at the 3' end) was not digested. Therefore, a lower band which corresponds to the single-stranded chemically synthesised antisense strand was detected. Lanes 5 and 6 show the ligated antisense strand (SEQ ID NO: 42-47) and sense template in the presence (lane 6) and absence (lane 5) of ExoIII. A dsDNA band was observed in the absence of ExoIII (lane 5) and a ssDNA band was observed after digestion (lane 6, the ligated antisense strand was protected from digestion by an RNA blocker at the 3' end), therefore, the ligated antisense strand behaved in a similar manner to the chemically synthesised antisense starnd. This indicates that the hybridisation and ligation of the nucleotide oligomers (which contained no abasic residues) was successful.

Example 2

Figure 5:
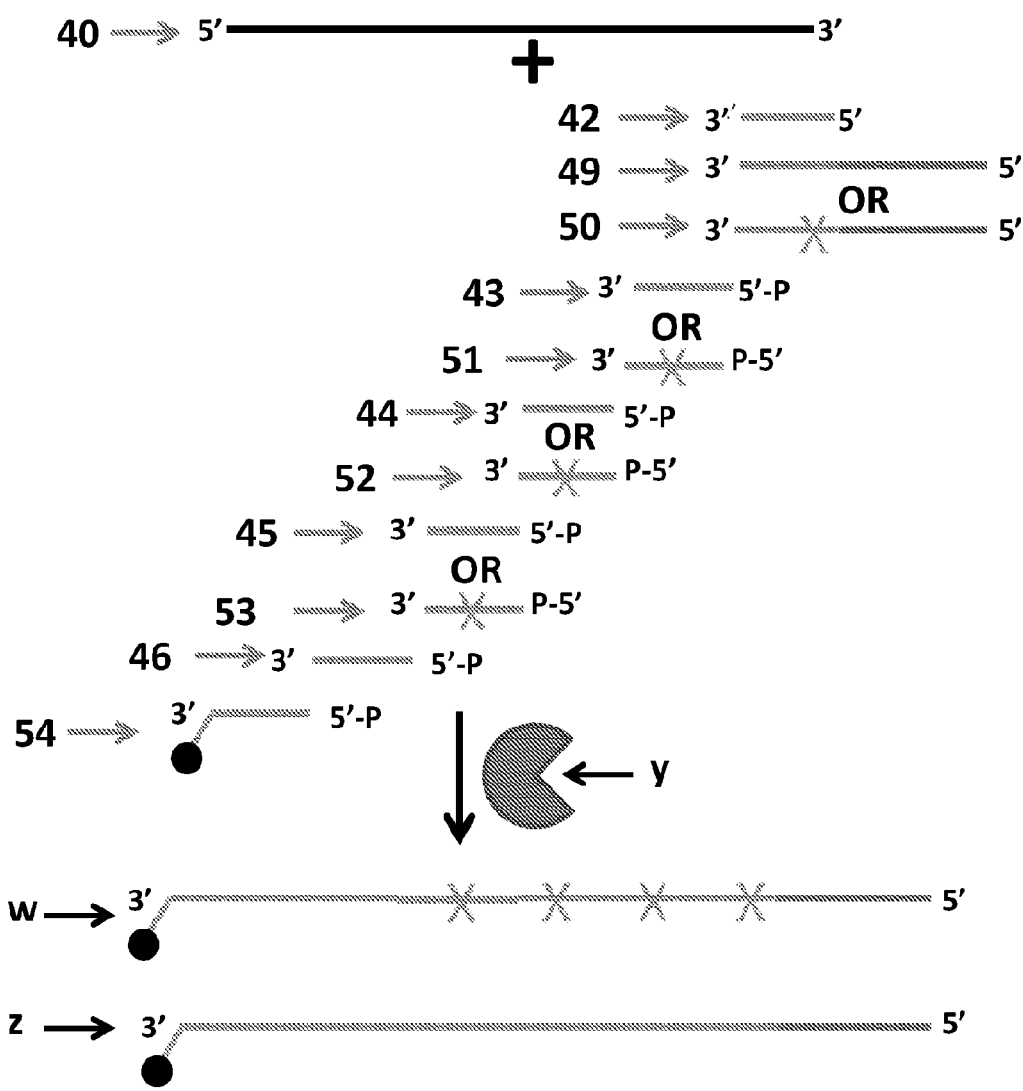
FIG. 5 shows how the various nucleotide oligomers some of which contain abasic residues (SEQ ID NOs: 42-46 and 49-54, SEQ ID NOs are indicated on one side of the corresponding strand by an arrow) can hybridise to the sense template polynucleotide strand (SEQ ID NO: 40) and then be ligated together (using a DNA ligase labelled y) to form various antisense DNA sequences (sequences labelled w and z and variations of these sequences are produced). The cholesterol TEG is labelled as a black circle.

This example describes the hybridisation of nucleotide oligomers, which contain abasic residues, to a sense template polynucleotide strand (SEQ ID NO: 40) and subsequent ligation of the nucleotide oligomers together (FIG. 5).

Materials and Methods
2.1—Ligation Experiments

For the ligation reactions the sense template strand (SEQ ID NO: 40, 100 pmol) was incubated with the appropriate nucleotide oligomers (all nucleotide oligomers were at 100 pmol) in a 1:1 ratio. Into PCR tubes (0.2 mL) was added the following ligation reaction mixtures, detailed in Table 6 below, and the mixtures were incubated at 16° C. for 18 hours. The experimental samples were then tested for successful ligation by exonuclease digestion and PAGE analysis.

Experiment 1—Sense template (SEQ ID NO: 40)+nucleotide oligomers (SEQ ID NO: 46 and 54)
Experiment 2—Sense template (SEQ ID NO: 40)+nucleotide oligomers (SEQ ID NO: 45, 46 and 54)
Experiment 3—Sense template (SEQ ID NO: 40)+nucleotide oligomers (SEQ ID NO: 44, 45, 46 and 54)
Experiment 4—Sense template (SEQ ID NO: 40)+nucleotide oligomers (SEQ ID NO: 43, 44, 45, 46 and 54)
Experiment 5—Sense template (SEQ ID NO: 40)+nucleotide oligomers (SEQ ID NO: 49, 43, 44, 45, 46 and 54)
Experiment 6—Sense template (SEQ ID NO: 40)+nucleotide oligomers (SEQ ID NO: 53, 46 and 54)
Experiment 7—Sense template (SEQ ID NO: 40)+nucleotide oligomers (SEQ ID NO: 52, 53, 46 and 54)
Experiment 8—Sense template (SEQ ID NO: 40)+nucleotide oligomers (SEQ ID NO: 51, 52, 53, 46 and 54)
Experiment 9—Sense template (SEQ ID NO: 40)+nucleotide oligomers (SEQ ID NO: 50, 51, 52, 53, 46 and 54)
Experiment 10—Sense template (SEQ ID NO: 40)+nucleotide oligomers (SEQ ID NO: 49, 51, 52, 53, 46 and 54)
Experiment 11—Sense template (SEQ ID NO: 40)+nucleotide oligomers (SEQ ID NO: 52, 45, 46 and 54)
Experiment 12—Sense template (SEQ ID NO: 40)+nucleotide oligomers (SEQ ID NO: 51, 52, 45, 46 and 54)
Experiment 13—Sense template (SEQ ID NO: 40)+nucleotide oligomers (SEQ ID NO: 50, 51, 52, 45, 46 and 54)

TABLE 6

| | Experiment No. | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | Final |
| Water (μL) | 10.55 | 9.55 | 8.55 | 7.55 | 6.55 | 9.55 | 8.55 | 7.55 | 6.55 | 6.55 | 8.55 | 7.55 | 6.55 | To 20 μL |
| SEQ ID NO: 40 (100 uM) | 1 | 1 | 1 | 1 | 1 | 1 | 1 | 1 | 1 | 1 | 1 | 1 | 1 | 5 μM/100 pmol |
| SEQ ID NO: 49 (100 uM) | | | | | 1 | | | | | 1 | | | | |
| SEQ ID NO: 50 (100 uM) | | | | | | | | | 1 | | | | 1 | |
| SEQ ID NO: 43 (100 uM) | | | | 1 | 1 | | | | | | | | | |
| SEQ ID NO: 51 (100 uM) | | | | | | | | 1 | 1 | 1 | | 1 | 1 | |
| SEQ ID NO: 44 (100 uM) | | | 1 | 1 | 1 | | | | | | | | | |
| SEQ ID NO: 52 (100 uM) | | | | | | | 1 | 1 | 1 | 1 | 1 | 1 | 1 | |
| SEQ ID NO: 45 (100 uM) | | 1 | 1 | 1 | 1 | | | | | | 1 | 1 | 1 | |
| SEQ ID NO: 53 (100 uM) | | | | | | 1 | 1 | 1 | 1 | 1 | | | | |
| SEQ ID NO: 46 (100 uM) | 1 | 1 | 1 | 1 | 1 | 1 | 1 | 1 | 1 | 1 | 1 | 1 | 1 | |
| SEQ ID NO: 54 (100 uM) | 1 | 1 | 1 | 1 | 1 | 1 | 1 | 1 | 1 | 1 | 1 | 1 | 1 | |
| 10x DNA Ligase Buffer | 2 | 2 | 2 | 2 | 2 | 2 | 2 | 2 | 2 | 2 | 2 | 2 | 2 | 1x |
| rATP (100 mM) | 0.2 | 0.2 | 0.2 | 0.2 | 0.2 | 0.2 | 0.2 | 0.2 | 0.2 | 0.2 | 0.2 | 0.2 | 0.2 | 1 mM |
| T4 DNA Ligase (2000 U/μL) | 0.25 | 0.25 | 0.25 | 0.25 | 0.25 | 0.25 | 0.25 | 0.25 | 0.25 | 0.25 | 0.25 | 0.25 | 0.25 | 500 U |
| DMSO | 4 | 4 | 4 | 4 | 4 | 4 | 4 | 4 | 4 | 4 | 4 | 4 | 4 | 20% |
| Total | 20 | 20 | 20 | 20 | 20 | 20 | 20 | 20 | 20 | 20 | 20 | 20 | 20 | |

2.2—Tm Experiments

Same process was followed as described in Example 1 above.

2.3—Exonuclease I Digestion of Ligation Experiments

Each of the experiments, 1-13 described above, were subjected to exonuclease digestion conditions. The following exonuclease reaction mixtures, detailed in Table 7 below, were added to eppendorfs (1.5 mL). The reaction mixtures were then incubated for 1 hour at 37° C.

TABLE 7

| Reagent | Volume (µL) |
| --- | --- |
| DNA Sample (5 µM) | 8 |
| Exo I Buffer (10x) | 2 |
| Water | 9 |
| Exo I | 1 |
| Total | 20 |

The digested samples were then analysed by PAGE. Nucleic acid loading dye (6×, 4 µL) was added to the 20 µL digest from each of the Experiments 1-13. The samples were loaded onto a 10% TBE PAGE and the gel run for 1 hour at 140 V. The DNA bands were then stained with SYBR gold gel stain.

Results

It was investigated if it was possible to hybridise and ligate nucleotide oligomers together which contain abasic residues. FIG. 2 shows that a chemically synthesised antisense strand which contained three abasic residues (SEQ ID NO: 48, data 3) had a lower Tm value than a strand containing no abasic residues (data 1 and 2). The lower Tm value is likely to be a result of the abasic residues not being able to form DNA base-pairs, therefore, resulting in a less stable complex. Therefore, by measuring the Tm it was possible to detect the presence of abasic residues in a strand of DNA.

Figure 6:
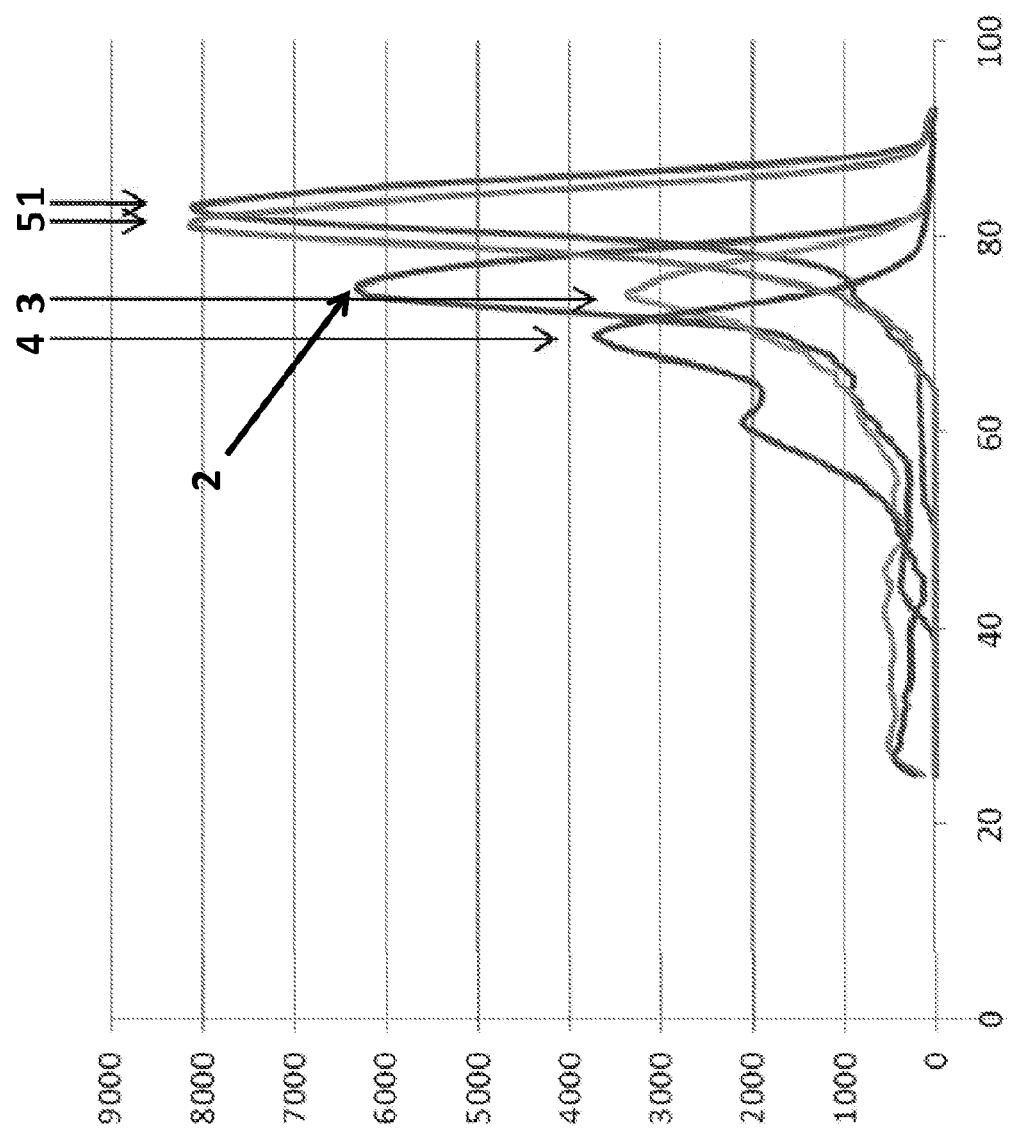
FIG. 6 shows the measured Tm values for a number of different double-stranded DNA polynucleotides (y-axis label=d(F)/d(T), x-axis label=Temperature in ° C.). Line 1 shows that the ligated antisense stand, which contains no abasic residues (SEQ ID NO: 42-46), can hybridise to the sense template strand (SEQ ID NO: 40). Line 2 shows ligation of two nucleotide oligomers complementary to each end of the sense template (SEQ ID NOs: 42, 43, 45 and 46) but with the middle complementary nucleotide oligomer absent (SEQ ID NO: 44) can hybridise to the sense template strand (SEQ ID NO: 40). The Tm is lower than for 1 because the middle complementary nucleotide oligomer is absent, therefore, the hybridised DNA complex is less stable. Line 3 ligation of three nucleotide oligomers complementary to one end of the sense template (SEQ ID NOs: 52, 45 and 46) can hybridise to the sense template strand (SEQ ID NO: 40). The first nucleotide oligomer (SEQ ID NO: 52) contains a single abasic residue. Line 4 shows that the ligation of three strands complementary to one end of the sense template (SEQ ID NOs: 42, 43 and 52) can hybridise to the sense template strand (SEQ ID NO: 40). The last nucleotide oligomer (SEQ ID NO: 52) contains a single abasic residue. Line 5 shows that the ligated antisense strand, which contains a single abasic residue (SEQ ID NOs: 49, 43, 52, 45 and 54), can hybridise to the sense template strand (SEQ ID NO: 40). The polynucleotides containing a single abasic residue have a slightly lower Tm value when compared to those polynucleotides which contain no abasic residues.

In order to establish whether it is possible to ligate nucleotide oligomers which contain abasic residues, then further Tm and ExoI digestion experiments were carried out. FIG. 6, line 1 shows that the ligated antisense strand, which contains no abasic residues (SEQ ID NO: 42-46), can hybridise to the sense template strand (SEQ ID NO: 40). FIG. 6 line 5 shows that the ligated antisense strand, which contains a single abasic residue (SEQ ID NOs: 49, 43, 52, 45 and 54), can hybridise to the sense template strand. The strand containing a single abasic had a slightly lower Tm value. Line 2 corresponds to ligation of two nucleotide oligomers complementary to each end of the sense template (SEQ ID NOs: 42, 43, 45 and 46) but with the middle complementary nucleotide oligomer absent (SEQ ID NO: 44). Lines 4 and 3 have a similar nucleotide oligomer arrangements to each other as they both have three nucleotide oligomers ligated together with one of the end nucleotide oligomers containing a single abasic residue. These two lines have lower Tm values in comparison to line 2 which has also undergone two successful ligations. This shows that strands which contain single abasic residues can hybridise and ligate together.

Figure 7:
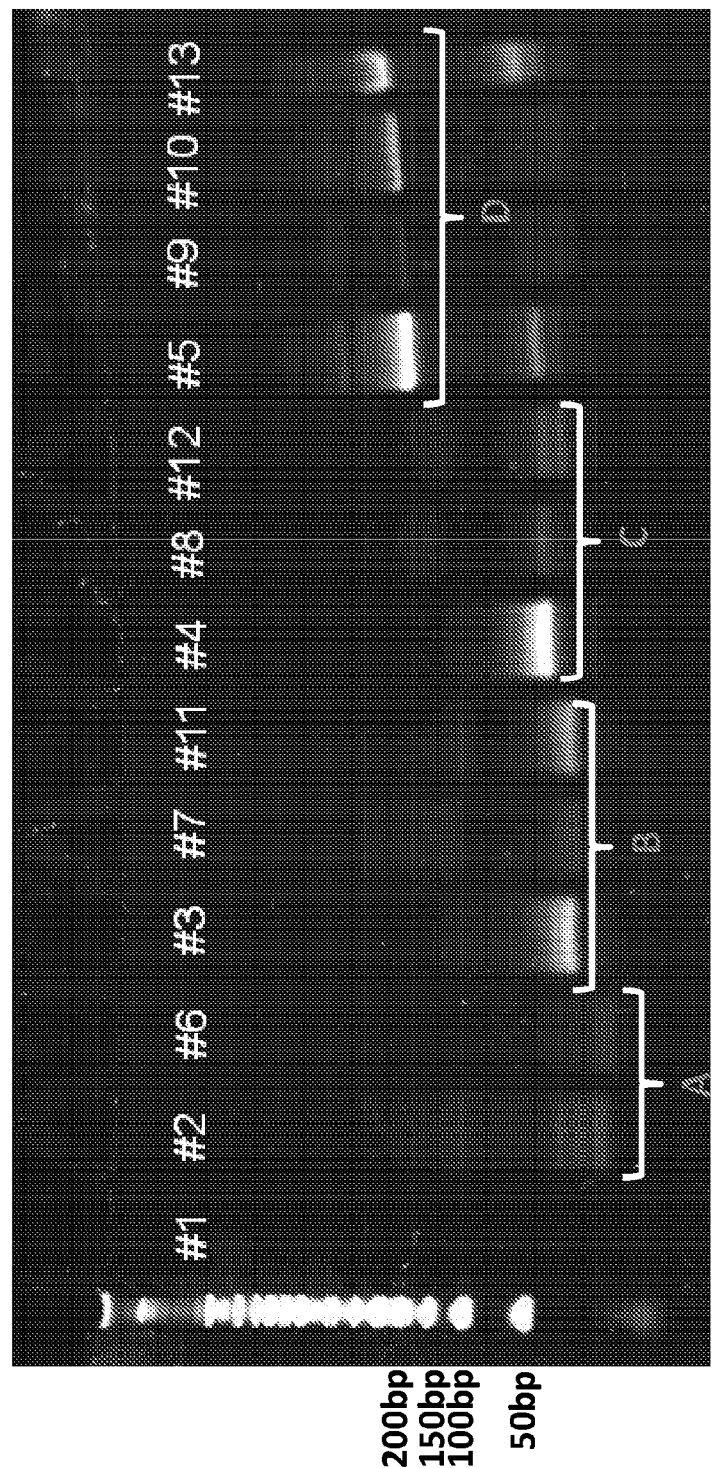
FIG. 7 shows a PAGE of a number of different samples which have undergone ligation reactions and subsequent ExoI digestion of the remaining single-stranded region of the sense template strand (SEQ ID NO: 40). Lane #0 corresponds to a DNA ladder. Lane #1 corresponds to hybridisation of SEQ ID NO: 46 and 54 to the sense template strand (SEQ ID NO: 40), ligation of SEQ ID NO: 46 to 54 and ExoI digestion. Lane #2 corresponds to hybridisation of SEQ ID NO: 45, 46 and 54 to the sense template strand (SEQ ID NO: 40), ligation of SEQ ID NO: 45, 46 and 54 and ExoI digestion. Lane #3 corresponds to hybridisation of SEQ ID NO: 44, 45, 46 and 54 to the sense template strand (SEQ ID NO: 40), ligation of SEQ ID NO: 44, 45, 46 and 54 and ExoI digestion. Lane #4 corresponds to hybridisation of SEQ ID NO: 43, 44, 45, 46 and 54 to the sense template strand (SEQ ID NO: 40), ligation of SEQ ID NO: 43, 44, 45, 46 and 54 and ExoI digestion. Lane #5 corresponds to hybridisation of SEQ ID NO: 49, 43, 44, 45, 46 and 54 to the sense template strand (SEQ ID NO: 40), ligation of SEQ ID NO: 49, 43, 44, 45, 46 and 54 and ExoI digestion. Lane #6 corresponds to hybridisation of SEQ ID NO: 53, 46 and 54 to the sense template strand (SEQ ID NO: 40), ligation of SEQ ID NO: 53, 46 and 54 and ExoI digestion. Lane #7 corresponds to hybridisation of SEQ ID NO: 52, 53, 46 and 54 to the sense template strand (SEQ ID NO: 40), ligation of SEQ ID NO: 52, 53, 46 and 54 and ExoI digestion. Lane #8 corresponds to hybridisation of SEQ ID NO: 51, 52, 53, 46 and 54 to the sense template strand (SEQ ID NO: 40), ligation of SEQ ID NO: 51, 52, 53, 46 and 54 and ExoI digestion. Lane #9 corresponds to hybridisation of SEQ ID NO: 50, 51, 52, 53, 46 and 54 to the sense template strand (SEQ ID NO: 40), ligation of SEQ ID NO: 50, 51, 52, 53, 46 and 54 and ExoI digestion. Lane #10 corresponds to hybridisation of SEQ ID NO: 49, 51, 52, 53, 46 and 54 to the sense template strand (SEQ ID NO: 40), ligation of SEQ ID NO: 49, 51, 52, 53, 46 and 54 and ExoI digestion. Lane #11 corresponds to hybridisation of SEQ ID NO: 52, 45, 46 and 54 to the sense template strand (SEQ ID NO: 40), ligation of SEQ ID NO: 52, 45, 46 and 54 and ExoI digestion. Lane #12 corresponds to hybridisation of SEQ ID NO: 51, 52, 45, 46 and 54 to the sense template strand (SEQ ID NO: 40), ligation of SEQ ID NO: 51, 52, 45, 46 and 54 and ExoI digestion. Lane #13 corresponds to hybridisation of SEQ ID NO: 50, 51, 52, 45, 46 and 54 to the sense template strand (SEQ ID NO: 40), ligation of SEQ ID NO: 50, 51, 52, 45, 46 and 54 and ExoI digestion. Bands in section A correspond to the ligation of three nucleotide oligomers together, bands in section B of FIG. 7 correspond to the ligation of four nucleotide oligomers together, bands in section C of FIG. 7 correspond to the ligation of five nucleotide oligomer together and bands in section D of FIG. 7 correspond to the ligation of six nucleotide oligomers together. This example shows how it was possible to ligate multiple nucleotide oligomers together which contain abasic residues.
Figure 8:
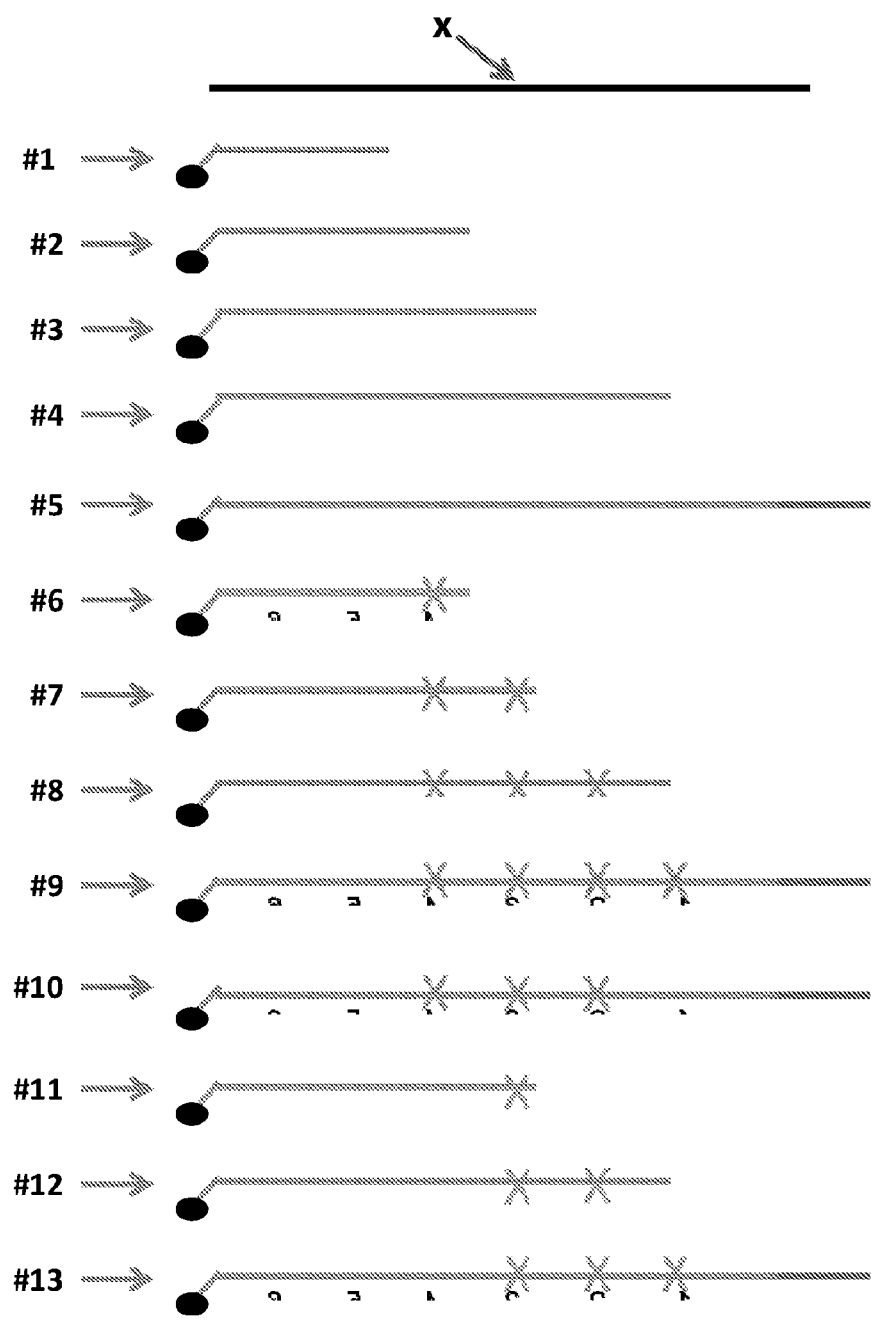
FIG. 8 shows a schematic picture of the DNA strands which were produced by each ligation experiment described in Example 2. The SEQ ID NO's which correspond to # numbers in FIG. 8 are as follows #1=SEQ ID NO: 46 and 54, #2=SEQ ID NO: 45, 46 and 54, #3=SEQ ID NO: 44, 45, 46 and 54, #4=SEQ ID NO: 43, 44, 45, 46 and 54, #5=SEQ ID NO: 49, 43, 44, 45, 46 and 54, #6=SEQ ID NO: 53, 46 and 54, #7=SEQ ID NO: 52, 53, 46 and 54, #8=SEQ ID NO: 51, 52, 53, 46 and 54, #9=SEQ ID NO: 50, 51, 52, 53, 46 and 54, #10=49, 51, 52, 53, 46 and 54, #11=SEQ ID NO: 52, 45, 46 and 54, #12=SEQ ID NO: 51, 52, 45, 46 and 54, #13=SEQ ID NO: 50, 51, 52, 45, 46 and 54. The template strand (SEQ ID NO: 40) is labelled as x.

It was then investigated as to whether multiple nucleotide oligomers which contained a single abasic residue could be hybridised to the sense template strand (SEQ ID NO: 40) and then ligated together. FIG. 7 shows ligation experiments 1-13 after they have been subjected to ExoI digestion (ExoI digests ssDNA but leaves dsDNA intact) and FIG. 8 shows a schematic picture of the DNA constructs which were produced by each ligation experiment. Bands in section A of FIG. 7 corresponds to the ligation of three nucleotide oligomers together, section B of FIG. 7 corresponds to the ligation of four nucleotide oligomers together, section C of FIG. 7 corresponds to the ligation of five nucleotide oligomer together and section D of FIG. 7 corresponds to the ligation of six nucleotide oligomers together. It was possible to observe successful ligation of six nucleotide oligomers four of which contained single abasic residues (see lane labelled #9). This example shows how it was possible to ligate multiple nucleotide oligomers together which contain abasic residues.

Example 3

Figure 9:
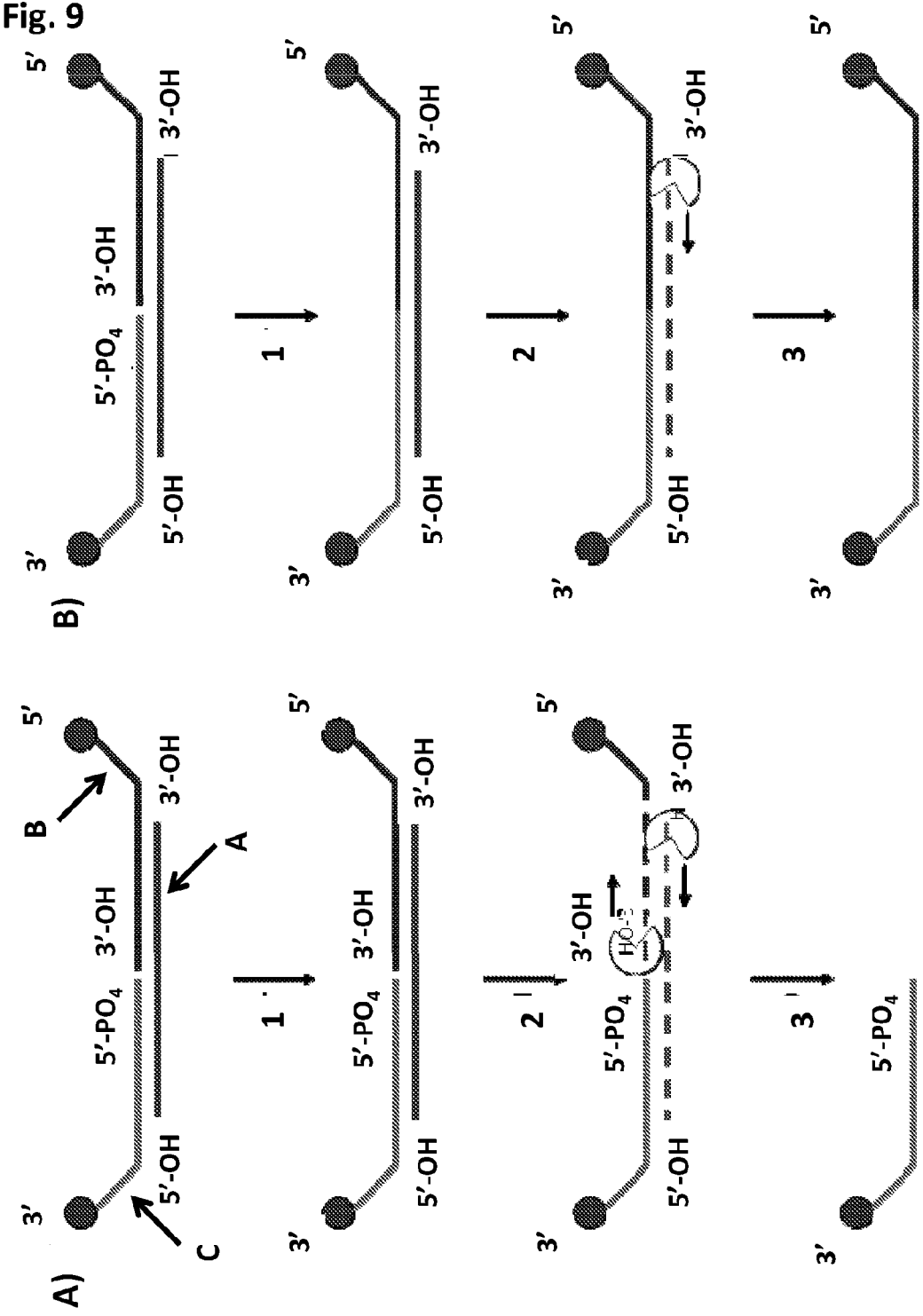
FIG. 9 shows a schematic representation of the ligation and ExoIII digestion steps which are used to determine whether successful ligation of the 5' and 3' sense strands has occurred. A) Shows that the ligation step (labelled 1, the enzyme used was T4 DNA ligase) was unsuccessful so when the sense template (labelled A) and the 5' antisense (labelled B) and 3' antisense (labelled C) strands were subjected to ExoIII digestion (step labelled 2) then the enzyme (enzyme labelled D) digested the 5' antisense and the sense template. The 3' antisense strand was not digested as the RNA blocker at the 3' end prevented digestion by ExoIII. Step 3 will involve gel analysis of the undigested strand. B) Shows successful ligation of the 5' and 3' antisense strands (step labelled 1, the enzyme used was T4 DNA ligase). When the antisense and sense strands were exposed to ExoIII digestion (step labelled 2) then the sense strand was digested by the enzyme, however, the antisense strand was not digested as the RNA blocker at the 3' end prevented digestion. Gel analysis (step labelled 3) of the resultant strands after ExoIII digestion can be used to determine whether the ligation step was successful (successful ligation—high molecular weight band, unsuccessful ligation—low molecular weight band).

This example describes the hybridisation of nucleotide oligomers, which contain deoxyinosines, to a sense template polynucleotide strand and subsequent ligation of the nucleotide oligomers together (FIG. 9).

Materials and Methods 3.1—Ligation Experiments

Oligos were annealed to create the 3 fragment structure shown in FIG. 9 (two antisense strands ligated to a sense strand to generate a nick to be repaired). The following reaction mixtures, detailed in Table 8 below, were prepared for the experiment sets described below. Oligos were annealed by heating to 98° C. for 2 minutes before being cooled to 18° C. at 2° C. per minute.

Experiment 1—positive control sense template (SEQ ID NO: 55)+positive control 5' antisense strand (SEQ ID NO: 56) and positive control 3' antisense strand (SEQ ID NO: 57)

Experiment 2—negative control sense template (SEQ ID NO: 55)+negative control 5' antisense strand (SEQ ID NO: 56) and negative control 3' antisense strand (SEQ ID NO: 57) in the absence of ligase.

Experiment 3—1I1N sense template to test adenine (SEQ ID NO: 58)+1I1N 5' antisense strand (SEQ ID NO: 59) and 1I1N 3' antisense strand (SEQ ID NO: 60)

Experiment 4—1I1N sense template to test thymine (SEQ ID NO: 61)+1I1N 5' antisense strand (SEQ ID NO: 59) and 1I1N 3' sense strand (SEQ ID NO: 60)

Experiment 5—1I1N sense template to test cytidine (SEQ ID NO: 62)+1I1N 5' antisense strand (SEQ ID NO: 59) and 1I1N 3' antisense strand (SEQ ID NO: 60)

Experiment 6—1I1N sense template to test guanosine (SEQ ID NO: 63)+1I1N 5' antisense strand (SEQ ID NO: 59) and 1I1N 3' antisense strand (SEQ ID NO: 60)

Experiment 7—2I2N sense template to test adenine (SEQ ID NO: 64)+2I2N 5' antisense strand (SEQ ID NO: 65) and 2I2N 3' antisense strand (SEQ ID NO: 66)

Experiment 8—2I2N sense template to test thymine (SEQ ID NO: 67)+2I2N 5' antisense strand (SEQ ID NO: 65) and 2I2N 3' antisense strand (SEQ ID NO: 66)

Experiment 9—2I2N sense template to test cytidine (SEQ ID NO: 68)+2I2N 5' antisense strand (SEQ ID NO: 65) and 2I2N 3' antisense strand (SEQ ID NO: 66)

Experiment 10—2I2N sense template to test guanosine (SEQ ID NO: 69)+2I2N 5' antisense strand (SEQ ID NO: 65) and 2I2N 3' antisense strand (SEQ ID NO: 66)

Experiment 11—3I3N sense template to test adenine (SEQ ID NO: 70)+3I3N 5' antisense strand (SEQ ID NO: 71) and 3I3N 3' antisense strand (SEQ ID NO: 72)

Experiment 12—3I3N sense template to test thymine (SEQ ID NO: 73)+3I3N 5' antisense strand (SEQ ID NO: 71) and 3I3N 3' antisense strand (SEQ ID NO: 72)

Experiment 13—3I3N sense template to test cytidine (SEQ ID NO: 74)+3I3N 5' antisense strand (SEQ ID NO: 71) and 3I3N 3' antisense strand (SEQ ID NO: 72)

Experiment 14—3I3N sense template to test guanosine (SEQ ID NO: 75)+3I3N 5' antisense strand (SEQ ID NO: 71) and 3I3N 3' antisense strand (SEQ ID NO: 72)

Experiment 15—4I4N sense template to test adenine (SEQ ID NO: 76)+4I4N 5' antisense strand (SEQ ID NO: 77) and 4I4N 3' antisense strand (SEQ ID NO: 78)

Experiment 16—4I4N sense template to test thymine (SEQ ID NO: 79)+4I4N 5' antisense strand (SEQ ID NO: 77) and 4I4N 3' antisense strand (SEQ ID NO: 78)

Experiment 17—4I4N sense template to test cytidine (SEQ ID NO: 80)+4I4N 5' antisense strand (SEQ ID NO: 77) and 4I4N 3' antisense strand (SEQ ID NO: 78)

Experiment 18—4I4N sense template to test guanosine (SEQ ID NO: 81)+4I4N 5' antisense strand (SEQ ID NO: 77) and 4I4N 3' antisense strand (SEQ ID NO: 78)

TABLE 8

| Reagent | Volume (µL) |
| --- | --- |
| 2M KCl | 0.5 |
| 100 uM sense template | 1 |
| 100 uM 5' antisense test strand | 1 |
| 100 uM 3' antisense test strand | 1 |
| nuclease free water | 16.5 |
| Total | 20 |

Ligation reactions were assembled as described in Table 9 (10× T4 DNA ligase buffer is made up of ~300 mM Tris-HCl pH 7.8, 100 mM DTT, 100 mM MgCl2 and 10 mM rATP) and 10 (2× Low fidelity (Lo-Fi) buffer is made up of 60 mM Tris-HCl pH 7.5, 20 mM DTT, 6 mM MgCl2, 20 mM rATP and 40% DMSO) below and incubated as described below for each experiment set.

Experiment 1 Incubation Conditions—Table 9 buffer conditions, 22° C., 1 hour.

Experiment 2 Incubation Conditions—Table 9 buffer conditions, 22° C., 1 hour in the absence of DNA ligase (16 µL of nuclease free water added).

Experiments 3, 4, 5 and 6 Incubation Conditions—Table 10 buffer conditions, 30° C., 18 hours.

Experiments 7, 8, 9 and 10 Incubation Conditions—Table 10 buffer conditions, 30° C., 18 hours.

Experiments 11, 12, 13 and 14 Incubation Conditions—Table 9 buffer conditions, 22° C., 18 hours.

Experiments 15, 16, 17 and 18 Incubation Conditions—Table 9 buffer conditions, 22° C., 1 hour.

TABLE 9

| Reagent | Volume (µL) |
| --- | --- |
| annealed DNA | 2 |
| 10× T4 DNA ligase buffer | 2 |
| T4 DNA ligase | 0.25 |
| nuclease free water | 15.75 |
| Total | 20 |

TABLE 10

| Reagent | Volume (µL) |
| --- | --- |
| annealed DNA | 2 |
| 2× Lo-Fi buffer | 10 |
| T4 DNA ligase | 0.25 |
| nuclease free water | 7.75 |
| Total | 20 |

To screen for successful sealing of the nick between adjacent antisense strands ExoIII digestion was used. The size of the liberated ssDNA will indicate successful nick repair (see FIGS. 9A and B). Reactions were assembled as described in Table 11 below. Reactions were left to proceed for 30 mins at 37° C.

TABLE 11

| Reagent | Volume (µL) |
| --- | --- |
| ligation reaction product | 8 |
| 10× NEBuffer 1 | 2 |
| 100 U ul$^{-1}$ ExoIII | 1 |
| nuclease free water | 9 |
| Total | 20 |

To analyse reaction products, samples were run on a 5% TBE PAGE gel for 40 mins at 140 V and bands visualised by SYBR Gold staining.

Results

Figure 10:
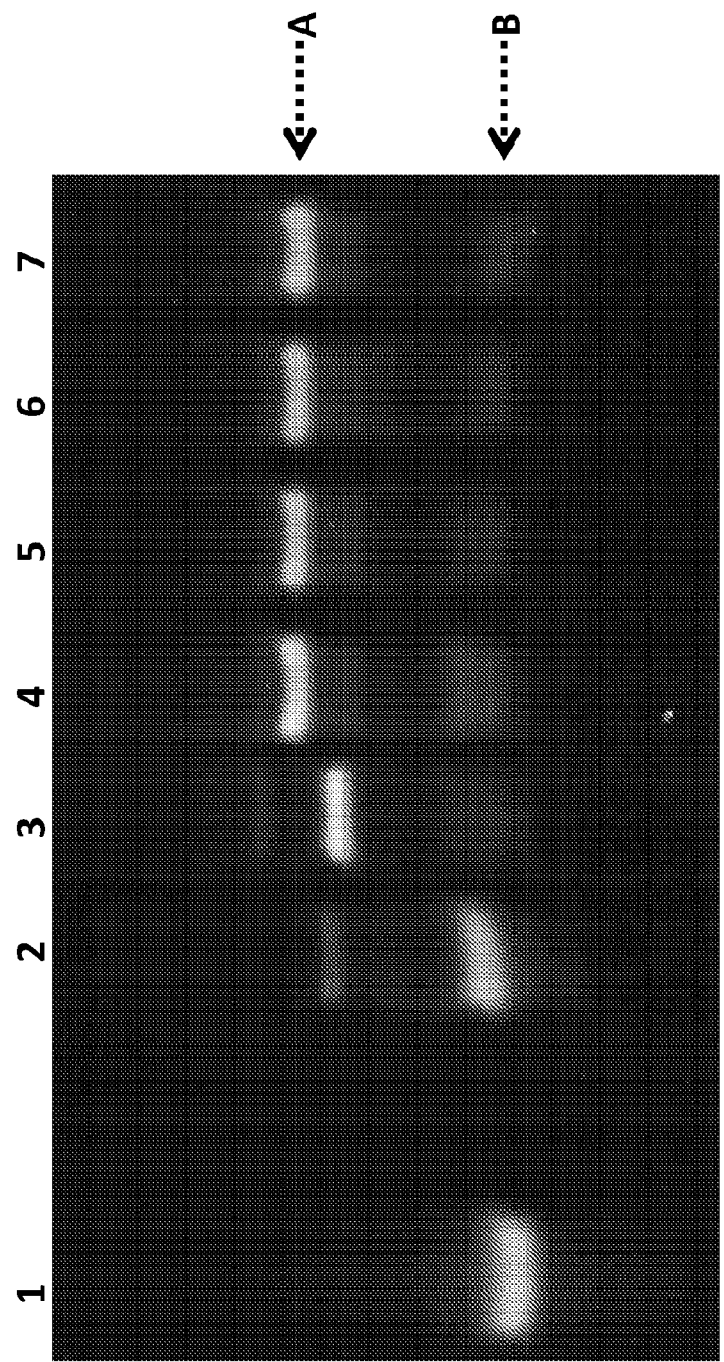
FIG. 10 shows a PAGE gel of the control experiments 1-2 and the 4N4I experiments 14-18 after they have undergone both the ligation and ExoIII digestion (upper band labelled A is the ligated product, the lower band labelled B is the non-ligated product). Lane 1 contains the positive control 3' antisense strand (SEQ ID NO: 57) as a reference for unligated products. Lane 2 contains the DNA products from Experiment 2 after ligation (in the absence of T4 DNA liagse) and digestion (negative control sense template (SEQ ID NO: 55)+negative control 5' antisense strand (SEQ ID NO: 56) and negative control 3' antisense strand (SEQ ID NO: 57)). Lane 3 contains the DNA products from Experiment 1 after ligation and digestion (positive control sense template (SEQ ID NO: 55)+positive control 5' antisense strand (SEQ ID NO: 56) and positive control 3' antisense strand (SEQ ID NO: 57) in the presence of ligase). Lane 4 contains the DNA products from Experiment 18 after ligation and digestion (4I4N sense template to test guanosine (SEQ ID NO: 81)+4I4N 5' antisense strand (SEQ ID NO: 77) and 4I4N 3' antisense strand (SEQ ID NO: 78)). Lane 5 contains the DNA products from Experiment 16 after ligation and digestion (4I4N sense template to test thymine (SEQ ID NO: 79)+4I4N 5' antisense strand (SEQ ID NO: 77) and 4I4N 3' antisense strand (SEQ ID NO: 78)). Lane 6 contains the DNA products from Experiment 15 after ligation and digestion (4I4N sense template to test adenine (SEQ ID NO: 76)+4I4N 5' antisense strand (SEQ ID NO: 77) and 4I4N 3' antisense strand (SEQ ID NO: 78)). Lane 7 contains the DNA products from Experiment 17 after ligation and digestion (4I4N sense template to test cytidine (SEQ ID NO: 80)+4I4N 5' antisense strand (SEQ ID NO: 77) and 4I4N 3' antisense strand (SEQ ID NO: 78).

It was investigated if it was possible hybridise and ligate nucleotide oligomers, which contain deoxyinosines, together (FIG. 9). A sense template and 3' and 5' antisense strands were incubated together so that the antisense strands would hybridise to the sense template. The antisense strands were then ligated together and then exposed to ExoIII digestion. If ligation was successful a high molecular weight band would be observed on a PAGE gel corresponding to the ligated antisense strand. If the ligation was unsuccessful then a lower molecular weight band corresponding to the 3' antisense strand would be observed. Lane 1 of FIG. 10 shows the 3' antisense strand as a reference. Lane 2 and 3 show the negative control experiment (Experiment 2) and the positive control experiment (Experiment 1). As the negative control had no T4 DNA ligase enzyme added only the non-ligated product was observed, however, the positive control showed successful ligation. Experiments 3-18 were carried out to investigate how the spacing between the deoxyinosines (1I1N, 2I2N, 3I3N and 4I4N) affected the efficiency of the ligation reaction. The sense template strand sequence was altered in order to check that the deoxyinosines in the antisense strands would base pair to all four bases (adenosine, thymidine, cytidine and guanosine) in the sense strand. All of the strands tested showed ligated product in the PAGE gels. Experiments 14-18 are shown in FIG. 10 as an example. For the 4I4N experiments the deoxyinosines successfully base-paired to all four bases at the hybridisation stage. Therefore, the ligation was successful and ExoIII digestion resulted in digestion of the sense template strand only. These experiments show it is possible to ligate strands together which contain deoxyinosines in a variety of different patterns and that the deoxyinosines in the antisense strand can base-pair with all four DNA bases in the sense strand.

Example 4

Figure 11:
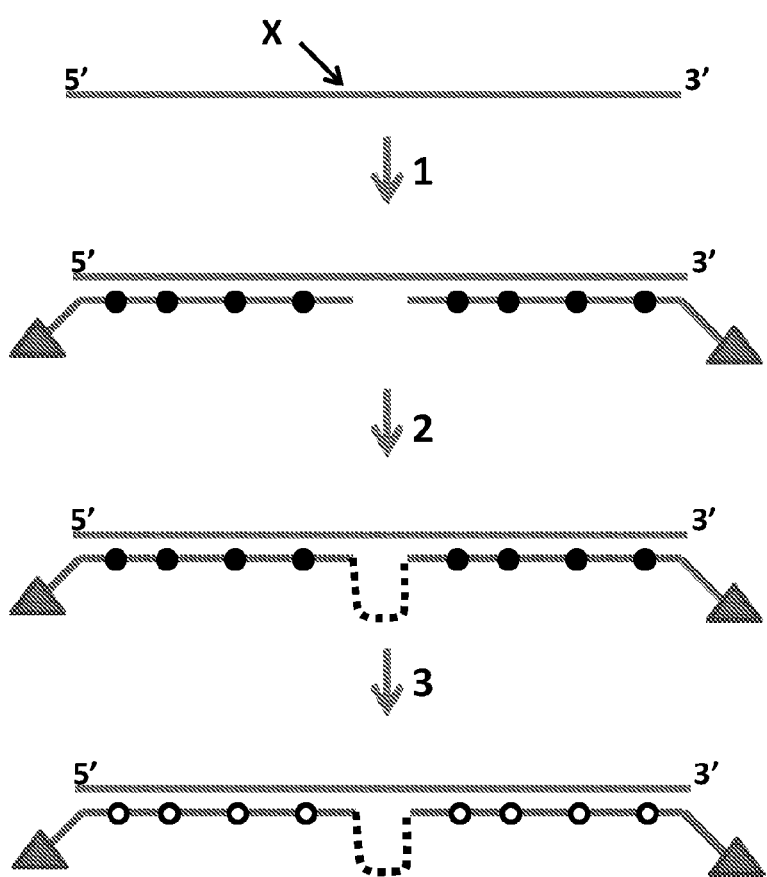
FIG. 11 shows an example sample modification method to prepare a strand of DNA for characterisation. Step 1 shows hybridisation of nucleotide oligomers to the sense template strand (labelled X). Step 2 shows ligation of the nucleotide oligomers Step 3 illustrates enzymatic removal of the hypoxanthine nucleobases in the antisense strand (this are shown in the lowest diagram as empty circles).

This example describes the hybridisation of nucleotide oligomers, which contain deoxyinosines, to a sense template polynucleotide strand, ligation of the nucleotide oligomers together and subsequent removal of the hypoxanthine nucleobases in the sequence (FIG. 11).

Materials and Methods 4.1—Hybridisation and Ligation of Nucleotide Oligomers to the Template Oligos are annealed to create the 3 fragment structure shown in step 1 of FIG. 11 (two antisense strands ligated to a sense strand to generate a nick to be repaired). The following reaction mixtures, detailed in Table 12 below, are prepared for the experiment sets described below. Oligos are annealed by heating to 98° C. for 2 minutes before being cooled to 18° C. at 2° C. per minute.

Experiment 1—positive control sense template (SEQ ID NO: 55)+positive control 5' antisense strand (SEQ ID NO: 56) and positive control 3' antisense strand (SEQ ID NO: 57)

Experiment 2—negative control sense template (SEQ ID NO: 55)+negative control 5' antisense strand (SEQ ID NO: 56) and negative control 3' antisense strand (SEQ ID NO: 57) in the absence of ligase.

Experiment 3—1I1N sense template to test adenine (SEQ ID NO: 58)+1I1N 5' antisense strand (SEQ ID NO: 59) and 1I1N 3' antisense strand (SEQ ID NO: 60)

Experiment 4—1I1N sense template to test thymine (SEQ ID NO: 61)+1I1N 5' antisense strand (SEQ ID NO: 59) and 1I1N 3' sense strand (SEQ ID NO: 60)

Experiment 5—1I1N sense template to test cytidine (SEQ ID NO: 62)+1I1N 5' antisense strand (SEQ ID NO: 59) and 1I1N 3' antisense strand (SEQ ID NO: 60)

Experiment 6—1I1N sense template to test guanosine (SEQ ID NO: 63)+1I1N 5' antisense strand (SEQ ID NO: 59) and 1I1N 3' antisense strand (SEQ ID NO: 60)

Experiment 7—2I2N sense template to test adenine (SEQ ID NO: 64)+2I2N 5' antisense strand (SEQ ID NO: 65) and 2I2N 3' antisense strand (SEQ ID NO: 66)

Experiment 8—2I2N sense template to test thymine (SEQ ID NO: 67)+2I2N 5' antisense strand (SEQ ID NO: 65) and 2I2N 3' antisense strand (SEQ ID NO: 66)

Experiment 9—2I2N sense template to test cytidine (SEQ ID NO: 68)+2I2N 5' antisense strand (SEQ ID NO: 65) and 2I2N 3' antisense strand (SEQ ID NO: 66)

Experiment 10—2I2N sense template to test guanosine (SEQ ID NO: 69)+2I2N 5' antisense strand (SEQ ID NO: 65) and 2I2N 3' antisense strand (SEQ ID NO: 66)

Experiment 11—3I3N sense template to test adenine (SEQ ID NO: 70)+3I3N 5' antisense strand (SEQ ID NO: 71) and 3I3N 3' antisense strand (SEQ ID NO: 72)

Experiment 12—3I3N sense template to test thymine (SEQ ID NO: 73)+3I3N 5' antisense strand (SEQ ID NO: 71) and 3I3N 3' antisense strand (SEQ ID NO: 72)

Experiment 13—3I3N sense template to test cytidine (SEQ ID NO: 74)+3I3N 5' antisense strand (SEQ ID NO: 71) and 3I3N 3' antisense strand (SEQ ID NO: 72)

Experiment 14—3I3N sense template to test guanosine (SEQ ID NO: 75)+3I3N 5' antisense strand (SEQ ID NO: 71) and 3I3N 3' antisense strand (SEQ ID NO: 72)

Experiment 15—4I4N sense template to test adenine (SEQ ID NO: 76)+4I4N 5' antisense strand (SEQ ID NO: 77) and 4I4N 3' antisense strand (SEQ ID NO: 78)

Experiment 16—4I4N sense template to test thymine (SEQ ID NO: 79)+4I4N 5' antisense strand (SEQ ID NO: 77) and 4I4N 3' antisense strand (SEQ ID NO: 78)

Experiment 17—4I4N sense template to test cytidine (SEQ ID NO: 80)+4I4N 5' antisense strand (SEQ ID NO: 77) and 4I4N 3' antisense strand (SEQ ID NO: 78)

Experiment 18—4I4N sense template to test guanosine (SEQ ID NO: 81)+4I4N 5' antisense strand (SEQ ID NO: 77) and 4I4N 3' antisense strand (SEQ ID NO: 78)

TABLE 12

| Reagent | Volume (μL) |
| --- | --- |
| 2M KCl | 0.5 |
| 100 uM sense template | 1 |
| 100 uM 5' antisense test strand | 1 |
| 100 uM 3' antisense test strand | 1 |
| nuclease free water | 16.5 |
| Total | 20 |

Ligation reactions are assembled as described in Table 13 (10× T4 DNA ligase buffer is made up of ~300 mM Tris-HCl pH 7.8, 100 mM DTT, 100 mM MgCl2 and 10 mM rATP) and 14 (2× Low fidelity (Lo-Fi) buffer is made up of 60 mM Tris-HCl pH 7.5, 20 mM DTT, 6 mM MgCl2, 20 mM rATP and 40% DMSO) below and incubated as described below for each experiment set.

Experiment 1 Incubation Conditions—Table 13 buffer conditions, 22° C., 1 hour.

Experiment 2 Incubation Conditions—Table 13 buffer conditions, 22° C., 1 hour in the absence of DNA ligase (16 μL of nuclease free water added).

Experiments 3, 4, 5 and 6 Incubation Conditions—Table 14 buffer conditions, 30° C., 18 hours.

Experiments 7, 8, 9 and 10 Incubation Conditions—Table 14 buffer conditions, 30° C., 18 hours.

Experiments 11, 12, 13 and 14 Incubation Conditions—Table 13 buffer conditions, 22° C., 18 hours.

Experiments 15, 16, 17 and 18 Incubation Conditions—Table 13 buffer conditions, 22° C., 1 hour.

TABLE 13

| Reagent | Volume (μL) |
| --- | --- |
| annealed DNA | 2 |
| 10× T4 DNA ligase buffer | 2 |
| T4 DNA ligase | 0.25 |
| nuclease free water | 15.75 |
| Total | 20 |

TABLE 14

| Reagent | Volume (μL) |
| --- | --- |
| annealed DNA | 2 |
| 2× Lo-Fi buffer | 10 |
| T4 DNA ligase | 0.25 |
| nuclease free water | 7.75 |
| Total | 20 |

4.2—Enzymatic Removal of the Hypoxanthine Nucleobases

Ligation products are subjected to human alkyladenine DNA glycosylase (hAAG) treatment in order to remove the hypoxanthine nucleobases. The following human alkyladenine DNA glycosylase reaction mixtures, detailed in Table 15 below (10× Reaction Buffer is made up of ~200 mM Tris-HCl pH 8.8, 100 mM (NH4)2SO4, 100 mM KCl and 20 mM MgSO4 and 1% Triton X-100), are added to eppendorfs (0.5 mL). The reaction mixtures are then incubated for 1 hour at 37° C.

TABLE 15

| Reagent | Volume (μL) |
| --- | --- |
| Experiment DNA (0.5 μM) | 15 |
| Reaction Buffer (10×) | 2 |
| Water | 2 |

TABLE 15-continued

| Reagent | Volume (µL) |
| --- | --- |
| Human alkyladenine DNA glycosylase (10 U/µL) | 1 |
| Total | 2 |

Results

Nucleotide oligomer strands are hybridised and ligated to the sense template strand as for Example 3. Double stranded DNA is generated on ligation of the deoxyinosine containing nucleotide oligomers, this can optionally be made into ssDNA by digestion with exonuclease III as detailed in Example 3 (SEQ ID No: 82 is an example). Finally, the hypoxanthine nucleobases are removed from the antisense strand using human alkyladenine DNA glycosylase. This enzyme removes the hypoxanthine nucleobase and leaves the sugar phosphate backbone intact, which results in defined abasic sites within the antisense strand at the positions of the deoxyinosines in the examples detailed in Example 3 (SEQ ID No: 83 is an example).

Example 5

Figure 12:
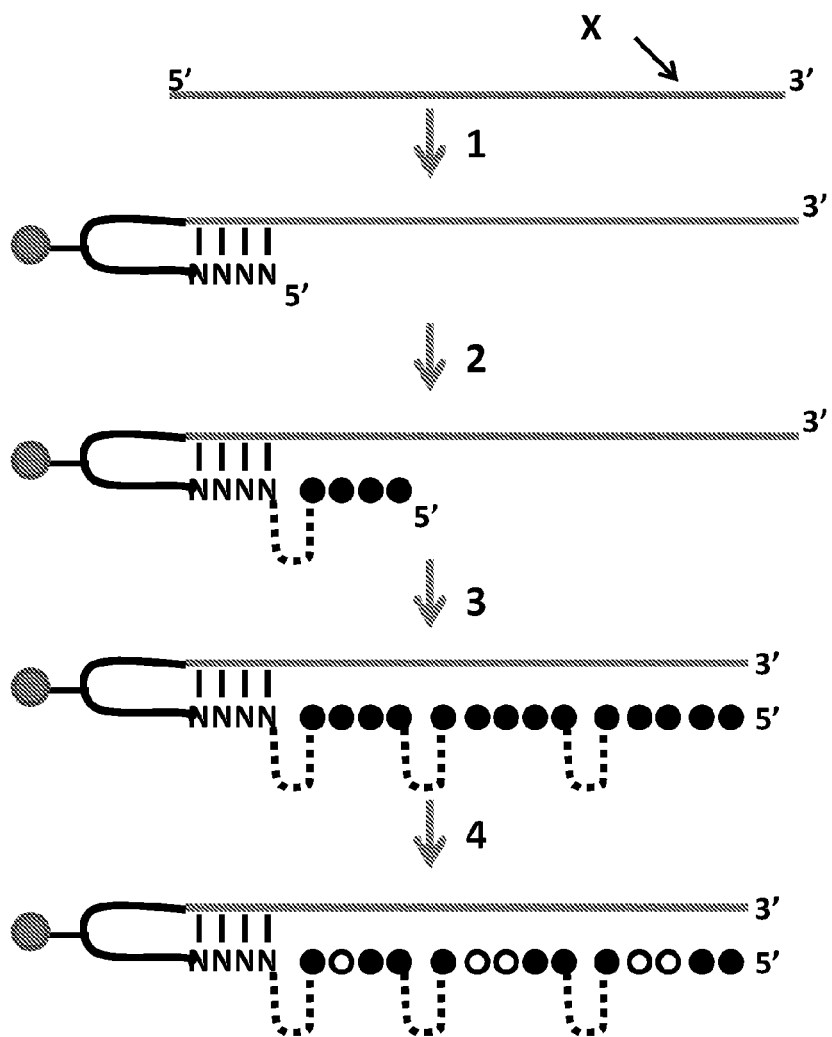
FIG. 12 shows an example sample modification method to prepare a strand of DNA for characterisation by nanopore sequencing. Step 1 shows hybridisation and ligation of a hairpin to one end of the sense template strand (labelled X). Step 2 shows the hybridisation of the nucleotide oligomers to the sense template and ligation to the hairpin which acts as a primer. Step 3 shows further ligation of additional nucleotide oligomers. Step 4 illustrates enzymatic removal of the hypoxanthine nucleobases in the antisense strand (this are shown in the lowest diagram as empty circles).

This example describes another sample modification method where a adapter hairpin is ligated to the sense template and acts as a primer for nucleotide oligomer ligation (see FIG. 12). In this example a hairpin adapter which contains a biotin modification (SEQ ID NO: 84) is ligated to the 5' end of the sense template (SEQ ID NO: 45). The biotin modification allows capture of the reaction products onto streptavidin-coated paramagnetic beads to aid purification if desired.

Materials and Methods 5.1—Hybridisation and Ligation of the Hairpin Adapter

The hairpin adapter (SEQ ID NOs: 84) is annealed to the sense template (SEQ ID NO: 85). The following reaction mixture, detailed in Table 16 below, is prepared. The hairpin adapter (SEQ ID NO: 84) is annealed by heating to 98° C. for 2 minutes before snap cooling on ice.

TABLE 16

| Reagent | Volume (µL) |
| --- | --- |
| 2M KCl | 0.5 |
| 100 uM sense template (SEQ ID NO: 85) | 1 |
| 100 uM haipin adapter (SEQ ID NO: 84) | 1 |
| nuclease free water | 17.5 |
| Total | 20 |

Ligation reactions are assembled as described in Table 17 (2× Low fidelity (Lo-Fi) buffer contains 60 mM Tris-HCl pH 7.5, 20 mM DTT, 6 mM MgCl2, 20 mM rATP and 40% DMSO) below and incubated as described below for each experiment set.

Experiment 1 Incubation Conditions—Table 17 buffer conditions, 30° C., 18 hours.

TABLE 17

| Reagent | Volume (µL) |
| --- | --- |
| annealed DNA (SEQ ID NOs: 85 and 84) | 2 |
| 2x Lo-Fi buffer | 10 |
| T4 DNA ligase | 0.25 |
| nuclease free water | 7.75 |
| Total | 20 |

5.2—Hybridisation and Ligation of the Nucleotide Oligomers to a Primer

Nucleotide oligomers (SEQ ID NOs: 86, 87, 88 and 89) are annealed to the sense template (SEQ ID NO: 85). The following reaction agents, detailed in Table 18 below, are prepared for experiment 1 described below. Nucleotide oligomers (SEQ ID NOs: 86, 87, 88 and 89) are annealed by heating to 98° C. for 2 minutes before cooling to 18° C. at 2° C. per minute. Experiment 1—sense template (SEQ ID NO: 85)+5' sense nucleotide oligomers (SEQ ID NOs: 86, 87, 88 and 89)

TABLE 18

| Reagent | Volume (µL) |
| --- | --- |
| 2M KCl | 0.5 |
| 100 uM sense template (SEQ ID NO: 84 and 85) | 1 |
| 100 uM SEQ ID NO: 86 | 1 |
| 100 uM SEQ ID NO: 87 | 1 |
| 100 uM SEQ ID NO: 88 | 1 |
| 100 uM SEQ ID NO: 89 | 1 |
| nuclease free water | 14.5 |
| Total | 20 |

Ligation reactions are assembled as described in Table 19 (10× Taq DNA Ligase Buffer contains 200 mM Tris-HCl pH 7.6, 100 mM DTT, 25 mM Potassium Acetate, 100 mM Magnessium Acetate, 10 mM NAD+ and 1% Triton X-100) below and incubated as described for experiment 1.

Experiment 1 Incubation Conditions—Reactions are heated to 65° C. for 1 min before cooling to 45° C. for 9 mins. This heating and cooling step is repeated 108 times for a total of 18 hours.

TABLE 19

| Reagent | Volume (µL) |
| --- | --- |
| annealed DNA (SEQ ID NOs: 84-89) | 2 |
| 10x Taq Ligase Buffer | 2 |
| Taq DNA ligase | 1 |
| nuclease free water | 15 |
| Total | 20 |

5.3—Enzymatic Removal of Hypoxanthine Nucleobases

The same procedure as described for example 4 is carried out.

Results

The hairpin adapter (SEQ ID NO: 84) is hybridised and ligated to the 5' end of the sense template strand (SEQ ID NO: 85). The hairpin adapter contains a biotin modification which allows easy replenishment of adapters if it is necessary to change buffer solution. The hairpin adapter (SEQ ID NO: 84) has an overhang of 4 nucleotides which hybridises to the sense template strand (SEQ ID NO: 85) before the ligase attaches the hairpin to the sense template. Nucleotide oligomer strands (SEQ ID NOs: 86, 87, 88 and 89) are then subsequently hybridised and ligated to the sense template strand (SEQ ID NO: 85). The conditions for the ligation include temperature cycling in the presence of a thermostable ligase (this is done so that unfavourable products not ligated to the hairpin are lost at high temperature) so that hairpin-mediated ligation is favoured (to form SEQ ID NO: 90) over template ligation that is not primed by the hairpin. Finally, the hypoxanthine nucleobases are removed using human alkyladenine DNA glycoyylase. This enzyme removes the hypoxanthine nucleobase and leaves the sugar phosphate backbone intact, this results in defined abasic sites within the sense strand (SEQ ID NO: 91). Linking of the sense template (SEQ ID NO: 85) to the ligated antisense strand (SEQ ID NO: 86, 87, 88 and 89) by the hairpin (SEQ ID NO: 84) allows characterisation of both strands in one experiment. This gives additional information which is used to characterise the strand sequence.

Example 6

Figure 13:
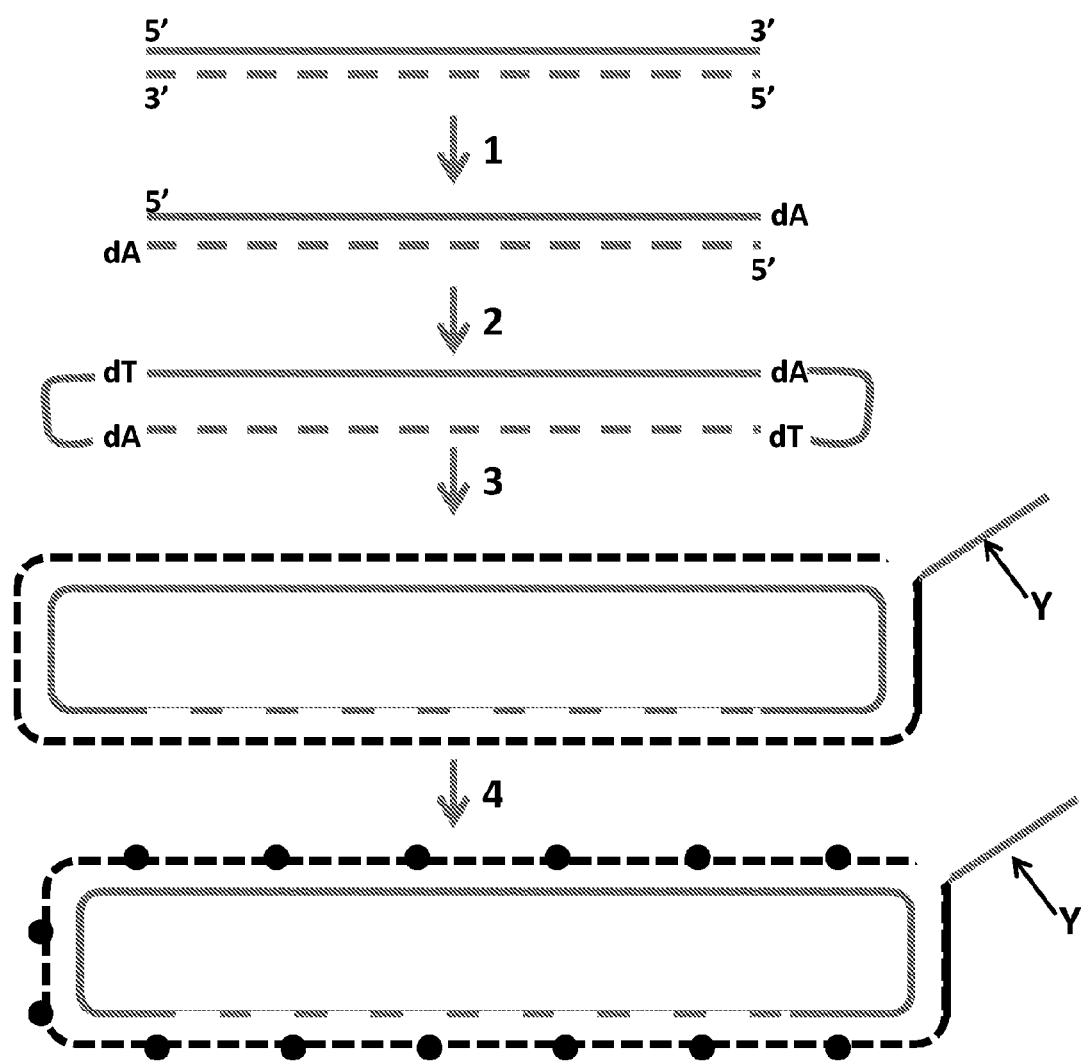
FIG. 13 shows and example sample modification method to prepare double-stranded DNA for characterisation by nanopore sequencing. Step 1 shows dA-tailing of the 3' ends of the sense and antisense strands. Step 2 shows the hybridisation and ligation of two dT-tailed hairpins forming a circular DNA template. Step 3 shows the hybridisation of a primer (which includes a leader sequence (labelled Y) which can be used to thread the ligated strand into the nanopore) and nucleotide oligomers (black dotted line) to the circular DNA template. Step 4 illustrates enzymatic removal of the hypoxanthine nucleobases in the antisense strand (the removed bases are shown in the lowest diagram as black circles).

This example describes a sample modification method to prepare double-stranded DNA (see FIG. 13). In this example hairpins (SEQ ID NO: 92 and 93) are attached at either end of the double-stranded DNA forming a circular DNA template (SEQ ID NO: 94 (sense), 92 (hairpin), 95 (antisense) and 93 (hairpin)). A primer (SEQ ID NO: 96) is then hybridised to the circular template, which acts as the point in the sequence at which ligation of the nucleotide oligomers (SEQ ID NOs:97-107) starts. The primer sequence includes a leader sequence which can be used to thread the ligated strand into the nanopore for characterisation.

Materials and Methods
6.1—dA-Tailing the Double-Stranded DNA Template

The sense target polynucleotide (SEQ ID NO: 94) is hybridised to the antisense target polynucleotide (SEQ ID NO: 95). Nucleotide oligomers (SEQ ID NOs: 94 and 95) are assembled as described in Table 20 and are annealed by heating to 98° C. for 2 minutes before cooling to 18° C. at 2° C. per minute.

TABLE 20

| Reagent | Volume (µL) |
| --- | --- |
| 2M KCl | 0.5 |
| 100 uM SEQ ID NO: 94 | 2 |
| 100 uM SEQ ID NO: 95 | 2 |
| nuclease free water | 15.5 |
| Total | 20 |

The double stranded DNA (SEQ ID NOs: 94 and 95) can then be dA-tailed using Klenow exo minus DNA polymerase to allow ease of ligation of hairpin adapters (SEQ ID NO: 53 and SEQ ID NO: 54). dA-tailing reactions are assembled as described in Table 21 (10× NEBNext dA-tailing Buffer contains 100 mM Tris-HCl pH 7.9, 100 mM MgCl2, 500 mM NaCl, 10 mM DTT and 2 mM dATP) below and incubated as described for experiment 1.

Experiment 1 Incubation Conditions—Reactions are assembled as described in Table 21 in 0.5 ml Eppendorfs and heated to 37° C. for 30 minutes.

TABLE 21

| Reagent | Volume (µL) |
| --- | --- |
| Annealed DNA (SEQ ID NO: 94 and 95) (10 uM) | 12.5 |

TABLE 21-continued

| Reagent | Volume (µL) |
| --- | --- |
| 10x NEBNext dA-tailing Buffer | 2.5 |
| Klenow exo minus | 1.5 |
| Nuclease free water | 8.5 |
| Total | 25 |

6.2—Hybridisation and Ligation of dT-tailed Hairpins

The dT-tailed hairpin adapters (SEQ ID NOs: 92 and 93) are annealed separately by heating to 98° C. for 2 minutes before snap cooling on ice to form the hairpin structures for each. Annealed dT-tailed hairpins (SEQ ID NO: 92 and SEQ ID NO: 93) are then ligated to the dA-tailed target double strand DNA (SEQ ID NO: 55 and SEQ ID NO: 56).

Ligation reactions are assembled as described in Table 22 (2× Low fidelity (Lo-Fi) buffer contains 60 mM Tris-HCl pH 7.5, 20 mM DTT, 6 mM MgCl2, 20 mM rATP and 40% DMSO) below and incubated as described below for experiment 1.

Experiment 1 Incubation Conditions—Table 22 buffer conditions, 30° C., 18 hours.

TABLE 22

| Reagent | Volume (µL) |
| --- | --- |
| Annealed dA-Tailed DNA (SEQ ID NO: 94 and 95) | 4 |
| Hairpin SEQ ID NO: 92 | 2 |
| Hairpin SEQ ID NO: 93 | 2 |
| Lo Fi Buffer | 10 |
| T4 DNA Ligase | 0.25 |
| Nuclease free water | 1.75 |
| Total | 20 |

6.3—Hybridisation and Ligation of the Primer and Nucleotide Oligomers

The same procedure as described for example 5 is carried out to ligate both the primer (SEQ ID NO: 57) and the nucleotide oligomers (SEQ ID NO: 58-68) to the circular DNA template SEQ ID NO: 94 (sense), 92 (hairpin), 95 (antisense) and 93 (hairpin)).

6.4—Enzymatic Removal of Hypoxanthine Nucleobases

The same procedure as described for example 4 is carried out.

Results

The double-stranded template is dA-tailed at the 3' end of the sense (SEQ ID NO: 94) and antisense (SEQ ID NO: 95) strands. dT-tailed hairpins (SEQ ID NO: 92 and 93) are attached at either end of the double-stranded DNA forming a circular DNA template (SEQ ID NO: 94 (sense), 92 (hairpin), 95 (antisense), 93 (hairpin)). A primer (SEQ ID NO: 96) is then hybridised to the circular template, which acts as the point in the sequence at which ligation of the nucleotide oligomers (SEQ ID NOs: 97-107) starts. The primer sequence includes a leader sequence which can be used to thread the ligated strand into the nanopore. The nucleotide oligomers (SEQ ID NOs:97-107) are then hybridised to the template and ligated to the primer. Finally, the hypoxanthine nucleobases present in the ligated strand are enzymatically removed. Linking of the sense and antisense strands of the double-stranded template (SEQ ID NO: 94 and 95) by the hairpins (SEQ ID NO: 92 and 93), in the arrangement shown in FIG. 13, allows characterisation of the ligated reverse complement strand whose sequence relates to the sequence of both the sense and antisense strands of the template. This gives additional information which is used to characterise the strand sequence.

Example 7

Figure 14:
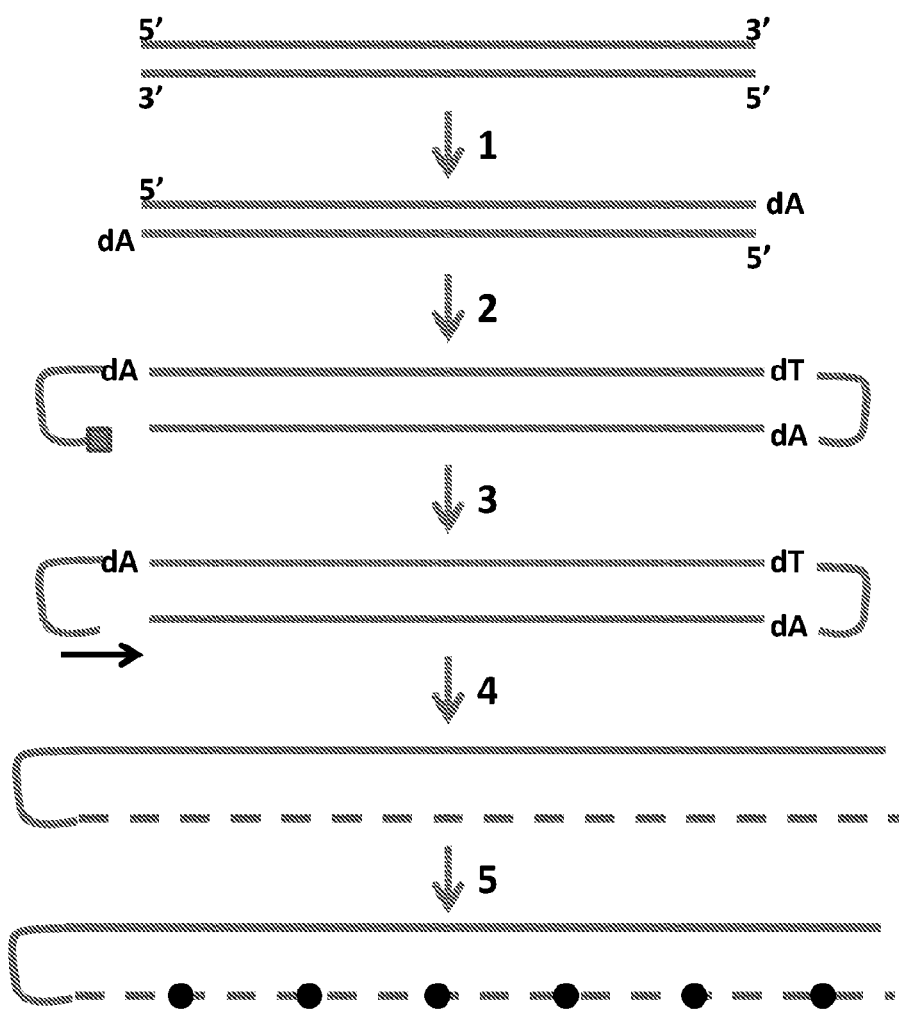
FIG. 14 shows and example sample modification method to prepare double-stranded DNA for characterisation by nanopore sequencing. Step 1 shows dA-tailing of the 3' ends of the sense and antisense strands. Step 2 shows the hybridisation and ligation of one dT-tailed hairpin which joins the sense and antisense strands at one end and the hybridisation and ligation of another hairpin at only the 5' end of the sense strand. The 5' end of the other hairpin is lacking a phosphate group (shown as a grey square) which prevents ligation to the antisense strand of the double-stranded template. Step 3 shows the addition of a 5' phosphate group to the end of the hairpin using T4 polynucleotide kinase (shown as removal of the grey square). Step 4 shows the hybridisation of the nucleotide oligomers to the circular template and ligation to the hairpin primer (the direction of nucleotide oligomer ligation is indicated by a black arrow). Step 5 illustrates enzymatic removal of the hypoxanthine nucleobases in the antisense strand (the removed bases are shown in the lowest diagram as black circles).

This example describes a sample modification method to prepare double-stranded DNA for characterisation by nanopore sequencing (see FIG. 14). In this example, hairpins (SEQ ID NO: 92 and 108) are attached at either end of the double-stranded DNA (SEQ ID NO: 94 (sense) and 95 (antisense)). One of the hairpins (SEQ ID NO: 108) only links to the DNA template at one end (the 5' end of the sense strand SEQ ID NO: 94) as the 5' end of the hairpin does not have a 5' phosphate attached. A 5' phosphate is then added to the hairpin, using T4 polynucleotide kinase, so that the second hairpin can act as a primer (SEQ ID NO: 108) at which ligation of the nucleotide oligomers (SEQ ID NOs: 97-68) starts.

Materials and Methods 7.1—dA-tailing the Double-Stranded DNA Template

The same procedure as described for example 6 is carried out.

7.2—Hybridisation and Ligation of Hairpins

The same procedure as described for example 6 is carried out using hairpins SEQ ID NO: 92 and SEQ ID NO: 108.

7.3—Addition of a 5' Phosphate Using T4 Polynucleotide Kinase

The ligated polynucleotide is 5' phosphorylated using Thermophage polynucleotide kinase, (Prokazyme). Phosphorylation reactions are assembled as described in Table 23 (10× Thermophage PNK Buffer contains 500 mM MOPS pH 8.5, 10 mM DTT, 100 mM MgCl2, 100 mM KCl) below and incubated as described for experiment 1.

Experiment 1 Incubation Conditions—Reactions are assembled as described in Table 23 in 0.5 ml Eppendorfs and heated to 70° C. for one hour.

TABLE 23

| Reagent | Volume (μL) |
| --- | --- |
| Ligation reaction product (SEQ ID NOs: 92, 94, 95 and 108) | 12.6 |
| 10× ThermoPhage Buffer | 2 |
| ATP (10 mM) | 0.2 |
| PNK (25 U/ul) | 1 |
| BSA (2.5 mg/ml) | 0.2 |
| PEG 6000 (25%) | 4 |
| Total | 20 |

7.4—Hybridisation and Ligation of the Nucleotide Oligomers to a Primer

The same procedure as described for example 5 is carried out.

7.5—Enzymatic Removal of Hypoxanthine Nucleobases

The same procedure as described for example 4 is carried out.

Results

The double-stranded template is dA-tailed at the 3' end of the sense (SEQ ID NO: 94) and antisense (SEQ ID NO: 95) strands. One dT-tailed hairpin (SEQ ID NO: 92) is attached to the sense and antisense strands at one end of the double-stranded DNA. At the other end of the template, the hairpin (SEQ ID NO: 108) attaches at the 5' end of the sense strand only as the hairpin is missing a phosphate group at its 5' end preventing attachment to the 3' end of the antisense strand of the template (SEQ ID NO: 95). This 5' phosphate is then added using T4 polynucleotide kinase so that the second hairpin can then act as a primer (SEQ ID NO: 108) at which ligation of the nucleotide oligomers (SEQ ID NOs: 97, 98, 99, 100, 101, 102, 103, 104, 105, 106, 107) starts. Finally, the hypoxanthine nucleobases present in the strand are then enzymatically removed. Linking of the sense and antisense strands of the double-stranded template (SEQ ID NO: 94 and 95) by the hairpins (SEQ ID NO: 92 and 108), in the arrangement shown in FIG. 14, allows characterisation of the original double-stranded template as well as the ligated reverse complement which has abasic residues where the deoxyinosines were located. This gives additional information which is used to characterise the strand sequence.

Example 8

This example describes a means to generate a suitable overhang for strand sequencing, if the generated template is double stranded DNA. A 5' overhang can be added either during the ligation on one of the terminal adapters, as in Examples 1, 2 and 6, or to blunt ended DNA after ligation by exonuclease III digestion, such as in Examples 3, 4, 5 and 7. Reactions are assembled as described in Table 24 below. Reactions were left to proceed for 5 mins at 22° C. before being quenched by addition of 0.5 M EDTA to a final concentration of 0.1 M.

TABLE 24

| Reagent | Volume (μL) |
| --- | --- |
| ligation reaction product | 17 |
| 10× NEBuffer 1 | 2 |
| 10 U ul$^{-1}$ ExoIII | 1 |
| nuclease free water | 0 |
| Total | 20 |

---

The invention claimed is:

1. A method for modifying a template polynucleotide for characterization, comprising:
   (a) contacting the template polynucleotide with a population of nucleotide oligomers under conditions in which the oligomers can hybridise to the polynucleotide, wherein all of the oligomers in the population (i) have from 2 to 16 nucleotides and (ii) share a same pattern, wherein the same pattern comprises one or more instances of $Z_XN_Y$ and/or $N_YZ_X$ where Z is a universal nucleotide and/or an abasic nucleotide, N is a nucleotide which is complementary to one of the nucleotides in the template polynucleotide, X is 1, 2, 3 or 4 and Y is 1, 2, 3 or 4 and wherein the population comprises every possible combination of nucleotides N which are complementary to all of the nucleotides in the template polynucleotide; and
   (b) ligating together those oligomers that hybridise to the polynucleotide and thereby providing a modified polynucleotide for characterisation.

2. A method according to claim 1, wherein
   (i) all of the oligomers in the population comprise 2, 3, 4, 5, 6, 7 or 8 instances of $Z_XN_Y$ and/or $N_YZ_X$;
   (ii) X and/or Y are the same in different instances of $Z_XN_Y$ and/or $N_YZ_X$;
   (iii) X and/or Y are different in different instances of $Z_XN_Y$ and/or $N_YZ_X$; or
   (iv) in at least one instance of $Z_XN_Y$ and/or $N_YZ_X$:
      (a) X is 1 and Y is 1;
      (b) X is 2 and Y is 2;

(c) X is 3 and Y is 3;
(d) X is 4 and Y is 4;
(e) X is 2 and Y is 1;
(f) X is 1 and Y is 2;
(g) X is 3 and Y is 1; or
(h) X is 1 and Y is 3.

3. A method according to claim 1, wherein
(i) all of the oligomers in the population comprise one or more instances of $Z_X N_Y$ or one or more instances of $N_Y Z_X$;
(ii) all of the oligomers in the population comprise one or more instances of $Z_X N_Y$ or one or more instances of $N_Y Z_X$ and each of the one or more instances of $Z_X N_Y$ or each of the one or more instances of $N_Y Z_X$ are identical in terms of X and Y; or
(iii) all of the oligomers in the population comprise:
(a) ZN-ZN-ZN-ZN-ZN-ZN;
(b) NZ-NZ-NZ-NZ-NZ-NZ;
(c) ZZNN-ZZNN-ZZNN;
(d) NNZZ-NNZZ-NNZZ;
(e) ZZZNNN-ZZZNNN;
(f) NNNZZZ-NNNZZZ;
(g) ZZZZNNNN-ZZZZNNNN;
(h) NNNNZZZZ-NNNNZZZZ;
(i) ZN-ZN-ZN-ZN;
(j) NZ-NZ-NZ-NZ;
(k) ZZNN-ZZNN;
(l) NNZZ-NNZZ;
(m) ZZZZNNNN;
(n) NNNNZZZZ;
(o) ZZN-ZZN-ZZN;
(p) NNZ-NNZ-NNZ;
(q) ZZZN-ZZZN-ZZZN-ZZZN;
(r) NNNZ-NNNZ-NNNZ-NNNZ;
(s) ZZZN-ZZZN-ZZZN; or
(t) NNNZ-NNNZ-NNNZ.

4. A method according to claim 1, wherein
(i) all of the oligomers in the population comprise one or more instances of $Z_X N_Y$ and one or more instances of $N_Y Z_X$; or
(ii) all of the oligomers in the population comprise:
(a) NZ-ZNN-ZZNN-ZZN;
(b) ZN-NZZ-NNZZ-NNZ;
(c) NNZZ-ZZNN-NNNZZZ-ZNN;
(d) ZZNN-NNZZ-ZZZNNN-NZZ;
(e) NNZZ-ZZNN;
(f) ZZNN-NNZZ;
(g) NZZ-NNZ-ZNN-ZZN;
(h) ZNN-ZZN-NZZ-NNZ;
(i) NZZ-NNZ-ZN; or
(j) ZNN-ZZN-NZ.

5. A method according to claim 1, wherein the universal nucleotide Z comprises a hypoxanthine, 4-nitroindole, 5-nitroindole, 6-nitroindole, 3-nitropyrrole, nitroimidazole, 4-nitropyrazole, 4-nitrobenzimidazole, 5-nitroindazole, 4-aminobenzimidazole, or phenyl (C6-aromatic) ring.

6. A method according to claim 1, wherein
(i) Z is a universal nucleotide and the method further comprises (c) selectively removing the nucleobases from the universal nucleotides in the ligated polynucleotide and thereby providing a modified polynucleotide for characterization or
(ii) Z is an abasic nucleotide and wherein the ratio of X to Y is at least 1:2.

7. A method according to claim 1, wherein:
(i) N comprises adenine (A), uracil (U), guanine (G) or cytosine (C) and the population comprises every possible combination of A, U, G and C; or
(ii) N comprises A, thymine (T), G or C and the population comprises every possible combination of A, T, G and C.

8. A method according to claim 1, wherein all of the oligomers in the population (iii) have a phosphate group or an adenylate group at the 5' end.

9. A method according to claim 1, wherein the template polynucleotide is single stranded.

10. A method according to claim 9, wherein the method further comprises before step (a) ligating a hairpin adaptor to one end of the template polynucleotide such that the ligated hairpin adaptor provides a degenerate overhang and wherein step (b) comprises ligating together the oligomers that hybridise to the polynucleotide using the degenerate overhang as a primer and wherein the hairpin adaptor optionally comprises a selectable binding moiety.

11. A method according to claim 1, wherein the template polynucleotide is double stranded.

12. A method according to claim 11, wherein
(i) the method further comprises before step (a) ligating a first hairpin adaptor to one end of the template polynucleotide and ligating a second hairpin adaptor to the other end of the template polynucleotide to form a circular polynucleotide construct and wherein the first or second hairpin adaptor optionally comprises a selectable binding moiety;
(ii) the method further comprises before step (a) ligating a first hairpin adaptor to one end of the template polynucleotide and ligating a second hairpin adaptor to the other end of the template polynucleotide to form a circular polynucleotide construct, wherein the first or second hairpin adaptor optionally comprises a selectable binding moiety, wherein the second hairpin adaptor comprises a primer hybridisation region and an abasic region comprising one or more abasic nucleotides and wherein step (b) comprises ligating together the oligomers that hybridise to the circular polynucleotide construct using the second hairpin adaptor as the prime for ligation and thereby producing a polynucleotide circular construct that is substantially double stranded; or
(iii) the method further comprises before step (a) ligating a first hairpin adaptor to one end of the template polynucleotide and ligating a second hairpin adaptor to the other end of the template polynucleotide to form a circular polynucleotide construct, wherein the first or second hairpin adaptor optionally comprises a selectable binding moiety, wherein the second hairpin adaptor comprises a primer hybridisation region and an abasic region comprising one or more abasic nucleotides, wherein step (b) comprises ligating together the oligomers that hybridise to the circular polynucleotide construct using the second hairpin adaptor as the prime for ligation and thereby producing a polynucleotide circular construct that is substantially double stranded, wherein the second hairpin adaptor further comprises a region at which the hairpin can be cut and wherein the method further comprises before step (c) cutting the second hairpin adaptor to open the circular polynucleotide construct and produce a double stranded polynucleotide.

13. A method according to claim 1, wherein the method further comprises as step (d) repeating steps (a) to (c) at least once such that the ligation in each repetition begins at a different nucleotide on the template polynucleotide and thereby producing a plurality of different modified polynucleotides.

14. A method according to claim 13, wherein the template polynucleotide is single stranded, wherein the method further comprises before step (a) in each repetition ligating a hairpin adaptor to one end of the template polynucleotide such that the ligated hairpin adaptor provides a degenerate overhang, wherein step (b) comprises ligating together the oligomers that hybridise to the polynucleotide using the degenerate overhang as a primer and wherein the degenerate overhang is a different length in each repetition.

15. A method according to claim 13, wherein the template polynucleotide is double stranded wherein the method further comprises before step (a) ligating a first hairpin adaptor to one end of the template polynucleotide and ligating a second hairpin adaptor to the other end of the template polynucleotide to form a circular polynucleotide construct wherein step (b) comprises ligating together the oligomers that hybridise to the circular polynucleotide construct using the second hairpin adaptor as the prime for ligation and wherein the length of the first hairpin adaptor is different in each repetition.

16. A plurality of polynucleotides modified using a method according to claim 13.

17. A method of characterising a template polynucleotide, comprising:
   a) modifying the template polynucleotide using a method according to claim 13 to produce a plurality of different modified polynucleotides;
   b) contacting each modified polynucleotide with a transmembrane pore such that each polynucleotide moves through the pore; and
   c) taking one or more measurements as each polynucleotide moves with respect to the pore wherein the measurements are indicative of one or more characteristics of the polynucleotide and thereby characterising the template polynucleotide.

18. A method according to claim 17, wherein the one or more characteristics are selected from (i) the length of the polynucleotide, (ii) the identity of the polynucleotide, (iii) the sequence of the polynucleotide, (iv) the secondary structure of the polynucleotide and (v) whether or not the polynucleotide is modified.

19. A method according to claim 17, wherein
   step (a) further comprises contacting each polynucleotide with a polynucleotide binding protein such that the protein controls the movement of each polynucleotide through the pore; or
   the method comprises (a) contacting each polynucleotide with a transmembrane pore and a polynucleotide binding protein such that each polynucleotide moves through the pore and the protein controls the movement of each polynucleotide through the pore; and
   (b) measuring the current passing through the pore as each polynucleotide moves with respect to the pore wherein the current is indicative of one or more characteristics of each polynucleotide and thereby characterising the template polynucleotide.

20. A method according to claim 19, wherein the polynucleotide binding protein is derived from a helicase.

21. A polynucleotide modified using a method according to claim 1.

22. A method of characterising a polynucleotide modified using a method according to claim 1, comprising:
   a) contacting the modified polynucleotide with a transmembrane pore such that the polynucleotide moves through the pore; and
   b) taking one or more measurements as the polynucleotide moves with respect to the pore wherein the measurements are indicative of one or more characteristics of the polynucleotide and thereby characterising the modified polynucleotide.

23. A method according to claim 1, wherein the universal nucleotide Z comprises a nucleoside selected from the group consisting of: 2'-deoxyinosine, inosine, 7-deaza-2'-deoxyinosine, 7-deaza-inosine, 2-aza-deoxyinosine, 2-aza-inosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, and phenyl C-2'-deoxyribosyl nucleoside.

24. A population of nucleotide oligomers comprising oligomers (i) having from 2 to 16 nucleotides and (ii) sharing a same pattern, wherein the same pattern comprises one or more instances of $Z_XN_Y$ and/or $N_YZ_X$ where Z is a universal nucleotide and/or an abasic nucleotide, each N is independently a nucleotide which is complementary to A, G, T or U, or C, X is 1, 2, 3 or 4 and Y is 1, 2, 3 or 4 and wherein the population comprises every possible combination of nucleotides N.

25. A kit comprising (a) a population of nucleotide oligomers, the population comprising oligomers (i) having from 2 to 16 nucleotides and (ii) sharing a same pattern, wherein the same pattern comprises one or more instances of $Z_XN_Y$ and/or $N_YZ_X$ where Z is a universal nucleotide and/or an abasic nucleotide, each N is independently a nucleotide which is complementary to A, G, T or U, or C, X is 1, 2, 3 or 4 and Y is 1, 2, 3 or 4 and wherein the population comprises every possible combination of nucleotides N and (b) a ligase enzyme.

26. A method for modifying a template polynucleotide for characterization, comprising:
   (a) contacting the template polynucleotide with a population of nucleotide oligomers under a condition in which the oligomers can hybridize to the template polynucleotide, wherein the oligomers in the population (i) have a length of 2 to 16 nucleotides; and (ii) comprise an identical pattern of Z(s) and N(s), wherein the pattern is a sequence having one or more instances of $Z_XN_Y$, and/or $N_YZ_X$, wherein
   x in each instance is independently 1, 2, 3, or, 4,
   y in each instance is independently 1, 2, 3, or 4,
   each Z is independently a universal nucleotide or an abasic nucleotide;
   each N is independently a nucleotide specifically complementary with A, G, T or U, or C, and
   (b) ligating together the oligomers that hybridize to the template polynucleotide and thereby providing a modified polynucleotide for characterization.

27. The method of claim 26, wherein the population comprises every possible combination of nucleotides N.

* * * * *

SEQUENCE LISTING

```
<160> NUMBER OF SEQ ID NOS: 138

<210> SEQ ID NO 1
<211> LENGTH: 558
<212> TYPE: DNA
<213> ORGANISM: Artificial sequence
<220> FEATURE:
<223> OTHER INFORMATION: MspA MS-B1

<400> SEQUENCE: 1
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
```

```
tggtttcatt ccggtcgcgc aaaatatatc gtcgcaggcc cgggtgctga cgaattcgaa        180
ggcacgctgg aactgggtta tcagattggc tttccgtggt cactgggcgt tggtatcaac        240
ttctcgtaca ccacgccgaa tattctgatc aacaatggta acattaccgc accgccgttt        300
ggcctgaaca gcgtgattac gccgaacctg tttccgggtg ttagcatctc tgcccgtctg        360
ggcaatggtc cgggcattca agaagtggca acctttagtg tgcgcgtttc cggcgctaaa        420
ggcggtgtcg cggtgtctaa cgcccacggt accgttacgg gcgcggccgg cggtgtcctg        480
ctgcgtccgt tcgcgcgcct gattgcctct accggcgaca gcgttacgac ctatggcgaa        540
ccgtggaata tgaactaa                                                     558
```

<210> SEQ ID NO 2
<211> LENGTH: 184
<212> TYPE: PRT
<213> ORGANISM: Artificial sequence
<220> FEATURE:
<223> OTHER INFORMATION: MspA MS-B1

<400> SEQUENCE: 2

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 3
<211> LENGTH: 885
<212> TYPE: DNA
<213> ORGANISM: Artificial sequence
<220> FEATURE:
<223> OTHER INFORMATION: alpha-hemolysin-NN

<400> SEQUENCE: 3

```
atggcagatt ctgatattaa tattaaaacc ggtactacag atattggaag caatactaca         60
gtaaaaacag gtgatttagt cacttatgat aaagaaatgg catgcacaa aaaagtattt        120 tatagtttta tcgatgataa aaatcacaat aaaaaactgc tagttattag aacaaaaggt        180
accattgctg gtcaatatag agtttatagc gaagaaggtg ctaacaaaag tggtttagcc        240
```

```
tggccttcag cctttaaggt acagttgcaa ctacctgata atgaagtagc tcaaatatct    300
gattactatc aagaaattc gattgataca aaaaactata tgagtacttt aacttatgga    360
ttcaacggta atgttactgg tgatgataca ggaaaaattg gcggccttat tggtgcaaat    420
gtttcgattg gtcatacact gaactatgtt caacctgatt tcaaaacaat tttagagagc    480
ccaactgata aaaagtagg ctggaaagtg atatttaaca atatggtgaa tcaaaattgg    540
ggaccatacg atcgagattc ttggaacccg gtatatggca atcaactttt catgaaaact    600
agaaatggtt ctatgaaagc agcagataac ttccttgatc ctaacaaagc aagttctcta    660
ttatcttcag ggttttcacc agacttcgct acagttatta ctatggatag aaaagcatcc    720
aaacaacaaa caatataga tgtaatatac gaacgagttc gtgatgatta ccaattgcat    780
tggacttcaa caaattggaa aggtaccaat actaaagata aatggacaga tcgttcttca    840
gaaagatata aaatcgattg ggaaaaagaa gaaatgacaa attaa                   885

<210> SEQ ID NO 4
<211> LENGTH: 293
<212> TYPE: PRT
<213> ORGANISM: Artificial sequence
<220> FEATURE:
<223> OTHER INFORMATION: alpha-hemolysin-NN

<400> SEQUENCE: 4

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
```

```
                    245                 250                 255
Gln Leu His Trp Thr Ser Thr Asn Trp Lys Gly Thr Asn Thr Lys Asp
                260                 265                 270

Lys Trp Thr Asp Arg Ser Ser Glu Arg Tyr Lys Ile Asp Trp Glu Lys
            275                 280                 285

Glu Glu Met Thr Asn
        290

<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
```

```
            85                  90                  95
Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
            115                 120                 125

Ala Thr Phe Ser Val Asp Val Ser Gly Pro Ala Gly Val Ala Val
            130                 135             140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                    165                 170                 175

Tyr Gly Glu Pro Trp Asn Met Asn
            180

<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
            115                 120                 125

Thr Phe Ser Val Asp Val Lys Gly Ala Lys Gly Ala Val Ala Val Ser
        130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180

<210> SEQ ID NO 8
<211> LENGTH: 1830
<212> TYPE: DNA
<213> ORGANISM: Bacteriophage phi-29

<400> SEQUENCE: 8
atgaaacaca tgccgcgtaa aatgtatagc tgcgcgtttg aaaccacgac caaagtggaa       60
gattgtcgcg tttgggccta tggctacatg aacatcgaag atcattctga atacaaaatc      120
ggtaacagtc tggatgaatt tatggcatgg gtgctgaaag ttcaggcgga tctgtacttc      180
cacaacctga aatttgatgg cgcattcatt atcaactggc tggaacgtaa tggctttaaa      240
```

```
tggagcgcgg atggtctgcc gaacacgtat aataccatta tctctcgtat gggccagtgg      300
tatatgattg atatctgcct gggctacaaa ggtaaacgca aaattcatac cgtgatctat      360
gatagcctga aaaaactgcc gtttccggtg aagaaaattg cgaaagattt caaactgacg      420
gttctgaaag cgatattga ttatcacaaa gaacgtccgg ttggttacaa atcaccccg        480
gaagaatacg catacatcaa aaacgatatc cagatcatcg cagaagcgct gctgattcag      540
tttaaacagg gcctggatcg catgaccgcg ggcagtgata gcctgaaagg tttcaaagat      600
atcatcacga ccaaaaaatt caaaaaagtg ttcccgacgc tgagcctggg tctggataaa      660
gaagttcgtt atgcctaccg cggcggtttt acctggctga cgatcgtttt caagaaaaaa      720
gaaattggcg agggtatggt gtttgatgtt aatagtctgt atccggcaca gatgtacagc      780
cgcctgctgc gtatggcga accgatcgtg ttcgagggta atatgtttg ggatgaagat       840
tacccgctgc atattcagca catccgttgt gaatttgaac tgaagaagg ctatattccg        900
accattcaga tcaaacgtag tcgcttctat aagggtaacg aatacctgaa aagctctggc      960
ggtgaaatcg cggatctgtg gctgagtaac gtggatctgg aactgatgaa agaacactac     1020
gatctgtaca acgttgaata catcagcggc ctgaaattta aagccacgac cggtctgttc     1080
aaagatttca tcgataaatg gacctacatc aaaacgacct ctgaaggcgc gattaaacag     1140
ctggccaaac tgatgctgaa cagcctgtat ggcaaattcg cctctaatcc ggatgtgacc     1200
ggtaaagttc cgtacctgaa agaaaatggc gcactgggtt ttcgcctggg cgaagaagaa     1260
acgaaagatc cggtgtatac cccgatgggt gttttcatta cggcctgggc acgttacacg     1320
accatcaccg cggcccaggc atgctatgat cgcattatct actgtgatac cgattctatt     1380
catctgacgg gcaccgaaat cccgatgtg attaaagata tcgttgatcc gaaaaaactg     1440
ggttattggg cccacgaaag tacgtttaaa cgtgcaaaat acctgcgcca gaaaacctac     1500
atccaggata tctacatgaa agaagtggat ggcaaactgg ttgaaggttc tccggatgat     1560
tacaccgata tcaaattcag tgtgaaatgc gccggcatga cggataaaat caaaaaagaa     1620
gtgaccttcg aaaacttcaa agttggtttc agccgcaaaa tgaaccgaa accggtgcag     1680
gttccgggcg tgtggttct ggtggatgat acgtttacca ttaaatctgg cggtagtgcg     1740
tggagccatc cgcagttcga aaaggcggt ggctctggtg gcggttctgg cggtagtgcc      1800
tggagccacc cgcagtttga aaaataataa                                      1830
```

<210> SEQ ID NO 9
<211> LENGTH: 608
<212> TYPE: PRT
<213> ORGANISM: Bacteriophage phi-29

<400> SEQUENCE: 9

Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg

```
                    85                  90                  95
Met Gly Gln Trp Tyr Met Ile Asp Ile Cys Leu Gly Tyr Lys Gly Lys
                100                 105                 110
Arg Lys Ile His Thr Val Ile Tyr Asp Ser Leu Lys Lys Leu Pro Phe
                115                 120                 125
Pro Val Lys Lys Ile Ala Lys Asp Phe Lys Leu Thr Val Leu Lys Gly
                130                 135                 140
Asp Ile Asp Tyr His Lys Glu Arg Pro Val Gly Tyr Lys Ile Thr Pro
145                 150                 155                 160
Glu Glu Tyr Ala Tyr Ile Lys Asn Asp Ile Gln Ile Ile Ala Glu Ala
                165                 170                 175
Leu Leu Ile Gln Phe Lys Gln Gly Leu Asp Arg Met Thr Ala Gly Ser
                180                 185                 190
Asp Ser Leu Lys Gly Phe Lys Asp Ile Ile Thr Thr Lys Lys Phe Lys
                195                 200                 205
Lys Val Phe Pro Thr Leu Ser Leu Gly Leu Asp Lys Glu Val Arg Tyr
                210                 215                 220
Ala Tyr Arg Gly Gly Phe Thr Trp Leu Asn Asp Arg Phe Lys Glu Lys
225                 230                 235                 240
Glu Ile Gly Glu Gly Met Val Phe Asp Val Asn Ser Leu Tyr Pro Ala
                245                 250                 255
Gln Met Tyr Ser Arg Leu Leu Pro Tyr Gly Glu Pro Ile Val Phe Glu
                260                 265                 270
Gly Lys Tyr Val Trp Asp Glu Asp Tyr Pro Leu His Ile Gln His Ile
                275                 280                 285
Arg Cys Glu Phe Glu Leu Lys Glu Gly Tyr Ile Pro Thr Ile Gln Ile
                290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
                340                 345                 350
Phe Lys Ala Thr Thr Gly Leu Phe Lys Asp Phe Ile Asp Lys Trp Thr
                355                 360                 365
Tyr Ile Lys Thr Thr Ser Glu Gly Ala Ile Lys Gln Leu Ala Lys Leu
                370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
                420                 425                 430
Ile Thr Ala Trp Ala Arg Tyr Thr Thr Ile Thr Ala Ala Gln Ala Cys
                435                 440                 445
Tyr Asp Arg Ile Ile Tyr Cys Asp Thr Asp Ser Ile His Leu Thr Gly
                450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                485                 490                 495
Gln Lys Thr Tyr Ile Gln Asp Ile Tyr Met Lys Glu Val Asp Gly Lys
                500                 505                 510
```

Leu Val Glu Gly Ser Pro Asp Tyr Thr Asp Ile Lys Phe Ser Val
    515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Gly Ser
            580                 585                 590

Gly Gly Gly Ser Gly Gly Ser Ala Trp Ser His Pro Gln Phe Glu Lys
        595                 600                 605

<210> SEQ ID NO 10
<211> LENGTH: 1390
<212> TYPE: DNA
<213> ORGANISM: Escherichia coli

<400> SEQUENCE: 10

```
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg cgaaccggaa agtgttttat gcaaaccggc cgatgattta tctgccgcag     180
ccgggtgcgg tgctgattac cggtattacc ccgcaggaag cgcgcgcgaa aggtgaaaac     240
gaagcggcgt ttgccgcgcg cattcatagc ctgtttaccg tgccgaaaac ctgcattctg     300
ggctataaca atgtgcgctt cgatgatgaa gttacccgta atatctttta tcgtaacttt     360
tatgatccgt atgcgtggag ctggcagcat gataacagcc gttgggatct gctggatgtg     420
atgcgcgcgt gctatgcgct cgcccggaa ggcattaatt ggccggaaaa cgatgatggc     480
ctgccgagct ttcgtctgga acatctgacc aaagccaacg gcattgaaca tagcaatgcc     540
catgatgcga tggccgatgt ttatgcgacc attgcgatgg cgaaactggt taaaacccgt     600
cagccgcgcc tgtttgatta tctgtttacc caccgtaaca acacaaaact gatggcgctg     660
attgatgttc gcagatgaa accgctggtg catgtgagcg catgtttgg cgcctggcgc     720
ggcaacacca gctgggtggc cccgctggcc tggcacccgg aaaatcgtaa cgccgtgatt     780
atggttgatc tggccggtga tattagcccg ctgctggaac tggatagcga taccctgcgt     840
gaacgcctgt ataccgccaa accgatctgg gcgataatg ccgccgtgcc ggtgaaactg     900
gttcacatta caaatgccc ggtgctggcc caggcgaaca ccctgcgccc ggaagatgcg     960
gatcgtctgg gtattaatcg ccagcattgt ctggataatc tgaaaatcct gcgtgaaaac    1020
ccgcaggtgc gtgaaaaagt ggtggcgatc ttcgcggaag cggaaccgtt caccccgagc    1080
gataacgtgg atgcgcagct gtataacggc ttctttagcg atgccgatcg cgcggcgatg    1140
aaaatcgttc tggaaaccga accgcgcaat ctgccggcgc tggatattac ctttgttgat    1200
aaacgtattg aaaaactgct gtttaattat cgtgcgcgca attttccggg taccctggat    1260
tatgccgaac agcagcgttg gctggaacat cgtcgtcagg ttttcacccc ggaatttctg    1320
cagggttatg cggatgaact gcagatgctg gttcagcagt atgccgatga taaagaaaaa    1380
gtggcgctgc                                                          1390
```

<210> SEQ ID NO 11
<211> LENGTH: 485
<212> TYPE: PRT

<213> ORGANISM: Escherichia coli

<400> SEQUENCE: 11

```
Met Met Asn Asp Gly Lys Gln Gln Ser Thr Phe Leu Phe His Asp Tyr
 1               5                  10                  15
Glu Thr Phe Gly Thr His Pro Ala Leu Asp Arg Pro Ala Gln Phe Ala
            20                  25                  30
Ala Ile Arg Thr Asp Ser Glu Phe Asn Val Ile Gly Glu Pro Glu Val
        35                  40                  45
Phe Tyr Cys Lys Pro Ala Asp Asp Tyr Leu Pro Gln Pro Gly Ala Val
    50                  55                  60
Leu Ile Thr Gly Ile Thr Pro Gln Glu Ala Arg Ala Lys Gly Glu Asn
65                  70                  75                  80
Glu Ala Ala Phe Ala Ala Arg Ile His Ser Leu Phe Thr Val Pro Lys
                85                  90                  95
Thr Cys Ile Leu Gly Tyr Asn Asn Val Arg Phe Asp Asp Glu Val Thr
            100                 105                 110
Arg Asn Ile Phe Tyr Arg Asn Phe Tyr Asp Pro Tyr Ala Trp Ser Trp
        115                 120                 125
Gln His Asp Asn Ser Arg Trp Asp Leu Leu Asp Val Met Arg Ala Cys
    130                 135                 140
Tyr Ala Leu Arg Pro Glu Gly Ile Asn Trp Pro Glu Asn Asp Asp Gly
145                 150                 155                 160
Leu Pro Ser Phe Arg Leu Glu His Leu Thr Lys Ala Asn Gly Ile Glu
                165                 170                 175
His Ser Asn Ala His Asp Ala Met Ala Asp Val Tyr Ala Thr Ile Ala
            180                 185                 190
Met Ala Lys Leu Val Lys Thr Arg Gln Pro Arg Leu Phe Asp Tyr Leu
        195                 200                 205
Phe Thr His Arg Asn Lys His Lys Leu Met Ala Leu Ile Asp Val Pro
    210                 215                 220
Gln Met Lys Pro Leu Val His Val Ser Gly Met Phe Gly Ala Trp Arg
225                 230                 235                 240
Gly Asn Thr Ser Trp Val Ala Pro Leu Ala Trp His Pro Glu Asn Arg
                245                 250                 255
Asn Ala Val Ile Met Val Asp Leu Ala Gly Asp Ile Ser Pro Leu Leu
            260                 265                 270
Glu Leu Asp Ser Asp Thr Leu Arg Glu Arg Leu Tyr Thr Ala Lys Thr
        275                 280                 285
Asp Leu Gly Asp Asn Ala Ala Val Pro Val Lys Leu Val His Ile Asn
    290                 295                 300
Lys Cys Pro Val Leu Ala Gln Ala Asn Thr Leu Arg Pro Glu Asp Ala
305                 310                 315                 320
Asp Arg Leu Gly Ile Asn Arg Gln His Cys Leu Asp Asn Leu Lys Ile
                325                 330                 335
Leu Arg Glu Asn Pro Gln Val Arg Glu Lys Val Val Ala Ile Phe Ala
            340                 345                 350
Glu Ala Glu Pro Phe Thr Pro Ser Asp Asn Val Asp Ala Gln Leu Tyr
        355                 360                 365
Asn Gly Phe Phe Ser Asp Ala Asp Arg Ala Ala Met Lys Ile Val Leu
    370                 375                 380
Glu Thr Glu Pro Arg Asn Leu Pro Ala Leu Asp Ile Thr Phe Val Asp
385                 390                 395                 400
```

Lys Arg Ile Glu Lys Leu Leu Phe Asn Tyr Arg Ala Arg Asn Phe Pro
            405                 410                 415

Gly Thr Leu Asp Tyr Ala Glu Gln Gln Arg Trp Leu Glu His Arg Arg
        420                 425                 430

Gln Val Phe Thr Pro Glu Phe Leu Gln Gly Tyr Ala Asp Glu Leu Gln
            435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Ser Gly His
465                 470                 475                 480

His His His His His
            485

<210> SEQ ID NO 12
<211> LENGTH: 804
<212> TYPE: DNA
<213> ORGANISM: Escherichia coli

<400> SEQUENCE: 12
atgaaatttg tctcttttaa tatcaacggc ctgcgcgcca gacctcacca gcttgaagcc        60
atcgtcgaaa agcaccaacc ggatgtgatt ggcctgcagg agacaaaagt tcatgacgat       120
atgtttccgc tcgaagaggt ggcgaagctc ggctacaacg tgttttatca cgggcagaaa       180
ggccattatg gcgtggcgct gctgaccaaa gagacgccga ttgccgtgcg tcgcggcttt       240
cccggtgacg acgaagaggc gcagcggcgg attattatgg cggaaatccc ctcactgctg       300
ggtaatgtca ccgtgatcaa cggttacttc ccgcagggtg aaagccgcga ccatccgata       360
aaattcccgg caaaagcgca gttttatcag aatctgcaaa actacctgga aaccgaactc       420
aaacgtgata atccggtact gattatgggc gatatgaata tcagccctac agatctggat       480
atcggcattg gcgaagaaaa ccgtaagcgc tggctgcgta ccggtaaatg ctctttcctg       540
ccggaagagc gcgaatggat ggacaggctg atgagctggg ggttggtcga taccttccgc       600
catgcgaatc cgcaaacagc agatcgtttc tcatggtttg attaccgctc aaaaggtttt       660
gacgataacc gtggtctgcg catcgacctg ctgctcgcca gccaaccgct ggcagaatgt       720
tgcgtagaaa ccggcatcga ctatgaaatc cgcagcatgg aaaaaccgtc cgatcacgcc       780
cccgtctggg cgaccttccg ccgc                                              804

<210> SEQ ID NO 13
<211> LENGTH: 268
<212> TYPE: PRT
<213> ORGANISM: Escherichia coli

<400> SEQUENCE: 13

Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
            85                  90                  95

```
Pro Ser Leu Leu Gly Asn Val Thr Val Ile Asn Gly Tyr Phe Pro Gln
            100                 105                 110
Gly Glu Ser Arg Asp His Pro Ile Lys Phe Pro Ala Lys Ala Gln Phe
                115                 120                 125
Tyr Gln Asn Leu Gln Asn Tyr Leu Glu Thr Glu Leu Lys Arg Asp Asn
            130                 135                 140
Pro Val Leu Ile Met Gly Asp Met Asn Ile Ser Pro Thr Asp Leu Asp
145                 150                 155                 160
Ile Gly Ile Gly Glu Glu Asn Arg Lys Arg Trp Leu Arg Thr Gly Lys
                165                 170                 175
Cys Ser Phe Leu Pro Glu Glu Arg Glu Trp Met Asp Arg Leu Met Ser
            180                 185                 190
Trp Gly Leu Val Asp Thr Phe Arg His Ala Asn Pro Gln Thr Ala Asp
                195                 200                 205
Arg Phe Ser Trp Phe Asp Tyr Arg Ser Lys Gly Phe Asp Asp Asn Arg
        210                 215                 220
Gly Leu Arg Ile Asp Leu Leu Ala Ser Gln Pro Leu Ala Glu Cys
225                 230                 235                 240
Cys Val Glu Thr Gly Ile Asp Tyr Glu Ile Arg Ser Met Glu Lys Pro
                245                 250                 255
Ser Asp His Ala Pro Val Trp Ala Thr Phe Arg Arg
            260                 265
```

<210> SEQ ID NO 14
<211> LENGTH: 1275
<212> TYPE: DNA
<213> ORGANISM: Thermus thermophilus

<400> SEQUENCE: 14

```
atgtttcgtc gtaaagaaga tctggatccg ccgctggcac tgctgccgct gaaaggcctg      60
cgcgaagccg ccgcactgct ggaagaagcg ctgcgtcaag gtaaacgcat cgtgttcac      120
ggcgactatg atgcggatgg cctgaccggc accgcgatcc tggttcgtgg tctggccgcc     180
ctgggtgcgg atgttcatcc gtttatcccg caccgcctgg aagaaggcta tggtgtcctg     240
atggaacgcg tcccggaaca tctggaagcc tcggacctgt ttctgaccgt tgactgcggc     300
attaccaacc atgcggaact gcgcgaactg ctggaaaatg gcgtggaagt cattgttacc     360
gatcatcata cgccgggcaa aacgccgccg ccgggtctgg tcgtgcatcc ggcgctgacg     420
ccggatctga agaaaaaacc gaccggcgca ggcgtggcgt ttctgctgct gtgggcactg     480
catgaacgcc tgggcctgcc gccgccgctg aatacgcgg acctggcagc cgttggcacc      540
attgccgacg ttgccccgct gtggggttgg aatcgtgcac tggtgaaaga aggtctggca     600
cgcatcccgg cttcatcttg ggtgggcctg cgtctgctgg ctgaagccgt gggctatacc     660
ggcaaagcgg tcgaagtcgc tttccgcatc gcgccgcgca tcaatgcggc ttcccgcctg     720
ggcgaagcgg aaaaagccct cgcgctgctg ctgacggatg atgcggcaga agctcaggcg     780
ctggtcggcg aactgcaccg tctgaacgcc gtcgtcaga ccctggaaga agcgatgctg      840
cgcaaactgc tgccgcaggc cgacccggaa gcgaaagcca tcgttctgct ggacccggaa     900
ggccatccgg tgttatggg tattgtggcc tctcgcatcc tggaagcgac cctgcgcccg      960
gtctttctgg tggcccaggg caaaggcacc gtgcgttcgc tggctccgat tccgccgtc     1020
gaagcactgc gcagcgcgga agatctgctg ctgcgttatg tggtcataa agaagcggcg    1080
ggtttcgcaa tggatgaagc gctgtttccg gcgttcaaag cacgcgttga agcgtatgcc    1140
```

```
gcacgtttcc cggatccggt tcgtgaagtg gcactgctgg atctgctgcc ggaaccgggc    1200
ctgctgccgc aggtgttccg tgaactggca ctgctggaac cgtatggtga aggtaacccg    1260
gaaccgctgt tcctg                                                     1275
```

<210> SEQ ID NO 15
<211> LENGTH: 425
<212> TYPE: PRT
<213> ORGANISM: Thermus thermophilus

<400> SEQUENCE: 15

```
Met Phe Arg Arg Lys Glu Asp Leu Asp Pro Pro Leu Ala Leu Leu Pro
1               5                   10                  15

Leu Lys Gly Leu Arg Glu Ala Ala Leu Leu Glu Glu Ala Leu Arg
            20                  25                  30

Gln Gly Lys Arg Ile Arg Val His Gly Asp Tyr Asp Ala Asp Gly Leu
        35                  40                  45

Thr Gly Thr Ala Ile Leu Val Arg Gly Leu Ala Ala Leu Gly Ala Asp
    50                  55                  60

Val His Pro Phe Ile Pro His Arg Leu Glu Glu Gly Tyr Gly Val Leu
65                  70                  75                  80

Met Glu Arg Val Pro Glu His Leu Glu Ala Ser Asp Leu Phe Leu Thr
                85                  90                  95

Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
        115                 120                 125

Pro Pro Pro Gly Leu Val Val His Pro Ala Leu Thr Pro Asp Leu Lys
    130                 135                 140

Glu Lys Pro Thr Gly Ala Gly Val Ala Phe Leu Leu Leu Trp Ala Leu
145                 150                 155                 160

His Glu Arg Leu Gly Leu Pro Pro Leu Glu Tyr Ala Asp Leu Ala
                165                 170                 175

Ala Val Gly Thr Ile Ala Asp Val Ala Pro Leu Trp Gly Trp Asn Arg
            180                 185                 190

Ala Leu Val Lys Glu Gly Leu Ala Arg Ile Pro Ala Ser Ser Trp Val
        195                 200                 205

Gly Leu Arg Leu Leu Ala Glu Ala Val Gly Tyr Thr Gly Lys Ala Val
    210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Thr Asp Asp Ala Ala
                245                 250                 255

Glu Ala Gln Ala Leu Val Gly Glu Leu His Arg Leu Asn Ala Arg Arg
            260                 265                 270

Gln Thr Leu Glu Glu Ala Met Leu Arg Lys Leu Leu Pro Gln Ala Asp
        275                 280                 285

Pro Glu Ala Lys Ala Ile Val Leu Leu Asp Pro Glu Gly His Pro Gly
    290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
```

```
                340             345             350
Tyr Gly Gly His Lys Glu Ala Ala Gly Phe Ala Met Asp Glu Ala Leu
            355                 360                 365

Phe Pro Ala Phe Lys Ala Arg Val Glu Ala Tyr Ala Ala Arg Phe Pro
        370                 375                 380

Asp Pro Val Arg Glu Val Ala Leu Leu Asp Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
            420                 425

<210> SEQ ID NO 16
<211> LENGTH: 738
<212> TYPE: DNA
<213> ORGANISM: Bacteriophage lambda

<400> SEQUENCE: 16
tccggaagcg gctctggtag tggttctggc atgacaccgg acattatcct gcagcgtacc      60
gggatcgatg tgagagctgt cgaacagggg gatgatgcgt ggcacaaatt acggctcggc    120
gtcatcaccg cttcagaagt tcacaacgtg atagcaaaac cccgctccgg aaagaagtgg    180
cctgacatga aaatgtccta cttccacacc ctgcttgctg aggtttgcac cggtgtggct    240
ccggaagtta acgctaaagc actggcctgg ggaaaacagt acgagaacga cgccagaacc    300
ctgtttgaat tcacttccgg cgtgaatgtt actgaatccc cgatcatcta tcgcgacgaa    360
agtatgcgta ccgcctgctc tcccgatggt ttatgcagtg acggcaacgg ccttgaactg    420
aaatgcccgt ttacctcccg ggatttcatg aagttccggc tcggtggttt cgaggccata    480
aagtcagctt acatggccca ggtgcagtac agcatgtggg tgacgcgaaa aaatgcctgg    540
tactttgcca actatgaccc gcgtatgaag cgtgaaggcc tgcattatgt cgtgattgag    600
cgggatgaaa agtacatggc gagttttgac gagatcgtgc cggagttcat cgaaaaaatg    660
gacgaggcac tggctgaaat tggttttgta tttggggagc aatggcgatc tggctctggt    720
tccggcagcg gttccgga                                                 738

<210> SEQ ID NO 17
<211> LENGTH: 226
<212> TYPE: PRT
<213> ORGANISM: Bacteriophage lambda

<400> SEQUENCE: 17

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
                20                  25                  30

Thr Ala Ser Glu Val His Asn Val Ile Ala Lys Pro Arg Ser Gly Lys
            35                  40                  45

Lys Trp Pro Asp Met Lys Met Ser Tyr Phe His Thr Leu Leu Ala Glu
        50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110
```

```
Arg Thr Ala Cys Ser Pro Asp Gly Leu Cys Ser Asp Gly Asn Gly Leu
            115                 120                 125

Glu Leu Lys Cys Pro Phe Thr Ser Arg Asp Phe Met Lys Phe Arg Leu
        130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
                180                 185                 190

Glu Lys Tyr Met Ala Ser Phe Asp Glu Ile Val Pro Glu Phe Ile Glu
            195                 200                 205

Lys Met Asp Glu Ala Leu Ala Glu Ile Gly Phe Val Phe Gly Glu Gln
        210                 215                 220

Trp Arg
225

<210> SEQ ID NO 18
<211> LENGTH: 760
<212> TYPE: PRT
<213> ORGANISM: Methanococcoides burtonii

<400> SEQUENCE: 18

Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
        115                 120                 125

Arg Asn Gly Thr Ser Trp Met Asp Glu Ile Thr Thr Val Val Val Asp
    130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
        195                 200                 205

Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
```

```
                245                 250                 255
Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser
            275                 280                 285

Thr Gly Glu Thr Asp Thr Ala Ile Val Leu Ala Asn Cys Ile Arg Lys
        290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Arg Arg Phe Asp Ser Asn Phe Gly Met Gln Pro Ile Pro
            355                 360                 365

Val Leu Glu Tyr Lys Gln Met Ala Gly Arg Ala Gly Arg Pro His Leu
        370                 375                 380

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415

Ser Lys Leu Gly Thr Glu Asn Ala Leu Arg Thr His Val Leu Ser Thr
            420                 425                 430

Ile Val Asn Gly Phe Ala Ser Thr Arg Gln Glu Leu Phe Asp Phe Phe
            435                 440                 445

Gly Ala Thr Phe Phe Ala Tyr Gln Gln Asp Lys Trp Met Leu Glu Glu
        450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
            500                 505                 510

Ser Lys Ile Val Asp Gly Phe Lys Asp Ile Gly Lys Ser Thr Gly Gly
            515                 520                 525

Asn Met Gly Ser Leu Glu Asp Asp Lys Gly Asp Asp Ile Thr Val Thr
        530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
            580                 585                 590

Asp Tyr Glu Trp Phe Met Gly Glu Val Lys Thr Ala Met Leu Leu Glu
            595                 600                 605

Glu Trp Val Thr Glu Val Ser Ala Glu Asp Ile Thr Arg His Phe Asn
        610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
            660                 665                 670
```

```
Asp Leu Met Glu Leu Val Gly Ile Arg Gly Val Gly Arg Val Arg Ala
            675                 680                 685

Arg Lys Leu Tyr Asn Ala Gly Phe Val Ser Val Ala Lys Leu Lys Gly
        690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
            740                 745                 750

Gln Lys Thr Phe Asn Asp Phe Gln
        755                 760

<210> SEQ ID NO 19
<211> LENGTH: 707
<212> TYPE: PRT
<213> ORGANISM: Cenarchaeum symbiosum

<400> SEQUENCE: 19

Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
            20                  25                  30

Lys Ala Gly Leu Thr Asp Gly Lys Ser Val Leu Val Ser Ala Pro Thr
        35                  40                  45

Ala Ser Gly Lys Thr Leu Ile Ala Ala Ile Ala Met Ile Ser His Leu
    50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Ile Gly Ile Pro Leu
                85                  90                  95

Gly Arg Pro Val Arg Val Gly Val Ser Thr Gly Asp Phe Glu Lys Ala
            100                 105                 110

Gly Arg Ser Leu Gly Asn Asn Asp Ile Leu Val Leu Thr Asn Glu Arg
        115                 120                 125

Met Asp Ser Leu Ile Arg Arg Pro Asp Trp Met Asp Glu Val Gly
130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
            180                 185                 190

Ala Gly Trp Leu Asp Cys Thr Leu Val His Ser Thr Trp Arg Pro Val
        195                 200                 205

Pro Leu Ser Glu Gly Val Tyr Gln Asp Gly Glu Val Ala Met Gly Asp
    210                 215                 220

Gly Ser Arg His Glu Val Ala Ala Thr Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
            260                 265                 270

Ile Pro Glu Ala Lys Gly Ala Asp Ala Ala Lys Leu Ala Ala Ala Ala
```

```
            275                 280                 285
Lys Lys Ile Ile Ser Ser Gly Gly Glu Thr Lys Leu Ala Lys Thr Leu
            290                 295                 300
Ala Glu Leu Val Glu Lys Gly Ala Ala Phe His His Ala Gly Leu Asn
305                 310                 315                 320
Gln Asp Cys Arg Ser Val Val Glu Glu Phe Arg Ser Gly Arg Ile
                    325                 330                 335
Arg Leu Leu Ala Ser Thr Pro Thr Leu Ala Ala Gly Val Asn Leu Pro
                    340                 345                 350
Ala Arg Arg Val Val Ile Ser Ser Val Met Arg Tyr Asn Ser Ser Ser
                    355                 360                 365
Gly Met Ser Glu Pro Ile Ser Ile Leu Glu Tyr Lys Gln Leu Cys Gly
                    370                 375                 380
Arg Ala Gly Arg Pro Gln Tyr Asp Lys Ser Gly Glu Ala Ile Val Val
385                 390                 395                 400
Gly Gly Val Asn Ala Asp Glu Ile Phe Asp Arg Tyr Ile Gly Gly Glu
                    405                 410                 415
Pro Glu Pro Ile Arg Ser Ala Met Val Asp Asp Arg Ala Leu Arg Ile
                    420                 425                 430
His Val Leu Ser Leu Val Thr Thr Ser Pro Gly Ile Lys Glu Asp Asp
                    435                 440                 445
Val Thr Glu Phe Phe Leu Gly Thr Leu Gly Gly Gln Gln Ser Gly Glu
                    450                 455                 460
Ser Thr Val Lys Phe Ser Val Ala Val Ala Leu Arg Phe Leu Gln Glu
465                 470                 475                 480
Glu Gly Met Leu Gly Arg Arg Gly Gly Arg Leu Ala Ala Thr Lys Met
                    485                 490                 495
Gly Arg Leu Val Ser Arg Leu Tyr Met Asp Pro Met Thr Ala Val Thr
                    500                 505                 510
Leu Arg Asp Ala Val Gly Glu Ala Ser Pro Gly Arg Met His Thr Leu
                    515                 520                 525
Gly Phe Leu His Leu Val Ser Glu Cys Ser Glu Phe Met Pro Arg Phe
                    530                 535                 540
Ala Leu Arg Gln Lys Asp His Glu Val Ala Glu Met Met Leu Glu Ala
545                 550                 555                 560
Gly Arg Gly Glu Leu Leu Arg Pro Val Tyr Ser Tyr Glu Cys Gly Arg
                    565                 570                 575
Gly Leu Leu Ala Leu His Arg Trp Ile Gly Glu Ser Pro Glu Ala Lys
                    580                 585                 590
Leu Ala Glu Asp Leu Lys Phe Glu Ser Gly Asp Val His Arg Met Val
                    595                 600                 605
Glu Ser Ser Gly Trp Leu Leu Arg Cys Ile Trp Glu Ile Ser Lys His
                    610                 615                 620
Gln Glu Arg Pro Asp Leu Leu Gly Glu Leu Asp Val Leu Arg Ser Arg
625                 630                 635                 640
Val Ala Tyr Gly Ile Lys Ala Glu Leu Val Pro Leu Val Ser Ile Lys
                    645                 650                 655
Gly Ile Gly Arg Val Arg Ser Arg Arg Leu Phe Arg Gly Gly Ile Lys
                    660                 665                 670
Gly Pro Gly Asp Leu Ala Ala Val Pro Val Glu Arg Leu Ser Arg Val
                    675                 680                 685
Glu Gly Ile Gly Ala Thr Leu Ala Asn Asn Ile Lys Ser Gln Leu Arg
                    690                 695                 700
```

Lys Gly Gly
705

<210> SEQ ID NO 20
<211> LENGTH: 720
<212> TYPE: PRT
<213> ORGANISM: Thermococcus gammatolerans EJ3

<400> SEQUENCE: 20

Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
            20                  25                  30

Lys Ser Gly Ala Leu Glu Gly Arg Asn Leu Val Leu Ala Ile Pro Thr
        35                  40                  45

Ala Ser Gly Lys Thr Leu Val Ser Glu Ile Val Met Val Asn Lys Leu
    50                  55                  60

Ile Gln Glu Gly Gly Lys Ala Val Tyr Leu Val Pro Leu Lys Ala Leu
65                  70                  75                  80

Ala Glu Glu Lys Tyr Arg Glu Phe Lys Glu Trp Glu Lys Leu Gly Leu
                85                  90                  95

Lys Val Ala Ala Thr Thr Gly Asp Tyr Asp Ser Thr Asp Asp Trp Leu
            100                 105                 110

Gly Arg Tyr Asp Ile Ile Val Ala Thr Ala Glu Lys Phe Asp Ser Leu
        115                 120                 125

Leu Arg His Gly Ala Arg Trp Ile Asn Asp Val Lys Leu Val Val Ala
    130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
                165                 170                 175

Ala Thr Val Gly Asn Ala Glu Glu Leu Ala Glu Trp Leu Asp Ala Ser
            180                 185                 190

Leu Val Val Ser Asp Trp Arg Pro Val Gln Leu Arg Arg Gly Val Phe
        195                 200                 205

His Leu Gly Thr Leu Ile Trp Glu Asp Gly Lys Val Glu Ser Tyr Pro
    210                 215                 220

Glu Asn Trp Tyr Ser Leu Val Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
            260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Gly Val Ala Phe His His Ala Gly
    290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Ile Arg Asp Thr Lys Tyr Ala Gly
            340                 345                 350

Phe Gly Trp Thr Asp Ile Pro Val Leu Glu Ile Gln Gln Met Met Gly

```
                355                 360                 365
Arg Ala Gly Arg Pro Arg Tyr Asp Lys Tyr Gly Glu Ala Ile Ile Val
370                 375                 380

Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
                405                 410                 415

Ser Gln Val Leu Ala Leu Ile Thr Asn Phe Gly Ile Arg Ser Phe Pro
                420                 425                 430

Glu Leu Val Arg Phe Leu Glu Arg Thr Phe Tyr Ala His Gln Arg Lys
                435                 440                 445

Asp Leu Ser Ser Leu Glu Tyr Lys Ala Lys Glu Val Val Tyr Phe Leu
                450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
                485                 490                 495

Ala Lys Lys Phe Lys Asp Ala Phe Pro Ala Ile Glu Arg Asn Pro Asn
                500                 505                 510

Pro Phe Gly Ile Phe Gln Leu Ile Ala Ser Thr Pro Asp Met Ala Thr
                515                 520                 525

Leu Thr Ala Arg Arg Glu Met Glu Asp Tyr Leu Asp Leu Ala Tyr
530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
                580                 585                 590

Ile Asp Pro Gly Asp Leu Tyr Arg Leu Leu Glu Leu Ala Asp Trp Leu
                595                 600                 605

Met Tyr Ser Leu Ile Glu Leu Tyr Lys Leu Phe Glu Pro Lys Glu Glu
                610                 615                 620

Ile Leu Asn Tyr Leu Arg Asp Leu His Leu Arg Leu Arg His Gly Val
625                 630                 635                 640

Arg Glu Glu Leu Leu Glu Leu Val Arg Leu Pro Asn Ile Gly Arg Lys
                645                 650                 655

Arg Ala Arg Ala Leu Tyr Asn Ala Gly Phe Arg Ser Val Glu Ala Ile
                660                 665                 670

Ala Asn Ala Lys Pro Ala Glu Leu Leu Ala Val Glu Gly Ile Gly Ala
                675                 680                 685

Lys Ile Leu Asp Gly Ile Tyr Arg His Leu Gly Ile Glu Lys Arg Val
                690                 695                 700

Thr Glu Glu Lys Pro Lys Arg Lys Gly Thr Leu Glu Asp Phe Leu Arg
705                 710                 715                 720
```

<210> SEQ ID NO 21
<211> LENGTH: 799
<212> TYPE: PRT
<213> ORGANISM: Methanospirillum hungatei JF-1

<400> SEQUENCE: 21

```
Met Glu Ile Ala Ser Leu Pro Leu Pro Asp Ser Phe Ile Arg Ala Cys
1               5                   10                  15
```

```
His Ala Lys Gly Ile Arg Ser Leu Tyr Pro Pro Gln Ala Glu Cys Ile
             20                  25                  30

Glu Lys Gly Leu Leu Glu Gly Lys Asn Leu Leu Ile Ser Ile Pro Thr
         35                  40                  45

Ala Ser Gly Lys Thr Leu Leu Ala Glu Met Ala Met Trp Ser Arg Ile
     50                  55                  60

Ala Ala Gly Gly Lys Cys Leu Tyr Ile Val Pro Leu Arg Ala Leu Ala
 65                  70                  75                  80

Ser Glu Lys Tyr Asp Glu Phe Ser Lys Lys Gly Val Ile Arg Val Gly
                 85                  90                  95

Ile Ala Thr Gly Asp Leu Asp Arg Thr Asp Ala Tyr Leu Gly Glu Asn
             100                 105                 110

Asp Ile Ile Val Ala Thr Ser Glu Lys Thr Asp Ser Leu Leu Arg Asn
             115                 120                 125

Arg Thr Pro Trp Leu Ser Gln Ile Thr Cys Ile Val Leu Asp Glu Val
         130                 135                 140

His Leu Ile Gly Ser Glu Asn Arg Gly Ala Thr Leu Glu Met Val Ile
145                 150                 155                 160

Thr Lys Leu Arg Tyr Thr Asn Pro Val Met Gln Ile Ile Gly Leu Ser
                 165                 170                 175

Ala Thr Ile Gly Asn Pro Ala Gln Leu Ala Glu Trp Leu Asp Ala Thr
             180                 185                 190

Leu Ile Thr Ser Thr Trp Arg Pro Val Asp Leu Arg Gln Gly Val Tyr
         195                 200                 205

Tyr Asn Gly Lys Ile Arg Phe Ser Asp Ser Glu Arg Pro Ile Gln Gly
     210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Ser Arg Arg Asn Ala Glu Gly
                 245                 250                 255

Phe Ala Lys Lys Ala Ala Gly Ala Leu Lys Ala Gly Ser Pro Asp Ser
             260                 265                 270

Lys Ala Leu Ala Gln Glu Leu Arg Arg Leu Arg Asp Arg Asp Glu Gly
         275                 280                 285

Asn Val Leu Ala Asp Cys Val Glu Arg Gly Ala Ala Phe His His Ala
     290                 295                 300

Gly Leu Ile Arg Gln Glu Arg Thr Ile Ile Glu Glu Gly Phe Arg Asn
305                 310                 315                 320

Gly Tyr Ile Glu Val Ile Ala Ala Thr Pro Thr Leu Ala Ala Gly Leu
                 325                 330                 335

Asn Leu Pro Ala Arg Arg Val Ile Ile Arg Asp Tyr Asn Arg Phe Ala
             340                 345                 350

Ser Gly Leu Gly Met Val Pro Ile Pro Val Gly Glu Tyr His Gln Met
         355                 360                 365

Ala Gly Arg Ala Gly Arg Pro His Leu Asp Pro Tyr Gly Glu Ala Val
     370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
                 405                 410                 415

Ser Leu Cys Ala His Ile Leu Ser Leu Ile Ala Thr Gly Phe Ala His
             420                 425                 430

Asp Gln Glu Ala Leu Ser Ser Phe Met Glu Arg Thr Phe Tyr Phe Phe
```

```
                    435                 440                 445
Gln His Pro Lys Thr Arg Ser Leu Pro Arg Leu Val Ala Asp Ala Ile
450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
                485                 490                 495

Cys Thr Ala Arg Leu Ile Leu Asp Ser Leu Lys Ser Cys Lys Thr Pro
                500                 505                 510

Thr Leu Ile Gly Leu Leu His Val Ile Cys Val Ser Pro Asp Met Gln
515                 520                 525

Arg Leu Tyr Leu Lys Ala Ala Asp Thr Gln Leu Leu Arg Thr Phe Leu
530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr
                565                 570                 575

Asp Trp Ala Asp Glu Phe Ser Glu Gly Met Ile Glu Glu Arg Tyr Gly
                580                 585                 590

Ile Gly Ala Gly Asp Leu Tyr Asn Ile Val Asp Ser Gly Lys Trp Leu
                595                 600                 605

Leu His Gly Thr Glu Arg Leu Val Ser Val Glu Met Pro Glu Met Ser
610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
                660                 665                 670

Ala Gly Leu Ser Thr Ile Ala Arg Ile Ile Gly Glu Gly Ile Ala Arg
                675                 680                 685

Gln Val Ile Asp Glu Ile Thr Gly Val Lys Arg Ser Gly Ile His Ser
690                 695                 700

Ser Asp Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
                725                 730                 735

Ile Thr Val Ser Asp Leu Leu Thr Ala Asp Glu Val Leu Leu Ser Asp
                740                 745                 750

Val Leu Gly Ala Ala Arg Ala Arg Lys Val Leu Ala Phe Leu Ser Asn
                755                 760                 765

Ser Glu Lys Glu Asn Ser Ser Asp Lys Thr Glu Glu Ile Pro Asp
770                 775                 780

Thr Gln Lys Ile Arg Gly Gln Ser Ser Trp Glu Asp Phe Gly Cys
785                 790                 795

<210> SEQ ID NO 22
<211> LENGTH: 1756
<212> TYPE: PRT
<213> ORGANISM: Escherichia coli

<400> SEQUENCE: 22

Met Met Ser Ile Ala Gln Val Arg Ser Ala Gly Ser Ala Gly Asn Tyr
1               5                   10                  15
```

```
Tyr Thr Asp Lys Asp Asn Tyr Tyr Val Leu Gly Ser Met Gly Glu Arg
            20                  25                  30

Trp Ala Gly Lys Gly Ala Glu Gln Leu Gly Leu Gln Gly Ser Val Asp
        35                  40                  45

Lys Asp Val Phe Thr Arg Leu Leu Glu Gly Arg Leu Pro Asp Gly Ala
50                  55                  60

Asp Leu Ser Arg Met Gln Asp Gly Ser Asn Lys His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
        115                 120                 125

Gly Gln Ser Glu Thr Val Leu Thr Gly Asn Leu Val Met Ala Leu Phe
    130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
        195                 200                 205

Glu Ala Leu Gly Tyr Glu Thr Glu Val Val Gly Lys His Gly Met Trp
    210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
                245                 250                 255

Ala Ala Leu Asp Thr Arg Lys Ser Lys Gln His Val Asp Pro Glu Ile
            260                 265                 270

Arg Met Ala Glu Trp Met Gln Thr Leu Lys Glu Thr Gly Phe Asp Ile
        275                 280                 285

Arg Ala Tyr Arg Asp Ala Ala Asp Gln Arg Thr Glu Ile Arg Thr Gln
    290                 295                 300

Ala Pro Gly Pro Ala Ser Gln Asp Gly Pro Asp Val Gln Gln Ala Val
305                 310                 315                 320

Thr Gln Ala Ile Ala Gly Leu Ser Glu Arg Lys Val Gln Phe Thr Tyr
                325                 330                 335

Thr Asp Val Leu Ala Arg Thr Val Gly Ile Leu Pro Pro Glu Asn Gly
            340                 345                 350

Val Ile Glu Arg Ala Arg Ala Gly Ile Asp Glu Ala Ile Ser Arg Glu
        355                 360                 365

Gln Leu Ile Pro Leu Asp Arg Glu Lys Gly Leu Phe Thr Ser Gly Ile
    370                 375                 380

His Val Leu Asp Glu Leu Ser Val Arg Ala Leu Ser Arg Asp Ile Met
385                 390                 395                 400

Lys Gln Asn Arg Val Thr His Pro Glu Lys Ser Val Pro Arg Thr
                405                 410                 415

Ala Gly Tyr Ser Asp Ala Val Ser Val Leu Ala Gln Asp Arg Pro Ser
            420                 425                 430

Leu Ala Ile Val Ser Gly Gln Gly Gly Ala Ala Gly Gln Arg Glu Arg
```

```
            435                 440                 445
Val Ala Glu Leu Val Met Met Ala Arg Glu Gln Gly Arg Glu Val Gln
450                 455                 460

Ile Ile Ala Ala Asp Arg Arg Ser Gln Met Asn Leu Lys Gln Asp Glu
465                 470                 475                 480

Arg Leu Ser Gly Glu Leu Ile Thr Gly Arg Gln Leu Leu Glu Gly
                485                 490                 495

Met Ala Phe Thr Pro Gly Ser Thr Val Ile Val Asp Gln Gly Glu Lys
                500                 505                 510

Leu Ser Leu Lys Glu Thr Leu Thr Leu Leu Asp Gly Ala Arg His
                515                 520                 525

Asn Val Gln Val Leu Ile Thr Asp Ser Gly Gln Arg Thr Gly Thr Gly
530                 535                 540

Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
                565                 570                 575

Asn Val Arg Tyr Ala Arg Leu Ala Gly Asp Phe Ala Ala Ser Val Lys
                580                 585                 590

Ala Gly Glu Glu Ser Val Ala Gln Val Ser Gly Val Arg Glu Gln Ala
                595                 600                 605

Ile Leu Thr Gln Ala Ile Arg Ser Glu Leu Lys Thr Gln Gly Val Leu
610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
                645                 650                 655

Glu Gln Trp Asn Pro Glu Thr Arg Ser His Asp Arg Tyr Val Ile Asp
                660                 665                 670

Arg Val Thr Ala Gln Ser His Ser Leu Thr Leu Arg Asp Ala Gln Gly
                675                 680                 685

Glu Thr Gln Val Val Arg Ile Ser Ser Leu Asp Ser Ser Trp Ser Leu
690                 695                 700

Phe Arg Pro Glu Lys Met Pro Val Ala Asp Gly Glu Arg Leu Arg Val
705                 710                 715                 720

Thr Gly Lys Ile Pro Gly Leu Arg Val Ser Gly Gly Asp Arg Leu Gln
                725                 730                 735

Val Ala Ser Val Ser Glu Asp Ala Met Thr Val Val Pro Gly Arg
                740                 745                 750

Ala Glu Pro Ala Ser Leu Pro Val Ser Asp Ser Pro Phe Thr Ala Leu
                755                 760                 765

Lys Leu Glu Asn Gly Trp Val Glu Thr Pro Gly His Ser Val Ser Asp
                770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
                805                 810                 815

Ser Leu Asp Glu Thr Arg Thr Ala Glu Lys Leu Ala Arg His Pro Ser
                820                 825                 830

Phe Thr Val Val Ser Glu Gln Ile Lys Ala Arg Ala Gly Glu Thr Leu
                835                 840                 845

Leu Glu Thr Ala Ile Ser Leu Gln Lys Ala Gly Leu His Thr Pro Ala
850                 855                 860
```

-continued

```
Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
            900                 905                 910

Lys Arg Gly Asp Leu Leu Tyr Val Asp Val Ala Lys Gly Tyr Gly Thr
        915                 920                 925

Gly Leu Leu Val Ser Arg Ala Ser Tyr Glu Ala Glu Lys Ser Ile Leu
    930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
                965                 970                 975

Thr Arg Met Ile Leu Glu Thr Ser Asp Arg Phe Thr Val Val Gln Gly
            980                 985                 990

Tyr Ala Gly Val Gly Lys Thr Thr Gln Phe Arg Ala Val Met Ser Ala
        995                 1000                1005

Val Asn Met Leu Pro Ala Ser Glu Arg Pro Arg Val Val Gly Leu
    1010                1015                1020

Gly Pro Thr His Arg Ala Val Gly Glu Met Arg Ser Ala Gly Val
    1025                1030                1035

Asp Ala Gln Thr Leu Ala Ser Phe Leu His Asp Thr Gln Leu Gln
    1040                1045                1050

Gln Arg Ser Gly Glu Thr Pro Asp Phe Ser Asn Thr Leu Phe Leu
    1055                1060                1065

Leu Asp Glu Ser Ser Met Val Gly Asn Thr Glu Met Ala Arg Ala
    1070                1075                1080

Tyr Ala Leu Ile Ala Ala Gly Gly Gly Arg Ala Val Ala Ser Gly
    1085                1090                1095

Asp Thr Asp Gln Leu Gln Ala Ile Ala Pro Gly Gln Ser Phe Arg
    1100                1105                1110

Leu Gln Gln Thr Arg Ser Ala Ala Asp Val Val Ile Met Lys Glu
    1115                1120                1125

Ile Val Arg Gln Thr Pro Glu Leu Arg Glu Ala Val Tyr Ser Leu
    1130                1135                1140

Ile Asn Arg Asp Val Glu Arg Ala Leu Ser Gly Leu Glu Ser Val
    1145                1150                1155

Lys Pro Ser Gln Val Pro Arg Leu Glu Gly Ala Trp Ala Pro Glu
    1160                1165                1170

His Ser Val Thr Glu Phe Ser His Ser Gln Glu Ala Lys Leu Ala
    1175                1180                1185

Glu Ala Gln Gln Lys Ala Met Leu Lys Gly Glu Ala Phe Pro Asp
    1190                1195                1200

Ile Pro Met Thr Leu Tyr Glu Ala Ile Val Arg Asp Tyr Thr Gly
    1205                1210                1215

Arg Thr Pro Glu Ala Arg Glu Gln Thr Leu Ile Val Thr His Leu
    1220                1225                1230

Asn Glu Asp Arg Arg Val Leu Asn Ser Met Ile His Asp Ala Arg
    1235                1240                1245

Glu Lys Ala Gly Glu Leu Gly Lys Glu Gln Val Met Val Pro Val
    1250                1255                1260
```

-continued

Leu Asn Thr Ala Asn Ile Arg Asp Gly Glu Leu Arg Arg Leu Ser
1265                1270                1275

Thr Trp Glu Lys Asn Pro Asp Ala Leu Ala Leu Val Asp Asn Val
1280                1285                1290

Tyr His Arg Ile Ala Gly Ile Ser Lys Asp Asp Gly Leu Ile Thr
1295                1300                1305

Leu Gln Asp Ala Glu Gly Asn Thr Arg Leu Ile Ser Pro Arg Glu
1310                1315                1320

Ala Val Ala Glu Gly Val Thr Leu Tyr Thr Pro Asp Lys Ile Arg
1325                1330                1335

Val Gly Thr Gly Asp Arg Met Arg Phe Thr Lys Ser Asp Arg Glu
1340                1345                1350

Arg Gly Tyr Val Ala Asn Ser Val Trp Thr Val Thr Ala Val Ser
1355                1360                1365

Gly Asp Ser Val Thr Leu Ser Asp Gly Gln Gln Thr Arg Val Ile
1370                1375                1380

Arg Pro Gly Gln Glu Arg Ala Glu Gln His Ile Asp Leu Ala Tyr
1385                1390                1395

Ala Ile Thr Ala His Gly Ala Gln Gly Ala Ser Glu Thr Phe Ala
1400                1405                1410

Ile Ala Leu Glu Gly Thr Glu Gly Asn Arg Lys Leu Met Ala Gly
1415                1420                1425

Phe Glu Ser Ala Tyr Val Ala Leu Ser Arg Met Lys Gln His Val
1430                1435                1440

Gln Val Tyr Thr Asp Asn Arg Gln Gly Trp Thr Asp Ala Ile Asn
1445                1450                1455

Asn Ala Val Gln Lys Gly Thr Ala His Asp Val Leu Glu Pro Lys
1460                1465                1470

Pro Asp Arg Glu Val Met Asn Ala Gln Arg Leu Phe Ser Thr Ala
1475                1480                1485

Arg Glu Leu Arg Asp Val Ala Ala Gly Arg Ala Val Leu Arg Gln
1490                1495                1500

Ala Gly Leu Ala Gly Gly Asp Ser Pro Ala Arg Phe Ile Ala Pro
1505                1510                1515

Gly Arg Lys Tyr Pro Gln Pro Tyr Val Ala Leu Pro Ala Phe Asp
1520                1525                1530

Arg Asn Gly Lys Ser Ala Gly Ile Trp Leu Asn Pro Leu Thr Thr
1535                1540                1545

Asp Asp Gly Asn Gly Leu Arg Gly Phe Ser Gly Glu Gly Arg Val
1550                1555                1560

Lys Gly Ser Gly Asp Ala Gln Phe Val Ala Leu Gln Gly Ser Arg
1565                1570                1575

Asn Gly Glu Ser Leu Leu Ala Asp Asn Met Gln Asp Gly Val Arg
1580                1585                1590

Ile Ala Arg Asp Asn Pro Asp Ser Gly Val Val Val Arg Ile Ala
1595                1600                1605

Gly Glu Gly Arg Pro Trp Asn Pro Gly Ala Ile Thr Gly Gly Arg
1610                1615                1620

Val Trp Gly Asp Ile Pro Asp Asn Ser Val Gln Pro Gly Ala Gly
1625                1630                1635

Asn Gly Glu Pro Val Thr Ala Glu Val Leu Ala Gln Arg Gln Ala
1640                1645                1650

Glu Glu Ala Ile Arg Arg Glu Thr Glu Arg Arg Ala Asp Glu Ile

```
                 1655                1660                1665

Val  Arg  Lys  Met  Ala  Glu  Asn  Lys  Pro  Asp  Leu  Pro  Asp  Gly  Lys
                 1670                1675                1680

Thr  Glu  Leu  Ala  Val  Arg  Asp  Ile  Ala  Gly  Gln  Glu  Arg  Asp  Arg
                 1685                1690                1695

Ser  Ala  Ile  Ser  Glu  Arg  Glu  Thr  Ala  Leu  Pro  Glu  Ser  Val  Leu
                 1700                1705                1710

Arg  Glu  Ser  Gln  Arg  Glu  Arg  Glu  Ala  Val  Arg  Glu  Val  Ala  Arg
                 1715                1720                1725

Glu  Asn  Leu  Leu  Gln  Glu  Arg  Leu  Gln  Gln  Met  Glu  Arg  Asp  Met
                 1730                1735                1740

Val  Arg  Asp  Leu  Gln  Lys  Glu  Lys  Thr  Leu  Gly  Gly  Asp
                 1745                1750                1755

<210> SEQ ID NO 23
<211> LENGTH: 726
<212> TYPE: PRT
<213> ORGANISM: Methanococcoides burtonii

<400> SEQUENCE: 23

Met  Ser  Asp  Lys  Pro  Ala  Phe  Met  Lys  Tyr  Phe  Thr  Gln  Ser  Ser  Cys
1                  5                   10                  15

Tyr  Pro  Asn  Gln  Gln  Glu  Ala  Met  Asp  Arg  Ile  His  Ser  Ala  Leu  Met
                   20                  25                  30

Gln  Gln  Gln  Leu  Val  Leu  Phe  Glu  Gly  Ala  Cys  Gly  Thr  Gly  Lys  Thr
              35                  40                  45

Leu  Ser  Ala  Leu  Val  Pro  Ala  Leu  His  Val  Gly  Lys  Met  Leu  Gly  Lys
50                  55                  60

Thr  Val  Ile  Ile  Ala  Thr  Asn  Val  His  Gln  Gln  Met  Val  Gln  Phe  Ile
65                  70                  75                  80

Asn  Glu  Ala  Arg  Asp  Ile  Lys  Lys  Val  Gln  Asp  Val  Lys  Val  Ala  Val
                   85                  90                  95

Ile  Lys  Gly  Lys  Thr  Ala  Met  Cys  Pro  Gln  Glu  Ala  Asp  Tyr  Glu  Glu
                   100                 105                 110

Cys  Ser  Val  Lys  Arg  Glu  Asn  Thr  Phe  Glu  Leu  Met  Glu  Thr  Glu  Arg
              115                 120                 125

Glu  Ile  Tyr  Leu  Lys  Arg  Gln  Glu  Leu  Asn  Ser  Ala  Arg  Asp  Ser  Tyr
130                 135                 140

Lys  Lys  Ser  His  Asp  Pro  Ala  Phe  Val  Thr  Leu  Arg  Asp  Glu  Leu  Ser
145                 150                 155                 160

Lys  Glu  Ile  Asp  Ala  Val  Glu  Glu  Lys  Ala  Arg  Gly  Leu  Arg  Asp  Arg
                   165                 170                 175

Ala  Cys  Asn  Asp  Leu  Tyr  Glu  Val  Leu  Arg  Ser  Asp  Ser  Glu  Lys  Phe
                   180                 185                 190

Arg  Glu  Trp  Leu  Tyr  Lys  Glu  Val  Arg  Ser  Pro  Glu  Glu  Ile  Asn  Asp
              195                 200                 205

His  Ala  Ile  Lys  Asp  Gly  Met  Cys  Gly  Tyr  Glu  Leu  Val  Lys  Arg  Glu
210                 215                 220

Leu  Lys  His  Ala  Asp  Leu  Leu  Ile  Cys  Asn  Tyr  His  His  Val  Leu  Asn
225                 230                 235                 240

Pro  Asp  Ile  Phe  Ser  Thr  Val  Leu  Gly  Trp  Ile  Glu  Lys  Glu  Pro  Gln
                   245                 250                 255

Glu  Thr  Ile  Val  Ile  Phe  Asp  Glu  Ala  His  Asn  Leu  Glu  Ser  Ala  Ala
                   260                 265                 270
```

```
Arg Ser His Ser Ser Leu Ser Leu Thr Glu His Ser Ile Glu Lys Ala
            275                 280                 285

Ile Thr Glu Leu Glu Ala Asn Leu Asp Leu Leu Ala Asp Asp Asn Ile
290                 295                 300

His Asn Leu Phe Asn Ile Phe Leu Glu Val Ile Ser Asp Thr Tyr Asn
305                 310                 315                 320

Ser Arg Phe Lys Phe Gly Glu Arg Glu Arg Val Arg Lys Asn Trp Tyr
                325                 330                 335

Asp Ile Arg Ile Ser Asp Pro Tyr Glu Arg Asn Asp Ile Val Arg Gly
            340                 345                 350

Lys Phe Leu Arg Gln Ala Lys Gly Asp Phe Gly Glu Lys Asp Asp Ile
        355                 360                 365

Gln Ile Leu Leu Ser Glu Ala Ser Glu Leu Gly Ala Lys Leu Asp Glu
370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
                405                 410                 415

Ser His Asn Leu Asn Tyr Tyr Pro Ile Leu Asn Val Arg Arg Asp Met
            420                 425                 430

Asn Asp Glu Ile Tyr Gly Arg Val Glu Leu Phe Thr Cys Ile Pro Lys
        435                 440                 445

Asn Val Thr Glu Pro Leu Phe Asn Ser Leu Phe Ser Val Ile Leu Met
450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                485                 490                 495

Lys Arg Leu Ser Ile Ala Val Ser Ile Pro Pro Leu Phe Ala Lys Asn
            500                 505                 510

Arg Asp Asp Arg His Val Thr Glu Leu Leu Glu Gln Val Leu Leu Asp
        515                 520                 525

Ser Ile Glu Asn Ser Lys Gly Asn Val Ile Leu Phe Phe Gln Ser Ala
530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
                565                 570                 575

Glu Phe Phe Ser Ile Gly Glu Leu Asn Gly Lys Ala Val Leu Leu Ser
            580                 585                 590

Tyr Leu Trp Gly Thr Leu Ser Glu Gly Ile Asp Tyr Arg Asp Gly Arg
        595                 600                 605

Gly Arg Thr Val Ile Ile Ile Gly Val Gly Tyr Pro Ala Leu Asn Asp
610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
                645                 650                 655

Gln Ala Met Gly Arg Val Val Arg Ser Pro Thr Asp Tyr Gly Ala Arg
            660                 665                 670

Ile Leu Leu Asp Gly Arg Phe Leu Thr Asp Ser Lys Lys Arg Phe Gly
        675                 680                 685

Lys Phe Ser Val Phe Glu Val Phe Pro Pro Ala Glu Arg Ser Glu Phe
```

```
                690                 695                 700
Val Asp Val Asp Pro Glu Lys Val Lys Tyr Ser Leu Met Asn Phe Phe
705                 710                 715                 720

Met Asp Asn Asp Glu Gln
            725

<210> SEQ ID NO 24
<211> LENGTH: 30
<212> TYPE: DNA
<213> ORGANISM: Artificial sequence
<220> FEATURE:
<223> OTHER INFORMATION: Example sequence

<400> SEQUENCE: 24
atgccatgat acttaccatt aggccacacg                                    30

<210> SEQ ID NO 25
<211> LENGTH: 30
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (5)..(5)
<223> OTHER INFORMATION: I
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: modified_base
<222> LOCATION: (7)..(7)
<223> OTHER INFORMATION: I
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (11)..(11)
<223> OTHER INFORMATION: I
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: modified_base
<222> LOCATION: (13)..(13)
<223> OTHER INFORMATION: I
```

-continued

```
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (17)..(17)
<223> OTHER INFORMATION: I
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: modified_base
<222> LOCATION: (19)..(19)
<223> OTHER INFORMATION: I
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: modified_base
<222> LOCATION: (21)..(21)
<223> OTHER INFORMATION: I
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: modified_base
<222> LOCATION: (23)..(23)
<223> OTHER INFORMATION: I
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: modified_base
<222> LOCATION: (25)..(25)
<223> OTHER INFORMATION: I
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: modified_base
<222> LOCATION: (27)..(27)
<223> OTHER INFORMATION: I
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: modified_base
<222> LOCATION: (29)..(29)
<223> OTHER INFORMATION: I
<220> FEATURE:
<221> NAME/KEY: misc_feature
<222> LOCATION: (29)..(29)
<223> OTHER INFORMATION: n is a, c, g, or t

<400> SEQUENCE: 25
nangntncna ngnangntna ncngntntnc                                            30

<210> SEQ ID NO 26
<211> LENGTH: 15
<212> TYPE: DNA
<213> ORGANISM: Artificial sequence
<220> FEATURE:
```

<223> OTHER INFORMATION: Example sequence

<400> SEQUENCE: 26
agtcagagta cgttc                                                    15

<210> SEQ ID NO 27
<211> LENGTH: 30
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (5)..(5)
<223> OTHER INFORMATION: I
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: modified_base
<222> LOCATION: (7)..(7)
<223> OTHER INFORMATION: I
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (11)..(11)
<223> OTHER INFORMATION: I
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: modified_base
<222> LOCATION: (13)..(13)
<223> OTHER INFORMATION: I
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base

```
<222> LOCATION: (17)..(17)
<223> OTHER INFORMATION: I
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: modified_base
<222> LOCATION: (19)..(19)
<223> OTHER INFORMATION: I
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: modified_base
<222> LOCATION: (21)..(21)
<223> OTHER INFORMATION: I
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: modified_base
<222> LOCATION: (23)..(23)
<223> OTHER INFORMATION: I
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: modified_base
<222> LOCATION: (25)..(25)
<223> OTHER INFORMATION: I
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: modified_base
<222> LOCATION: (27)..(27)
<223> OTHER INFORMATION: I
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: modified_base
<222> LOCATION: (29)..(29)
<223> OTHER INFORMATION: I
<220> FEATURE:
<221> NAME/KEY: misc_feature
<222> LOCATION: (29)..(29)
<223> OTHER INFORMATION: n is a, c, g, or t

<400> SEQUENCE: 27
ntncngnant ntnantngna ntncngngng                                      30

<210> SEQ ID NO 28
<211> LENGTH: 15
<212> TYPE: DNA
<213> ORGANISM: Artificial sequence
<220> FEATURE:
<223> OTHER INFORMATION: Example sequence

<400> SEQUENCE: 28
tcgattatga tcggg                                                      15

<210> SEQ ID NO 29
<211> LENGTH: 30
<212> TYPE: DNA
<213> ORGANISM: Artificial sequence
<220> FEATURE:
<223> OTHER INFORMATION: Example sequence
```

<400> SEQUENCE: 29
tacggtacta tgaatggtaa tccggtgtgc                                    30

<210> SEQ ID NO 30
<211> LENGTH: 30
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (4)..(4)
<223> OTHER INFORMATION: I
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (7)..(7)
<223> OTHER INFORMATION: I
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: modified_base
<222> LOCATION: (8)..(8)
<223> OTHER INFORMATION: I
<220> FEATURE:
<221> NAME/KEY: modified_base
<222> LOCATION: (10)..(10)
<223> OTHER INFORMATION: I
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: modified_base
<222> LOCATION: (11)..(11)
<223> OTHER INFORMATION: I
<220> FEATURE:
<221> NAME/KEY: modified_base
<222> LOCATION: (13)..(13)
<223> OTHER INFORMATION: I
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: I
<220> FEATURE:
<221> NAME/KEY: modified_base
<222> LOCATION: (16)..(16)
<223> OTHER INFORMATION: I
<220> FEATURE:
<221> NAME/KEY: misc_feature
<222> LOCATION: (16)..(17)
<223> OTHER INFORMATION: n is a, c, g, or t

```
<220> FEATURE:
<221> NAME/KEY: modified_base
<222> LOCATION: (17)..(17)
<223> OTHER INFORMATION: I
<220> FEATURE:
<221> NAME/KEY: modified_base
<222> LOCATION: (19)..(19)
<223> OTHER INFORMATION: I
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: modified_base
<222> LOCATION: (20)..(20)
<223> OTHER INFORMATION: I
<220> FEATURE:
<221> NAME/KEY: modified_base
<222> LOCATION: (22)..(22)
<223> OTHER INFORMATION: I
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: modified_base
<222> LOCATION: (23)..(23)
<223> OTHER INFORMATION: I
<220> FEATURE:
<221> NAME/KEY: modified_base
<222> LOCATION: (25)..(25)
<223> OTHER INFORMATION: I
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: modified_base
<222> LOCATION: (26)..(26)
<223> OTHER INFORMATION: I
<220> FEATURE:
<221> NAME/KEY: modified_base
<222> LOCATION: (28)..(28)
<223> OTHER INFORMATION: I
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: modified_base
<222> LOCATION: (29)..(29)
<223> OTHER INFORMATION: I

<400> SEQUENCE: 30
nncnntnntn ngnntnntnn tnngnngnnc                                    30

<210> SEQ ID NO 31
<211> LENGTH: 30
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (4)..(4)
```

-continued

```
<223> OTHER INFORMATION: I
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (7)..(7)
<223> OTHER INFORMATION: I
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: modified_base
<222> LOCATION: (8)..(8)
<223> OTHER INFORMATION: I
<220> FEATURE:
<221> NAME/KEY: modified_base
<222> LOCATION: (10)..(10)
<223> OTHER INFORMATION: I
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: modified_base
<222> LOCATION: (11)..(11)
<223> OTHER INFORMATION: I
<220> FEATURE:
<221> NAME/KEY: modified_base
<222> LOCATION: (13)..(13)
<223> OTHER INFORMATION: I
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: I
<220> FEATURE:
<221> NAME/KEY: modified_base
<222> LOCATION: (16)..(16)
<223> OTHER INFORMATION: I
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: modified_base
<222> LOCATION: (17)..(17)
<223> OTHER INFORMATION: I
<220> FEATURE:
<221> NAME/KEY: modified_base
<222> LOCATION: (19)..(19)
<223> OTHER INFORMATION: I
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: modified_base
<222> LOCATION: (20)..(20)
<223> OTHER INFORMATION: I
<220> FEATURE:
<221> NAME/KEY: modified_base
<222> LOCATION: (22)..(22)
<223> OTHER INFORMATION: I
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: modified_base
```

```
<222> LOCATION: (23)..(23)
<223> OTHER INFORMATION: I
<220> FEATURE:
<221> NAME/KEY: modified_base
<222> LOCATION: (25)..(25)
<223> OTHER INFORMATION: I
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: modified_base
<222> LOCATION: (26)..(26)
<223> OTHER INFORMATION: I
<220> FEATURE:
<221> NAME/KEY: modified_base
<222> LOCATION: (28)..(28)
<223> OTHER INFORMATION: I
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: modified_base
<222> LOCATION: (29)..(29)
<223> OTHER INFORMATION: I

<400> SEQUENCE: 31
nnanngnncn ntnnanngnn anncnntnng                                              30

<210> SEQ ID NO 32
<211> LENGTH: 30
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (4)..(4)
<223> OTHER INFORMATION: I
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (7)..(7)
<223> OTHER INFORMATION: I
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: modified_base
<222> LOCATION: (8)..(8)
<223> OTHER INFORMATION: I
<220> FEATURE:
<221> NAME/KEY: modified_base
<222> LOCATION: (10)..(10)
<223> OTHER INFORMATION: I
<220> FEATURE:
```

-continued

```
<221> NAME/KEY: misc_feature
<222> LOCATION: (10)..(11)
<223> OTHER INFORMATION: n is a, c, g, or t
<220> FEATURE:
<221> NAME/KEY: modified_base
<222> LOCATION: (11)..(11)
<223> OTHER INFORMATION: I
<220> FEATURE:
<221> NAME/KEY: modified_base
<222> LOCATION: (13)..(13)
<223> OTHER INFORMATION: I
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: modified_base
<222> LOCATION: (14)..(14)
<223> OTHER INFORMATION: I
<220> FEATURE:
<221> NAME/KEY: modified_base
<222> LOCATION: (16)..(16)
<223> OTHER INFORMATION: I
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: modified_base
<222> LOCATION: (17)..(17)
<223> OTHER INFORMATION: I
<220> FEATURE:
<221> NAME/KEY: modified_base
<222> LOCATION: (19)..(19)
<223> OTHER INFORMATION: I
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: modified_base
<222> LOCATION: (20)..(20)
<223> OTHER INFORMATION: I
<220> FEATURE:
<221> NAME/KEY: modified_base
<222> LOCATION: (22)..(22)
<223> OTHER INFORMATION: I
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: modified_base
<222> LOCATION: (23)..(23)
<223> OTHER INFORMATION: I
<220> FEATURE:
<221> NAME/KEY: modified_base
<222> LOCATION: (25)..(25)
<223> OTHER INFORMATION: I
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: modified_base
<222> LOCATION: (26)..(26)
<223> OTHER INFORMATION: I
<220> FEATURE:
<221> NAME/KEY: modified_base
<222> LOCATION: (28)..(28)
<223> OTHER INFORMATION: I
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: modified_base
<222> LOCATION: (29)..(29)
<223> OTHER INFORMATION: I
```

<400> SEQUENCE: 32
nntnngnnan nannanngnn anncnngnnt         30

<210> SEQ ID NO 33
<211> LENGTH: 31
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (8)..(8)
<223> OTHER INFORMATION: I
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: modified_base
<222> LOCATION: (10)..(10)
<223> OTHER INFORMATION: I
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: modified_base
<222> LOCATION: (12)..(12)
<223> OTHER INFORMATION: I
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: modified_base
<222> LOCATION: (14)..(14)
<223> OTHER INFORMATION: I
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: modified_base
<222> LOCATION: (16)..(16)
<223> OTHER INFORMATION: I
<220> FEATURE:
<221> NAME/KEY: misc_feature
<222> LOCATION: (16)..(16)

```
<223> OTHER INFORMATION: n is a, c, g, or t
<220> FEATURE:
<221> NAME/KEY: modified_base
<222> LOCATION: (18)..(18)
<223> OTHER INFORMATION: I
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: modified_base
<222> LOCATION: (20)..(20)
<223> OTHER INFORMATION: I
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: modified_base
<222> LOCATION: (22)..(22)
<223> OTHER INFORMATION: I
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: modified_base
<222> LOCATION: (24)..(24)
<223> OTHER INFORMATION: I
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: modified_base
<222> LOCATION: (26)..(26)
<223> OTHER INFORMATION: I
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: modified_base
<222> LOCATION: (28)..(28)
<223> OTHER INFORMATION: I
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: modified_base
<222> LOCATION: (30)..(30)
<223> OTHER INFORMATION: I
<220> FEATURE:
<221> NAME/KEY: misc_feature
<222> LOCATION: (30)..(30)
<223> OTHER INFORMATION: n is a, c, g, or t

<400> SEQUENCE: 33
nnnngnantn tnantngnan tncngngngn c                                    31

<210> SEQ ID NO 34
<211> LENGTH: 30
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
```

```
<222> LOCATION: (2)..(2)
<223> OTHER INFORMATION: I
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: modified_base
<222> LOCATION: (7)..(7)
<223> OTHER INFORMATION: I
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (11)..(11)
<223> OTHER INFORMATION: I
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: modified_base
<222> LOCATION: (13)..(13)
<223> OTHER INFORMATION: I
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (17)..(17)
<223> OTHER INFORMATION: I
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: modified_base
<222> LOCATION: (19)..(19)
<223> OTHER INFORMATION: I
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: modified_base
<222> LOCATION: (21)..(21)
<223> OTHER INFORMATION: I
<220> FEATURE:
<221> NAME/KEY: misc_feature
<222> LOCATION: (21)..(21)
<223> OTHER INFORMATION: n is a, c, g, or t
<220> FEATURE:
```

```
<221> NAME/KEY: modified_base
<222> LOCATION: (23)..(23)
<223> OTHER INFORMATION: I
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: modified_base
<222> LOCATION: (25)..(25)
<223> OTHER INFORMATION: I
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: modified_base
<222> LOCATION: (27)..(27)
<223> OTHER INFORMATION: I
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: modified_base
<222> LOCATION: (29)..(29)
<223> OTHER INFORMATION: I
<220> FEATURE:
<221> NAME/KEY: misc_feature
<222> LOCATION: (29)..(29)
<223> OTHER INFORMATION: n is a, c, g, or t

<400> SEQUENCE: 34
nnngntncna ngnangntna ncngntntnc                               30

<210> SEQ ID NO 35
<211> LENGTH: 27
<212> TYPE: DNA
<213> ORGANISM: Artificial sequence
<220> FEATURE:
<223> OTHER INFORMATION: Example sequence

<400> SEQUENCE: 35
ggtactatga atggtaatcc ggtgtgc                                  27

<210> SEQ ID NO 36
<211> LENGTH: 33
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(3)
<223> OTHER INFORMATION: n is a, c, g, or t

<400> SEQUENCE: 36
nnnatgccat gatacttacc attaggccac acg                           33

<210> SEQ ID NO 37
<211> LENGTH: 32
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(2)
<223> OTHER INFORMATION: n is a, c, g, or t

<400> SEQUENCE: 37
nnatgccatg atacttacca ttaggccaca cg                            32
```

```
<210> SEQ ID NO 38
<211> LENGTH: 34
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: modified_base
<222> LOCATION: (7)..(7)
<223> OTHER INFORMATION: I
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (11)..(11)
<223> OTHER INFORMATION: I
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: modified_base
<222> LOCATION: (13)..(13)
<223> OTHER INFORMATION: I
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (17)..(17)
<223> OTHER INFORMATION: I
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: modified_base
<222> LOCATION: (19)..(19)
```

```
<223> OTHER INFORMATION: I
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: modified_base
<222> LOCATION: (21)..(21)
<223> OTHER INFORMATION: I
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: modified_base
<222> LOCATION: (23)..(23)
<223> OTHER INFORMATION: I
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: modified_base
<222> LOCATION: (25)..(25)
<223> OTHER INFORMATION: I
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: modified_base
<222> LOCATION: (27)..(27)
<223> OTHER INFORMATION: I
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: modified_base
<222> LOCATION: (29)..(29)
<223> OTHER INFORMATION: I
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: modified_base
<222> LOCATION: (31)..(31)
<223> OTHER INFORMATION: I
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: modified_base
<222> LOCATION: (33)..(33)
<223> OTHER INFORMATION: I
<220> FEATURE:
<221> NAME/KEY: misc_feature
<222> LOCATION: (33)..(33)
<223> OTHER INFORMATION: n is a, c, g, or t

<400> SEQUENCE: 38
nnntncngna ntntnantng nantncngng ncna                                     34

<210> SEQ ID NO 39
<211> LENGTH: 32
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
```

-continued

```
<222> LOCATION: (1)..(3)
<223> OTHER INFORMATION: n is a, c, g, or t
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: modified_base
<222> LOCATION: (7)..(7)
<223> OTHER INFORMATION: I
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (11)..(11)
<223> OTHER INFORMATION: I
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: modified_base
<222> LOCATION: (13)..(13)
<223> OTHER INFORMATION: I
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (17)..(17)
<223> OTHER INFORMATION: I
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: modified_base
<222> LOCATION: (19)..(19)
<223> OTHER INFORMATION: I
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: modified_base
<222> LOCATION: (21)..(21)
<223> OTHER INFORMATION: I
<220> FEATURE:
<221> NAME/KEY: misc_feature
<222> LOCATION: (21)..(21)
<223> OTHER INFORMATION: n is a, c, g, or t
<220> FEATURE:
```

```
<221> NAME/KEY: modified_base
<222> LOCATION: (23)..(23)
<223> OTHER INFORMATION: I
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: modified_base
<222> LOCATION: (25)..(25)
<223> OTHER INFORMATION: I
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: modified_base
<222> LOCATION: (27)..(27)
<223> OTHER INFORMATION: I
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: modified_base
<222> LOCATION: (29)..(29)
<223> OTHER INFORMATION: I
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: modified_base
<222> LOCATION: (31)..(31)
<223> OTHER INFORMATION: I
<220> FEATURE:
<221> NAME/KEY: misc_feature
<222> LOCATION: (31)..(31)
<223> OTHER INFORMATION: n is a, c, g, or t

<400> SEQUENCE: 39
nnnangntnc nangnangnt nancngntnt nc                                     32

<210> SEQ ID NO 40
<211> LENGTH: 42
<212> TYPE: DNA
<213> ORGANISM: Artificial sequence
<220> FEATURE:
<223> OTHER INFORMATION: Example sequence

<400> SEQUENCE: 40
tattgacgtc cttccccgta cgccgggcaa taacgtttat gt                          42

<210> SEQ ID NO 41
<211> LENGTH: 42
<212> TYPE: DNA
<213> ORGANISM: Artificial sequence
<220> FEATURE:
<223> OTHER INFORMATION: Example sequence

<400> SEQUENCE: 41
acataaacgt tattgcccgg cgtacgggga aggacgtcaa ta                          42

<210> SEQ ID NO 42
<211> LENGTH: 7
<212> TYPE: DNA
<213> ORGANISM: Artificial sequence
<220> FEATURE:
<223> OTHER INFORMATION: Example sequence

<400> SEQUENCE: 42 acataaa                                                                 7
```

```
<210> SEQ ID NO 43
<211> LENGTH: 7
<212> TYPE: DNA
<213> ORGANISM: Artificial sequence
<220> FEATURE:
<223> OTHER INFORMATION: Example sequence

<400> SEQUENCE: 43 cgttatt                                                              7

<210> SEQ ID NO 44
<211> LENGTH: 7
<212> TYPE: DNA
<213> ORGANISM: Artificial sequence
<220> FEATURE:
<223> OTHER INFORMATION: Example sequence

<400> SEQUENCE: 44 gcccggc                                                              7

<210> SEQ ID NO 45
<211> LENGTH: 7
<212> TYPE: DNA
<213> ORGANISM: Artificial sequence
<220> FEATURE:
<223> OTHER INFORMATION: Example sequence

<400> SEQUENCE: 45 gtacggg                                                              7

<210> SEQ ID NO 46
<211> LENGTH: 7
<212> TYPE: DNA
<213> ORGANISM: Artificial sequence
<220> FEATURE:
<223> OTHER INFORMATION: Example sequence

<400> SEQUENCE: 46 gaaggac                                                              7

<210> SEQ ID NO 47
<211> LENGTH: 7
<212> TYPE: DNA
<213> ORGANISM: Artificial sequence
<220> FEATURE:
<223> OTHER INFORMATION: Example sequence

<400> SEQUENCE: 47 gtcaata                                                              7

<210> SEQ ID NO 48

<400> SEQUENCE: 48

000

<210> SEQ ID NO 49
<211> LENGTH: 57
<212> TYPE: DNA
<213> ORGANISM: Artificial sequence
<220> FEATURE:
<223> OTHER INFORMATION: Example sequence

<400> SEQUENCE: 49
tttttttttt tttttttttt tttttttttt tttttttttt tttttttttt acataaa      57
```

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54
<211> LENGTH: 7
<212> TYPE: DNA
<213> ORGANISM: Artificial sequence
<220> FEATURE:
<223> OTHER INFORMATION: Example sequence

<400> SEQUENCE: 54 gtcaata                                                                 7

<210> SEQ ID NO 55
<211> LENGTH: 46
<212> TYPE: DNA
<213> ORGANISM: Artificial sequence
<220> FEATURE:
<223> OTHER INFORMATION: Example sequence

<400> SEQUENCE: 55
ttacagtaga caggtcactc acctgcatgt cactccgttg tcgttc             46

<210> SEQ ID NO 56
<211> LENGTH: 39
<212> TYPE: DNA
<213> ORGANISM: Artificial sequence
<220> FEATURE:
<223> OTHER INFORMATION: Example sequence

<400> SEQUENCE: 56
aacatcacct agcctgcgaa cgacaacgga gtgacatgc                    39

<210> SEQ ID NO 57
<211> LENGTH: 41
<212> TYPE: DNA
<213> ORGANISM: Artificial sequence
<220> FEATURE:
<223> OTHER INFORMATION: Example sequence

<400> SEQUENCE: 57
aggtgagtga cctgtctact gtaagatgca gtctctcgtg g                 41

<210> SEQ ID NO 58

```
<211> LENGTH: 46
<212> TYPE: DNA
<213> ORGANISM: Artificial sequence
<220> FEATURE:
<223> OTHER INFORMATION: Example sequence

<400> SEQUENCE: 58
ttacagtaga caggtcactc aagagaaagt cactccgttg tcgttc                    46

<210> SEQ ID NO 59
<211> LENGTH: 39
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (36)..(36)
<223> OTHER INFORMATION: I
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: modified_base
<222> LOCATION: (38)..(38)
<223> OTHER INFORMATION: I

<400> SEQUENCE: 59
aacatcacct agcctgcgaa cgacaacgga gtgacntnc                             39

<210> SEQ ID NO 60
<211> LENGTH: 41
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(3)
<223> OTHER INFORMATION: n is a, c, g, or t

<400> SEQUENCE: 60
ncntgagtga cctgtctact gtaagatgca gtctctcgtg g                          41

<210> SEQ ID NO 61
<211> LENGTH: 46
<212> TYPE: DNA
<213> ORGANISM: Artificial sequence
<220> FEATURE:
<223> OTHER INFORMATION: Example sequence

<400> SEQUENCE: 61
ttacagtaga caggtcactc atgtgtatgt cactccgttg tcgttc                    46
```

```
<210> SEQ ID NO 62
<211> LENGTH: 46
<212> TYPE: DNA
<213> ORGANISM: Artificial sequence
<220> FEATURE:
<223> OTHER INFORMATION: Example sequence

<400> SEQUENCE: 62
ttacagtaga caggtcactc acgcgcacgt cactccgttg tcgttc           46

<210> SEQ ID NO 63
<211> LENGTH: 46
<212> TYPE: DNA
<213> ORGANISM: Artificial sequence
<220> FEATURE:
<223> OTHER INFORMATION: Example sequence

<400> SEQUENCE: 63
ttacagtaga caggtcactc aggcggaggt cactccgttg tcgttc           46

<210> SEQ ID NO 64
<211> LENGTH: 46
<212> TYPE: DNA
<213> ORGANISM: Artificial sequence
<220> FEATURE:
<223> OTHER INFORMATION: Example sequence

<400> SEQUENCE: 64
ttacagtaga caggtcactc aaaggaaagt cactccgttg tcgttc           46

<210> SEQ ID NO 65
<211> LENGTH: 39
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (37)..(37)
<223> OTHER INFORMATION: I
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: modified_base
<222> LOCATION: (38)..(38)
<223> OTHER INFORMATION: I

<400> SEQUENCE: 65
aacatcacct agcctgcgaa cgacaacgga gtgactnnc                   39

<210> SEQ ID NO 66
<211> LENGTH: 41
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (2)..(2)
<223> OTHER INFORMATION: I
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: modified_base
<222> LOCATION: (3)..(3)
<223> OTHER INFORMATION: I
```

<400> SEQUENCE: 66
cnntgagtga cctgtctact gtaagatgca gtctctcgtg g					41

<210> SEQ ID NO 67
<211> LENGTH: 46
<212> TYPE: DNA
<213> ORGANISM: Artificial sequence
<220> FEATURE:
<223> OTHER INFORMATION: Example sequence

<400> SEQUENCE: 67
ttacagtaga caggtcactc attggttagt cactccgttg tcgttc					46

<210> SEQ ID NO 68
<211> LENGTH: 46
<212> TYPE: DNA
<213> ORGANISM: Artificial sequence
<220> FEATURE:
<223> OTHER INFORMATION: Example sequence

<400> SEQUENCE: 68
ttacagtaga caggtcactc accggccagt cactccgttg tcgttc					46

<210> SEQ ID NO 69
<211> LENGTH: 46
<212> TYPE: DNA
<213> ORGANISM: Artificial sequence
<220> FEATURE:
<223> OTHER INFORMATION: Example sequence

<400> SEQUENCE: 69
ttacagtaga caggtcactc acggggagt cactccgttg tcgttc					46

<210> SEQ ID NO 70
<211> LENGTH: 48
<212> TYPE: DNA
<213> ORGANISM: Artificial sequence
<220> FEATURE:
<223> OTHER INFORMATION: Example sequence

<400> SEQUENCE: 70
ttacagtaga caggtcactc aacaggaaca gtcactccgt tgtcgttc					48

<210> SEQ ID NO 71
<211> LENGTH: 40
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (36)..(36)
<223> OTHER INFORMATION: I
<220> FEATURE:
<221> NAME/KEY: misc_feature
<222> LOCATION: (36)..(38)
<223> OTHER INFORMATION: n is a, c, g, or t
<220> FEATURE:
<221> NAME/KEY: modified_base
<222> LOCATION: (37)..(37)
<223> OTHER INFORMATION: I
<220> FEATURE:
<221> NAME/KEY: modified_base
<222> LOCATION: (38)..(38)
<223> OTHER INFORMATION: I

<400> SEQUENCE: 71
aacatcacct agcctgcgaa cgacaacgga gtgacnnntc					40

<210> SEQ ID NO 72
<211> LENGTH: 42
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (2)..(2)
<223> OTHER INFORMATION: I
<220> FEATURE:
<221> NAME/KEY: misc_feature
<222> LOCATION: (2)..(4)
<223> OTHER INFORMATION: n is a, c, g, or t
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (4)..(4)
<223> OTHER INFORMATION: I

<400> SEQUENCE: 72
cnnntgagtg acctgtctac tgtaagatgc agtctctcgt gg    42

<210> SEQ ID NO 73
<211> LENGTH: 48
<212> TYPE: DNA
<213> ORGANISM: Artificial sequence
<220> FEATURE:
<223> OTHER INFORMATION: Example sequence

<400> SEQUENCE: 73
ttacagtaga caggtcactc atttggattt gtcactccgt tgtcgttc    48

<210> SEQ ID NO 74
<211> LENGTH: 48
<212> TYPE: DNA
<213> ORGANISM: Artificial sequence
<220> FEATURE:
<223> OTHER INFORMATION: Example sequence

<400> SEQUENCE: 74
ttacagtaga caggtcactc acccggaccc gtcactccgt tgtcgttc    48

<210> SEQ ID NO 75
<211> LENGTH: 48
<212> TYPE: DNA
<213> ORGANISM: Artificial sequence
<220> FEATURE:
<223> OTHER INFORMATION: Example sequence

<400> SEQUENCE: 75
ttacagtaga caggtcactc agcgggaggc gtcactccgt tgtcgttc    48

<210> SEQ ID NO 76
<211> LENGTH: 46
<212> TYPE: DNA
<213> ORGANISM: Artificial sequence
<220> FEATURE:
<223> OTHER INFORMATION: Example sequence

<400> SEQUENCE: 76
ttacagtaga caggtcactc aaaggaaagt cactccgttg tcgttc    46

<210> SEQ ID NO 77

```
<211> LENGTH: 39
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (36)..(36)
<223> OTHER INFORMATION: I
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: modified_base
<222> LOCATION: (37)..(37)
<223> OTHER INFORMATION: I

<400> SEQUENCE: 77
aacatcacct agcctgcgaa cgacaacgga gtgacnntc                              39

<210> SEQ ID NO 78
<211> LENGTH: 41
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I

<400> SEQUENCE: 78
ctnngagtga cctgtctact gtaagatgca gtctctcgtg g                          41

<210> SEQ ID NO 79
<211> LENGTH: 46
<212> TYPE: DNA
<213> ORGANISM: Artificial sequence
<220> FEATURE:
<223> OTHER INFORMATION: Example sequence

<400> SEQUENCE: 79
ttacagtaga caggtcactc ttaggattgt cactccgttg tcgttc                     46

<210> SEQ ID NO 80
<211> LENGTH: 46
<212> TYPE: DNA
<213> ORGANISM: Artificial sequence
<220> FEATURE:
<223> OTHER INFORMATION: Example sequence

<400> SEQUENCE: 80
ttacagtaga caggtcactc ccaggaccgt cactccgttg tcgttc                     46

<210> SEQ ID NO 81
<211> LENGTH: 46
<212> TYPE: DNA
<213> ORGANISM: Artificial sequence
<220> FEATURE:
<223> OTHER INFORMATION: Example sequence

<400> SEQUENCE: 81
```
ttacagtaga caggtcactc ggaggagggt cactccgttg tcgttc                         46

<210> SEQ ID NO 82
<211> LENGTH: 81
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: modified_base
<222> LOCATION: (36)..(36)
<223> OTHER INFORMATION: I
<220> FEATURE:
<221> NAME/KEY: modified_base
<222> LOCATION: (37)..(37)
<223> OTHER INFORMATION: I
<220> FEATURE:
<221> NAME/KEY: modified_base
<222> LOCATION: (42)..(42)
<223> OTHER INFORMATION: I
<220> FEATURE:
<221> NAME/KEY: modified_base
<222> LOCATION: (43)..(43)
<223> OTHER INFORMATION: I

<400> SEQUENCE: 82
aacatcacct agcctgcgaa cgacaacgga gtgacnntcc tnntgagtga cctgtctact         60
gtaagatgca gtctctcgtg g                                                   81

<210> SEQ ID NO 83

<400> SEQUENCE: 83

000

<210> SEQ ID NO 84
<211> LENGTH: 69
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I

<400> SEQUENCE: 84
aanncgttct gtttatgttt cttgtttgtt agccttttg gctaacaaac aagaaacata          60
aacagaacg                                                                 69

<210> SEQ ID NO 85
<211> LENGTH: 52
<212> TYPE: DNA
<213> ORGANISM: Artificial sequence

```
<220> FEATURE:
<223> OTHER INFORMATION: Example sequence

<400> SEQUENCE: 85
ggttgtttct gttggtgctg atattgcttt tgatgccgac cctaaatttt tt          52

<210> SEQ ID NO 86
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: I

<400> SEQUENCE: 86
acnnacagnn ac                                                       12

<210> SEQ ID NO 87
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: I

<400> SEQUENCE: 87
agnnatatnn gc                                                       12
```

```
<210> SEQ ID NO 88
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: I

<400> SEQUENCE: 88
gtnngcatnn aa                                                            12

<210> SEQ ID NO 89
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: I

<400> SEQUENCE: 89
aannaattnn gg                                                            12

<210> SEQ ID NO 90
<211> LENGTH: 169
<212> TYPE: DNA
<213> ORGANISM: Artificial sequence
<220> FEATURE:
<223> OTHER INFORMATION: Example sequence
```

-continued

```
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: I
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: modified_base
<222> LOCATION: (16)..(16)
<223> OTHER INFORMATION: I
<220> FEATURE:
<221> NAME/KEY: modified_base
<222> LOCATION: (21)..(21)
<223> OTHER INFORMATION: I
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: modified_base
<222> LOCATION: (22)..(22)
<223> OTHER INFORMATION: I
<220> FEATURE:
<221> NAME/KEY: modified_base
<222> LOCATION: (27)..(27)
<223> OTHER INFORMATION: I
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: modified_base
<222> LOCATION: (28)..(28)
<223> OTHER INFORMATION: I
<220> FEATURE:
<221> NAME/KEY: modified_base
<222> LOCATION: (33)..(33)
<223> OTHER INFORMATION: I
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: modified_base
<222> LOCATION: (34)..(34)
<223> OTHER INFORMATION: I
<220> FEATURE:
<221> NAME/KEY: modified_base
<222> LOCATION: (39)..(39)
<223> OTHER INFORMATION: I
<220> FEATURE:
<221> NAME/KEY: misc_feature
<222> LOCATION: (39)..(40)
```

```
<223> OTHER INFORMATION: n is a, c, g, or t
<220> FEATURE:
<221> NAME/KEY: modified_base
<222> LOCATION: (40)..(40)
<223> OTHER INFORMATION: I
<220> FEATURE:
<221> NAME/KEY: modified_base
<222> LOCATION: (45)..(45)
<223> OTHER INFORMATION: I
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: modified_base
<222> LOCATION: (46)..(46)
<223> OTHER INFORMATION: I
<220> FEATURE:
<221> NAME/KEY: modified_base
<222> LOCATION: (51)..(51)
<223> OTHER INFORMATION: I
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: modified_base
<222> LOCATION: (52)..(52)
<223> OTHER INFORMATION: I

<400> SEQUENCE: 90
aannaattnn gggtnngcat nnaaagnnat atnngcacnn acagnnacaa nncgttctgt      60
ttatgtttct tgtttgttag ccttttttggc taacaaacaa gaaacataaa cagaacgggt    120
tgtttctgtt ggtgctgata ttgcttttga tgccgaccct aaattttt                  169

<210> SEQ ID NO 91

<400> SEQUENCE: 91

000

<210> SEQ ID NO 92
<211> LENGTH: 61
<212> TYPE: DNA
<213> ORGANISM: Artificial sequence
<220> FEATURE:
<223> OTHER INFORMATION: Example sequence

<400> SEQUENCE: 92
agtgtttgtt agtcgcatgg cttgcttttt tttcttgttg ccatgcgact aacaaacact    60
t                                                                     61

<210> SEQ ID NO 93
<211> LENGTH: 37
<212> TYPE: DNA
<213> ORGANISM: Artificial sequence
<220> FEATURE:
<223> OTHER INFORMATION: Example sequence

<400> SEQUENCE: 93
cgttctggtt tgttttttt tttgcaaacc agaacgt                              37

<210> SEQ ID NO 94
<211> LENGTH: 47
<212> TYPE: DNA
<213> ORGANISM: Artificial sequence
<220> FEATURE:
<223> OTHER INFORMATION: Example sequence
```

<400> SEQUENCE: 94
ttctgttggt gctgatattg cttttgatgc cgaccctaaa tttttta                            47

<210> SEQ ID NO 95
<211> LENGTH: 47
<212> TYPE: DNA
<213> ORGANISM: Artificial sequence
<220> FEATURE:
<223> OTHER INFORMATION: Example sequence

<400> SEQUENCE: 95
aaaaaattta gggtcggcat caaaagcaat atcagcacca acagaaa                            47

<210> SEQ ID NO 96
<211> LENGTH: 110
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (53)..(53)
<223> OTHER INFORMATION: I
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: modified_base
<222> LOCATION: (54)..(54)
<223> OTHER INFORMATION: I
<220> FEATURE:
<221> NAME/KEY: modified_base
<222> LOCATION: (59)..(59)
<223> OTHER INFORMATION: I
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: modified_base
<222> LOCATION: (60)..(60)
<223> OTHER INFORMATION: I
<220> FEATURE:
<221> NAME/KEY: modified_base
<222> LOCATION: (65)..(65)
<223> OTHER INFORMATION: I
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: modified_base
<222> LOCATION: (66)..(66)
<223> OTHER INFORMATION: I
<220> FEATURE:
<221> NAME/KEY: modified_base
<222> LOCATION: (71)..(71)
<223> OTHER INFORMATION: I
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: modified_base
<222> LOCATION: (72)..(72)
<223> OTHER INFORMATION: I
<220> FEATURE:
<221> NAME/KEY: modified_base
<222> LOCATION: (77)..(77)
<223> OTHER INFORMATION: I
<220> FEATURE:
<221> NAME/KEY: misc_feature
<222> LOCATION: (77)..(78)
<223> OTHER INFORMATION: n is a, c, g, or t

```
<220> FEATURE:
<221> NAME/KEY: modified_base
<222> LOCATION: (78)..(78)
<223> OTHER INFORMATION: I
<220> FEATURE:
<221> NAME/KEY: modified_base
<222> LOCATION: (83)..(83)
<223> OTHER INFORMATION: I
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: modified_base
<222> LOCATION: (84)..(84)
<223> OTHER INFORMATION: I
<220> FEATURE:
<221> NAME/KEY: modified_base
<222> LOCATION: (89)..(89)
<223> OTHER INFORMATION: I
<220> FEATURE:
<221> NAME/KEY: misc_feature
<222> LOCATION: (89)..(90)
<223> OTHER INFORMATION: n is a, c, g, or t
<220> FEATURE:
<221> NAME/KEY: modified_base
<222> LOCATION: (90)..(90)
<223> OTHER INFORMATION: I
<220> FEATURE:
<221> NAME/KEY: modified_base
<222> LOCATION: (95)..(95)
<223> OTHER INFORMATION: I
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: modified_base
<222> LOCATION: (96)..(96)
<223> OTHER INFORMATION: I
<220> FEATURE:
<221> NAME/KEY: modified_base
<222> LOCATION: (101)..(101)
<223> OTHER INFORMATION: I
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: modified_base
<222> LOCATION: (102)..(102)
<223> OTHER INFORMATION: I
<220> FEATURE:
<221> NAME/KEY: modified_base
<222> LOCATION: (107)..(107)
<223> OTHER INFORMATION: I
<220> FEATURE:
<221> NAME/KEY: misc_feature
<222> LOCATION: (107)..(108)
<223> OTHER INFORMATION: n is a, c, g, or t
<220> FEATURE:
<221> NAME/KEY: modified_base
<222> LOCATION: (108)..(108)
<223> OTHER INFORMATION: I

<400> SEQUENCE: 96
tttttttttt tttttttttt tttttttttt tttttttttt tttttttttt agnntttgnn      60
agtcnnatgc nnacaannaa aannagcann ccatnngact nncaaannct                110

<210> SEQ ID NO 97
<211> LENGTH: 12
<212> TYPE: DNA
<213> ORGANISM: Artificial sequence
<220> FEATURE:
<223> OTHER INFORMATION: Example sequence
<220> FEATURE:
```

```
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: I

<400> SEQUENCE: 97
tannaaatnn ag                                                              12

<210> SEQ ID NO 98
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: I

<400> SEQUENCE: 98
ggnnggcann aa                                                              12

<210> SEQ ID NO 99
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
```

```
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: I

<400> SEQUENCE: 99
aannaatann ag                                                            12

<210> SEQ ID NO 100
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: I

<400> SEQUENCE: 100
cannaacann aa                                                            12

<210> SEQ ID NO 101
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
```

```
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: I

<400> SEQUENCE: 101
cgnnctggnn tg                                                           12

<210> SEQ ID NO 102
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: I

<400> SEQUENCE: 102
cannaaaann aa                                                           12

<210> SEQ ID NO 103
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
```

<222> LOCATION: (10)..(10)
<223> OTHER INFORMATION: I

<400> SEQUENCE: 103
cannccagnn cg                                                              12

<210> SEQ ID NO 104
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: I

<400> SEQUENCE: 104
ttnntgttnn tg                                                              12

<210> SEQ ID NO 105
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: I

<400> SEQUENCE: 105
ctnntattnn tt                                                              12

```
<210> SEQ ID NO 106
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: I

<400> SEQUENCE: 106
ttnntgccnn cc                                                          12

<210> SEQ ID NO 107
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: I

<400> SEQUENCE: 107 ctnnattnn ta                                                           12

<210> SEQ ID NO 108
<211> LENGTH: 61
<212> TYPE: DNA
<213> ORGANISM: Artificial sequence
<220> FEATURE:
<223> OTHER INFORMATION: Example sequence
```

<400> SEQUENCE: 108
agtgtttgtt agtcgcatgg cttgctttt tttcttgttg ccatgcgact aacaaacact    60
t                                                                  61

<210> SEQ ID NO 109
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (7)..(7)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: modified_base
<222> LOCATION: (11)..(11)
<223> OTHER INFORMATION: I

<400> SEQUENCE: 109
nnnnnnnnnn nn                                                      12

<210> SEQ ID NO 110
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (8)..(8)
<223> OTHER INFORMATION: I
<220> FEATURE:
<221> NAME/KEY: modified_base
<222> LOCATION: (10)..(10)
<223> OTHER INFORMATION: I
<220> FEATURE:

<221> NAME/KEY: modified_base
<222> LOCATION: (12)..(12)
<223> OTHER INFORMATION: I

<400> SEQUENCE: 110
nnnnnnnnnn nn                                                                     12

<210> SEQ ID NO 111
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: modified_base
<222> LOCATION: (10)..(10)
<223> OTHER INFORMATION: I

<400> SEQUENCE: 111
nnnnnnnnnn nn                                                                     12

<210> SEQ ID NO 112
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (7)..(7)
<223> OTHER INFORMATION: I
<220> FEATURE:
<221> NAME/KEY: modified_base
<222> LOCATION: (8)..(8)
<223> OTHER INFORMATION: I
<220> FEATURE:
<221> NAME/KEY: modified_base
<222> LOCATION: (11)..(11)
<223> OTHER INFORMATION: I

```
<220> FEATURE:
<221> NAME/KEY: modified_base
<222> LOCATION: (12)..(12)
<223> OTHER INFORMATION: I

<400> SEQUENCE: 112
nnnnnnnnnn nn                                                                      12

<210> SEQ ID NO 113
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (7)..(7)
<223> OTHER INFORMATION: I
<220> FEATURE:
<221> NAME/KEY: modified_base
<222> LOCATION: (8)..(8)
<223> OTHER INFORMATION: I
<220> FEATURE:
<221> NAME/KEY: modified_base
<222> LOCATION: (9)..(9)
<223> OTHER INFORMATION: I

<400> SEQUENCE: 113
nnnnnnnnnn nn                                                                      12

<210> SEQ ID NO 114
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (10)..(10)
<223> OTHER INFORMATION: I
<220> FEATURE:
<221> NAME/KEY: modified_base
<222> LOCATION: (11)..(11)
```

```
<223> OTHER INFORMATION: I
<220> FEATURE:
<221> NAME/KEY: modified_base
<222> LOCATION: (12)..(12)
<223> OTHER INFORMATION: I

<400> SEQUENCE: 114 nnnnnnnnn nn                                                            12

<210> SEQ ID NO 115
<211> LENGTH: 16
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: modified_base
<222> LOCATION: (10)..(10)
<223> OTHER INFORMATION: I
<220> FEATURE:
<221> NAME/KEY: modified_base
<222> LOCATION: (11)..(11)
<223> OTHER INFORMATION: I
<220> FEATURE:
<221> NAME/KEY: modified_base
<222> LOCATION: (12)..(12)
<223> OTHER INFORMATION: I

<400> SEQUENCE: 115 nnnnnnnnn nnnnnn                                                        16

<210> SEQ ID NO 116
<211> LENGTH: 16
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: modified_base
```

```
<222> LOCATION: (7)..(7)
<223> OTHER INFORMATION: I
<220> FEATURE:
<221> NAME/KEY: modified_base
<222> LOCATION: (8)..(8)
<223> OTHER INFORMATION: I
<220> FEATURE:
<221> NAME/KEY: modified_base
<222> LOCATION: (13)..(13)
<223> OTHER INFORMATION: I
<220> FEATURE:
<221> NAME/KEY: modified_base
<222> LOCATION: (14)..(14)
<223> OTHER INFORMATION: I
<220> FEATURE:
<221> NAME/KEY: modified_base
<222> LOCATION: (15)..(15)
<223> OTHER INFORMATION: I
<220> FEATURE:
<221> NAME/KEY: modified_base
<222> LOCATION: (16)..(16)
<223> OTHER INFORMATION: I

<400> SEQUENCE: 116 nnnnnnnnn nnnnnn                                                      16

<210> SEQ ID NO 117
<211> LENGTH: 8
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (7)..(7)
<223> OTHER INFORMATION: I

<400> SEQUENCE: 117 nnnnnnnn                                                               8

<210> SEQ ID NO 118
<211> LENGTH: 8
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (4)..(4)
<223> OTHER INFORMATION: I
<220> FEATURE:
```

```
<221> NAME/KEY: modified_base
<222> LOCATION: (6)..(6)
<223> OTHER INFORMATION: I
<220> FEATURE:
<221> NAME/KEY: modified_base
<222> LOCATION: (8)..(8)
<223> OTHER INFORMATION: I

<400> SEQUENCE: 118 nnnnnnnn                                                                    8

<210> SEQ ID NO 119
<211> LENGTH: 8
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (6)..(6)
<223> OTHER INFORMATION: I

<400> SEQUENCE: 119 nnnnnnnn                                                                    8

<210> SEQ ID NO 120
<211> LENGTH: 8
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (7)..(7)
<223> OTHER INFORMATION: I
<220> FEATURE:
<221> NAME/KEY: modified_base
<222> LOCATION: (8)..(8)
<223> OTHER INFORMATION: I

<400> SEQUENCE: 120 nnnnnnnn                                                                    8

<210> SEQ ID NO 121
<211> LENGTH: 8
```

```
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (4)..(4)
<223> OTHER INFORMATION: I

<400> SEQUENCE: 121 nnnnnnnn                                                             8

<210> SEQ ID NO 122
<211> LENGTH: 8
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (7)..(7)
<223> OTHER INFORMATION: I
<220> FEATURE:
<221> NAME/KEY: modified_base
<222> LOCATION: (8)..(8)
<223> OTHER INFORMATION: I

<400> SEQUENCE: 122 nnnnnnnn                                                             8

<210> SEQ ID NO 123
<211> LENGTH: 9
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: modified_base
<222> LOCATION: (2)..(2)
```

```
<223> OTHER INFORMATION: I
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (7)..(7)
<223> OTHER INFORMATION: I
<220> FEATURE:
<221> NAME/KEY: modified_base
<222> LOCATION: (8)..(8)
<223> OTHER INFORMATION: I

<400> SEQUENCE: 123 nnnnnnnnn                                                                  9

<210> SEQ ID NO 124
<211> LENGTH: 9
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (9)..(9)
<223> OTHER INFORMATION: I

<400> SEQUENCE: 124 nnnnnnnnn                                                                  9

<210> SEQ ID NO 125
<211> LENGTH: 16
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: modified_base
```

```
<222> LOCATION: (6)..(6)
<223> OTHER INFORMATION: I
<220> FEATURE:
<221> NAME/KEY: modified_base
<222> LOCATION: (7)..(7)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: modified_base
<222> LOCATION: (10)..(10)
<223> OTHER INFORMATION: I
<220> FEATURE:
<221> NAME/KEY: modified_base
<222> LOCATION: (11)..(11)
<223> OTHER INFORMATION: I
<220> FEATURE:
<221> NAME/KEY: modified_base
<222> LOCATION: (13)..(13)
<223> OTHER INFORMATION: I
<220> FEATURE:
<221> NAME/KEY: modified_base
<222> LOCATION: (14)..(14)
<223> OTHER INFORMATION: I
<220> FEATURE:
<221> NAME/KEY: modified_base
<222> LOCATION: (15)..(15)
<223> OTHER INFORMATION: I

<400> SEQUENCE: 125 nnnnnnnnn nnnnn                                                    16

<210> SEQ ID NO 126
<211> LENGTH: 16
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (8)..(8)
<223> OTHER INFORMATION: I
<220> FEATURE:
<221> NAME/KEY: modified_base
<222> LOCATION: (12)..(12)
<223> OTHER INFORMATION: I
<220> FEATURE:
<221> NAME/KEY: modified_base
<222> LOCATION: (16)..(16)
<223> OTHER INFORMATION: I

<400> SEQUENCE: 126 nnnnnnnnn nnnnn                                                    16

<210> SEQ ID NO 127
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
```

```
<221> NAME/KEY: misc_feature
<222> LOCATION: (1)..(12)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (7)..(7)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: modified_base
<222> LOCATION: (10)..(10)
<223> OTHER INFORMATION: I
<220> FEATURE:
<221> NAME/KEY: modified_base
<222> LOCATION: (11)..(11)
<223> OTHER INFORMATION: I

<400> SEQUENCE: 127
nnnnnnnnnn nn                                                              12

<210> SEQ ID NO 128
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (8)..(8)
<223> OTHER INFORMATION: I
<220> FEATURE:
<221> NAME/KEY: modified_base
<222> LOCATION: (12)..(12)
<223> OTHER INFORMATION: I

<400> SEQUENCE: 128
nnnnnnnnnn nn                                                              12

<210> SEQ ID NO 129
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(12)
<223> OTHER INFORMATION: n is a, c, g, or t
```

```
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (7)..(7)
<223> OTHER INFORMATION: I
<220> FEATURE:
<221> NAME/KEY: modified_base
<222> LOCATION: (10)..(10)
<223> OTHER INFORMATION: I
<220> FEATURE:
<221> NAME/KEY: modified_base
<222> LOCATION: (11)..(11)
<223> OTHER INFORMATION: I

<400> SEQUENCE: 129
nnnnnnnnnn nn                                                            12

<210> SEQ ID NO 130
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (8)..(8)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: modified_base
<222> LOCATION: (12)..(12)
<223> OTHER INFORMATION: I

<400> SEQUENCE: 130
nnnnnnnnnn nn                                                            12

<210> SEQ ID NO 131
<211> LENGTH: 17
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(17)
```

-continued

```
<223> OTHER INFORMATION: n is a, c, g, or t
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (12)..(12)
<223> OTHER INFORMATION: I
<220> FEATURE:
<221> NAME/KEY: modified_base
<222> LOCATION: (13)..(13)
<223> OTHER INFORMATION: I
<220> FEATURE:
<221> NAME/KEY: modified_base
<222> LOCATION: (14)..(14)
<223> OTHER INFORMATION: I
<220> FEATURE:
<221> NAME/KEY: modified_base
<222> LOCATION: (15)..(15)
<223> OTHER INFORMATION: I

<400> SEQUENCE: 131
nnnnnnnnnn nnnnnnn                                                  17

<210> SEQ ID NO 132
<211> LENGTH: 17
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(17)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (7)..(7)
<223> OTHER INFORMATION: I
<220> FEATURE:
<221> NAME/KEY: modified_base
<222> LOCATION: (8)..(8)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: modified_base
<222> LOCATION: (10)..(10)
<223> OTHER INFORMATION: I
<220> FEATURE:
<221> NAME/KEY: modified_base
<222> LOCATION: (11)..(11)
<223> OTHER INFORMATION: I
<220> FEATURE:
<221> NAME/KEY: modified_base
```

```
<222> LOCATION: (16)..(16)
<223> OTHER INFORMATION: I
<220> FEATURE:
<221> NAME/KEY: modified_base
<222> LOCATION: (17)..(17)
<223> OTHER INFORMATION: I

<400> SEQUENCE: 132 nnnnnnnnn nnnnnn                                              17

<210> SEQ ID NO 133
<211> LENGTH: 8
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (7)..(7)
<223> OTHER INFORMATION: I

<400> SEQUENCE: 133 nnnnnnnn                                                       8

<210> SEQ ID NO 134
<211> LENGTH: 8
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (7)..(7)
<223> OTHER INFORMATION: I
<220> FEATURE:
<221> NAME/KEY: modified_base
<222> LOCATION: (8)..(8)
<223> OTHER INFORMATION: I

<400> SEQUENCE: 134 nnnnnnnn                                                       8

<210> SEQ ID NO 135
<211> LENGTH: 12
<212> TYPE: DNA
```

```
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (7)..(7)
<223> OTHER INFORMATION: I
<220> FEATURE:
<221> NAME/KEY: modified_base
<222> LOCATION: (10)..(10)
<223> OTHER INFORMATION: I
<220> FEATURE:
<221> NAME/KEY: modified_base
<222> LOCATION: (11)..(11)
<223> OTHER INFORMATION: I

<400> SEQUENCE: 135
nnnnnnnnnn nn                                                          12

<210> SEQ ID NO 136
<211> LENGTH: 12
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (8)..(8)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: modified_base
<222> LOCATION: (12)..(12)
<223> OTHER INFORMATION: I

<400> SEQUENCE: 136
nnnnnnnnnn nn                                                          12

<210> SEQ ID NO 137
<211> LENGTH: 8
```

```
<212> TYPE: DNA
<213> ORGANISM: Artificial sequence
<220> FEATURE:
<223> OTHER INFORMATION: Example sequence
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: modified_base
<222> LOCATION: (2)..(2)
<223> OTHER INFORMATION: I
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (7)..(7)
<223> OTHER INFORMATION: I

<400> SEQUENCE: 137 nnnnnnnn                                                               8

<210> SEQ ID NO 138
<211> LENGTH: 8
<212> TYPE: DNA
<213> ORGANISM: Artificial sequence
<220> FEATURE:
<223> OTHER INFORMATION: Example sequence
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (5)..(5)
<223> OTHER INFORMATION: I
<220> FEATURE:
<221> NAME/KEY: modified_base
<222> LOCATION: (8)..(8)
<223> OTHER INFORMATION: I

<400> SEQUENCE: 138 nnnnnnnn                                                               8
```